United States Patent
Pellicciari et al.

(10) Patent No.: US 10,414,791 B2
(45) Date of Patent: Sep. 17, 2019

(54) METHODS FOR PREPARATION OF BILE ACIDS AND DERIVATIVES THEREOF

(71) Applicant: Intercept Pharmaceuticals, Inc., New York, NY (US)

(72) Inventors: Roberto Pellicciari, Perugia (IT); Antimo Gioiello, Perugia (IT)

(73) Assignee: Intercept Pharmaceuticals, Inc, New York, NY (US)

( * ) Notice: Subject to any disclaimer, the term of this patent is extended or adjusted under 35 U.S.C. 154(b) by 23 days.

(21) Appl. No.: 15/748,716

(22) PCT Filed: Jul. 22, 2016

(86) PCT No.: PCT/US2016/043611
§ 371 (c)(1),
(2) Date: Jan. 30, 2018

(87) PCT Pub. No.: WO2017/019524
PCT Pub. Date: Feb. 2, 2017

(65) Prior Publication Data
US 2019/0010184 A1    Jan. 10, 2019

Related U.S. Application Data

(60) Provisional application No. 62/198,733, filed on Jul. 30, 2015.

(51) Int. Cl.
| | | |
|---|---|---|
| *C07J 9/00* | (2006.01) | |
| *C07J 1/00* | (2006.01) | |
| *C07J 7/00* | (2006.01) | |
| *C07J 13/00* | (2006.01) | |
| *C07J 41/00* | (2006.01) | |
| *C07J 71/00* | (2006.01) | |

(52) U.S. Cl.
CPC ............ *C07J 9/005* (2013.01); *C07J 1/0011* (2013.01); *C07J 7/0035* (2013.01); *C07J 13/005* (2013.01); *C07J 13/007* (2013.01); *C07J 41/0005* (2013.01); *C07J 41/005* (2013.01); *C07J 71/0005* (2013.01)

(58) Field of Classification Search
CPC .... C07J 71/0005; C07J 41/005; C07J 1/0011; C07J 13/005; C07J 7/0035; C07J 13/007
See application file for complete search history.

(56) References Cited

U.S. PATENT DOCUMENTS

| | | |
|---|---|---|
| 4,360,470 A | 11/1982 | Batcho et al. |
| 2008/0318870 A1 | 12/2008 | Moriarty et al. |
| 2013/0261317 A1* | 10/2013 | Moriarty ............... A61K 45/06 549/334 |

FOREIGN PATENT DOCUMENTS

| | | | |
|---|---|---|---|
| CN | 103145784 A | 6/2013 | |
| WO | WO 2008/130449 A2 | 10/2008 | |
| WO | WO-2008130449 A2 * | 10/2008 | ............ C07J 1/0011 |
| WO | WO 2008/157635 A2 | 12/2008 | |
| WO | WO 2014/160441 A1 | 10/2014 | |

OTHER PUBLICATIONS

Camacho et al, Ciencia (Maracaibo, Venezuela), Chemical constituents of some bioactive fractions of the non-polar extract from the *Caribbean octocoral Muricea* sp. identified by GC/MS, 2011 , 19 (4) , 285-292, Abstract only. (Year: 2011).*
Giacopello S. et al. "Synthesis and NMR Studies of Some Steroidal Isoxazoles", Zeitschrift fuer Naturforschung, 1992, vol. 47b, p. 891-897.
Gioiello A. et al. "Patented TGR5 modulators: a review (2006-present)", Expert Opinion on Therapeutic Patents, 2012, vol. 22, No. 12, p. 1399-1414.
Gioiello A. et al. "Bile Acid Derivatives as Ligands of the Farnesoid X Receptor: Molecular Determinants for Bile Acid Binding and Receptor Modulation", Current Topics in Medicinal Chemistry, 2014, vol. 14, p. 2159-2174.
Hershberg E. et al. "Selective Reduction and Hydrogenation of Unsaturated Steroids", JACS, 1951, vol. 73, p. 5073-5076.
Kawamata J. et al., "A G Protein-coupled Receptor Responsive to Bile Acids", The Journal of Biological Chemistry, 2003, vol. 278, p. 9435-9440.
Nuklear "File: Marker Degradation" Create Date: May 25, 2015 https://commons.wikimedia.org/wiki/File:Marker_Degradation. svg; 2 pages.

(Continued)

*Primary Examiner* — Paul A Zucker

(74) *Attorney, Agent, or Firm* — Michelle Iwamoto-Fan; Intercept Pharmaceuticals, Inc

(57) ABSTRACT

The present application relates to a method of preparing compounds of Formula (I) or a pharmaceutically acceptable salt, solvate, or amino acid conjugate thereof, $R_1$ is H, α-OH, β-OH, or an oxo group.

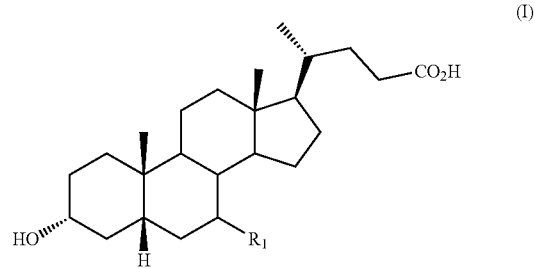

20 Claims, No Drawings

(56) References Cited

OTHER PUBLICATIONS

Pellicciari R. et al. "Nongenomic actions of bile acids. Synthesis and preliminary characterization of 23- and 6,23-alkyl-substituted bile acid derivatives as selective modulators for the G-protein coupled receptor TGR5", J. Med. Chem., 2007, vol. 50, No. 18, p. 4265-4268.

Pellicciari R. et al. "Discovery of 6r-Ethyl-23(S)-methylcholic Acid (S-EMCA, INT-777) as a Potent and Selective Agonist for the TGR5 Receptor, a Novel Target for Diabesity", J. Med. Chem., 2009, vol. 52, p. 7958-7961.

Pubchem CID 4598707, Create Date: Sep. 16, 2005, Date Accessed: Sep. 13, 2016, p. 3.

St'Astna et al. "Stereoselectivity of sodium borohydride reduction of saturated steroidal ketones utilizing conditions of Luche reduction" Steroids, 2010, vol. 75, p. 721-725.

Balssa F., "Easy stereoselective synthesis of 5α-estrane-3Oβ, 17α-diol, the major metabolite of nandrolone in the horse", Steroids, 2011, vol. 76, p. 667-668.

Batcho A.D., et al. "Stereoselective introduction of steroid side chains at C(17) and C(20)", Helvetica Chimica Acta, 1981, vol. 64, No. 5, p. 1682-1687.

Boruah R. C., et al. "Synthesis of beta-formylsteroidal enamides and their conversion into geminal dichlorides" Indian Journal of Chemistry, 1999, vol. 38B, p. 274-282.

Chowdhury P, et al. "A simple efficient process for the synthesis of 16-Dehydropregnenolone Acetate (16-DPA)—a key steroid drug intermediate from diosgenin", Journal of Chemical Engineering & Process Technology, 2011, vol. 2. 7 pages.

Cuong, N.X. and Dan, N.V., "Synthesis of dehydroepiandrosterone (DHA) from 16-dehydropregnenolone acetate (DPA)", Tap Chi Duoc Hoc, 1983, vol. 4, 1 page.

Garrido M., et al. "Biological evaluation of androstene derivatives", Arch. Pharm Chem. Life Sci., 2013, vol. 346, No. 1, p. 62-70.

Goswami A., et al. "A one-pot efficient process for 16-dehydropregnenolone acetate", Organic Process Research & Development 2003, vol. 7, No. 3, p. 306-308.

Kaur S. et al. "A Facile Route for the Synthesis of Bisquartenary Azazsteroids", International Journal of Pharmacy and Pharmaceutical Sciences, 2013, vol. 5, Suppl. 2, p. 728-732.

Tang J.J., et al. "Synthesis and cytotoxicity of novel steroidal C-20 oxime ester derivatives from 16-DPA", Arabian Journal of Chemistry, 2015, 7 pages.

Wovkulich, P. M. et al. "Stereoselective Introduction of Steroid Side Chains. Synthesis of Chenodeoxycholic Acid", Helvetica Chimica Acta, 1984, vol. 67, No. 2, p. 612-615.

\* cited by examiner

METHODS FOR PREPARATION OF BILE ACIDS AND DERIVATIVES THEREOF

BACKGROUND

Bile acids and bile acid derivatives are useful in the treatment and prevention of diseases. Bile acids have been shown to induce internalization of the TGR5 fusion protein from the cell membrane to the cytoplasm (Kawamata et al., 2003, J. Biol. Chem. 278, 9435). TGR5 is associated with the intracellular accumulation of cAMP and is an attractive target for the treatment of diseases (e.g., obesity, diabetes and metabolic syndrome). Numerous bile acid derivatives are TGR5 agonists, capable of regulating TGR5-mediated diseases and conditions. For example, 23-alkyl-substituted and 6,23-dialkyl-substituted derivatives of chenodeoxycholic acid (CDCA), such as 6α-ethyl-23(S)-methyl-chenodeoxycholic acid, have been reported as potent and selective agonists of TGR5 (Gioiello, et al., 2012, Exp. Opin. Ther. Pat. 22, 1399, Pellicciari, et al., 2007, J. Med. Chem. 50, 4265, and Pellicciari, et al., 2009, J. Med. Chem. 52, 7958).

Additionally, a number of bile acid derivatives are Farnesoid X receptor (FXR) agonists, and are able to regulate FXR-mediated diseases and conditions (Gioiello, et al., 2014 Curr. Top. Med. Chem. 14, 2159). FXR is a nuclear receptor that functions as a bile acid sensor controlling bile acid homeostasis. FXR is expressed in various organs and shown to be involved in many diseases and conditions, such as liver diseases, lung diseases, renal diseases, intestinal diseases, and heart diseases, and biological processes, including glucose metabolism, insulin metabolism, and lipid metabolism.

Bile acids are often isolated from mammalian and microbial organisms that naturally produce them. However, bile acids isolated from such organisms may contain toxins and contaminants. Moreover, methods of preparing bile acid derivatives by using microorganisms can lead to contamination of the final product. Thus, there are needs for synthetic methods of producing bile acids free of all moieties of animal origin and of pyrogenic moieties. The present application addresses these needs.

SUMMARY

The present application relates to a method of preparing a compound of Formula (I):

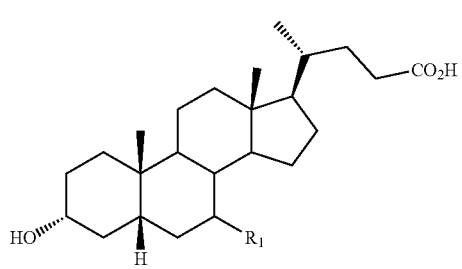

(I)

or a pharmaceutically acceptable salt, solvate, or amino acid conjugate thereof, wherein:

$R_1$ is H, α-OH, β-OH, or an oxo group, comprising the steps of:

(1) converting 2 to 3

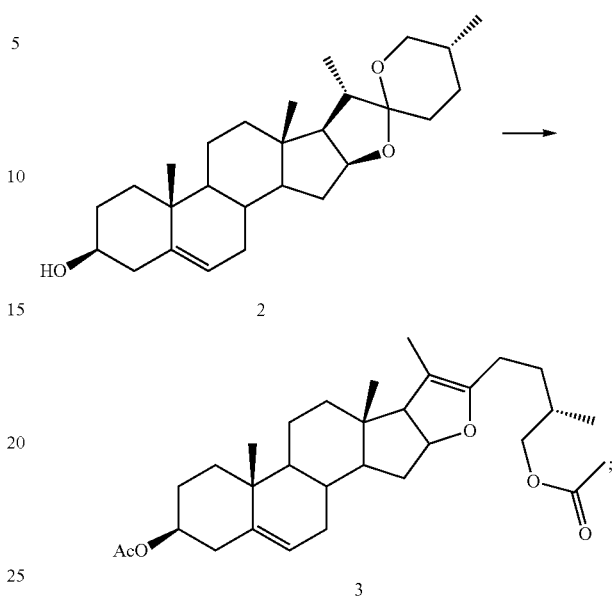

(2) selectively oxidizing 3 to yield 4

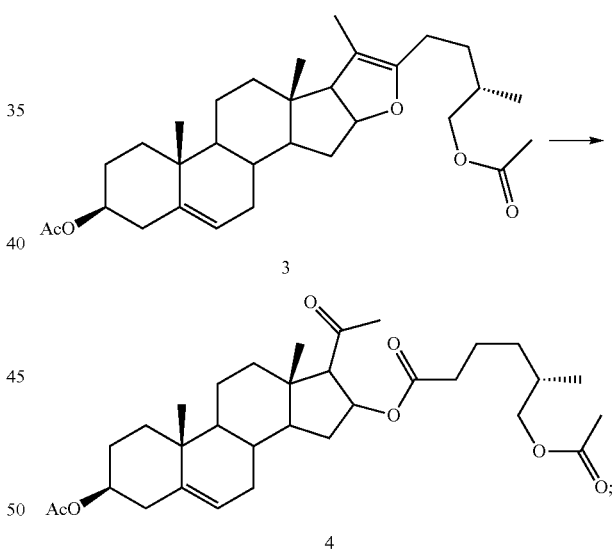

(3) converting 4 to 5

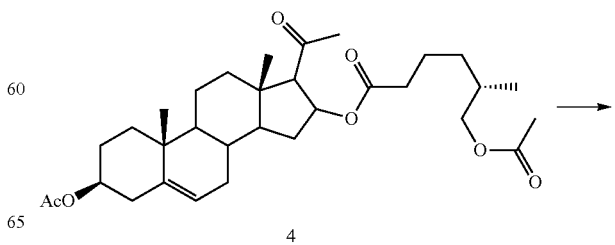

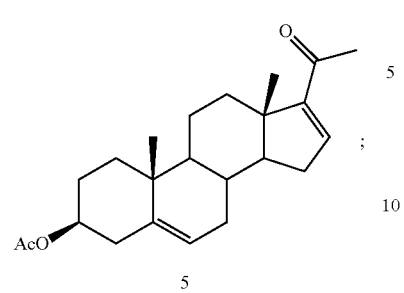
(4) converting 5 to oxime 6
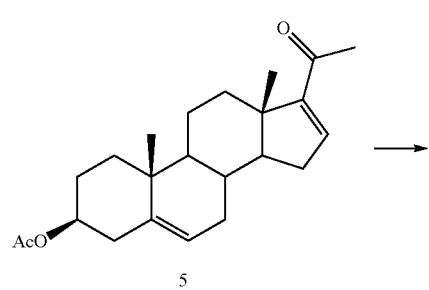
(5) converting oxime 6 to 7
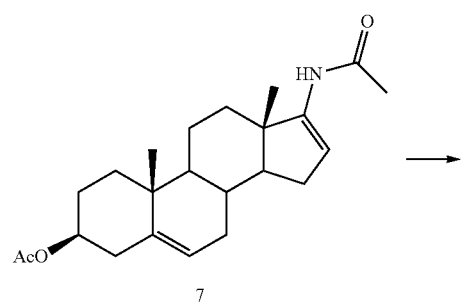
(6) converting 7 to ketone 8
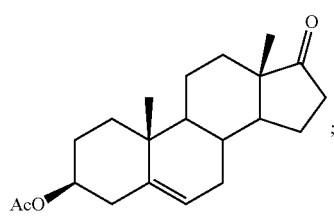
(7) deprotecting ketone 8 to form ketone 9;
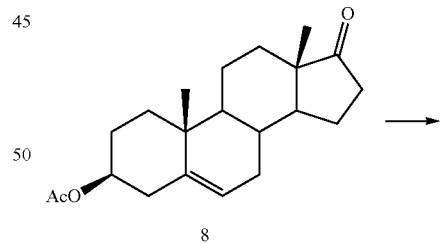
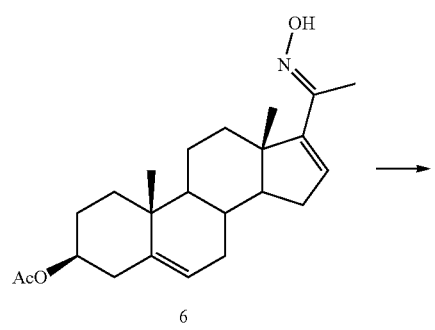
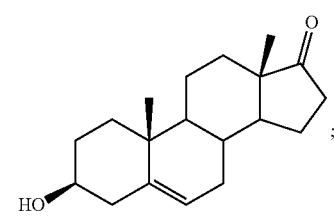

(8) olefinating 9 to yield 10

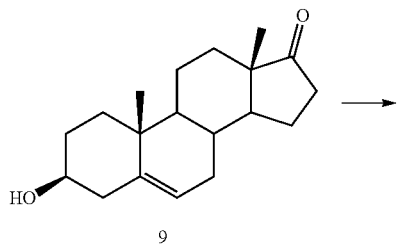

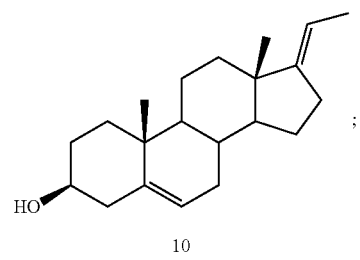

(9) alkylating olefin 10 regioselectively and stereoselectively to yield 11

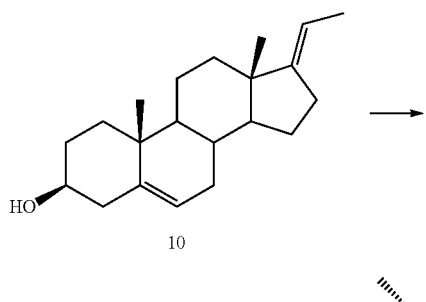

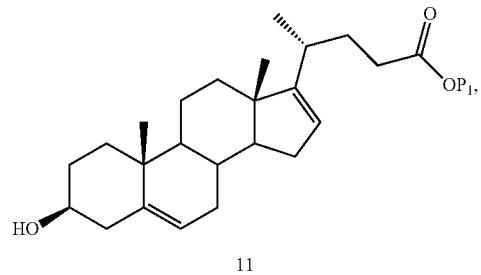

wherein $P_1$ is a protecting group or H;

(10) converting 11 to yield 12

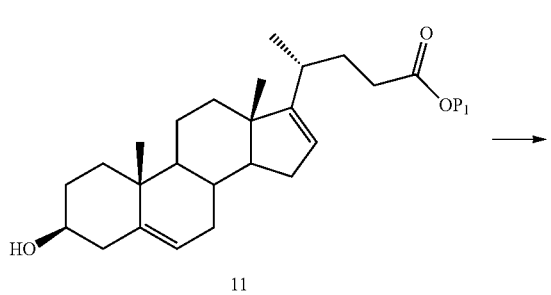

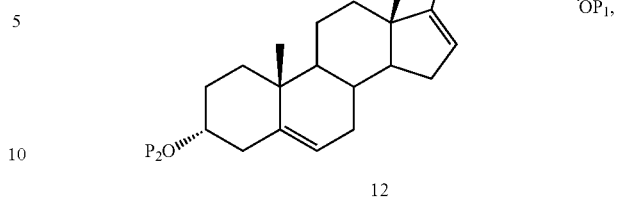

wherein $P_2$ is a protecting group;

(11) regioselectively and stereoselectively reducing 12 to yield 13

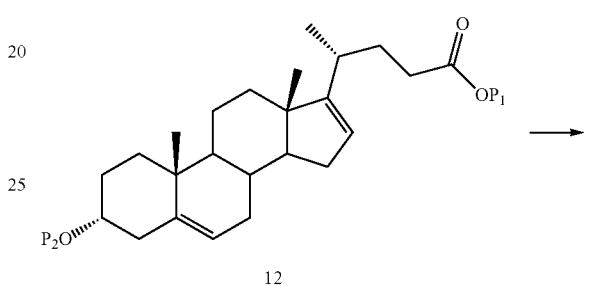

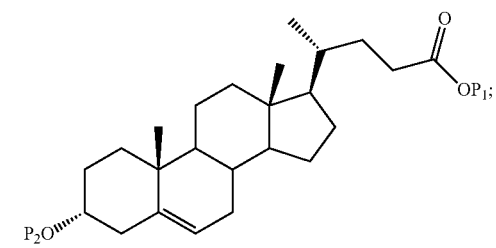

and

(12) deprotecting and selectively reducing 13 to yield the compound of formula (I).

In one embodiment, one or more steps in the processes described herein is conducted under flow chemistry conditions. In other embodiments, one or more steps in the processes of the invention is conducted under microwave conditions.

In one aspect, the present application is directed to a process for preparing a compound of Formula (Ia):

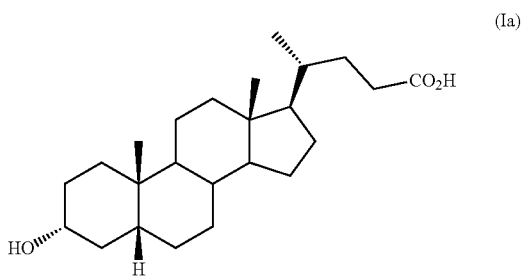 [SMILES: C[C@H](CCC(=O)O)[C@H]1CCC2C3CC[C@@H]4C[C@H](O)CC[C@]4(C)C3CC[C@@]21C]

or a pharmaceutically acceptable salt, solvate, or amino acid conjugate thereof, comprising the steps of:

(1) stereoselectively reducing 13 to yield 14

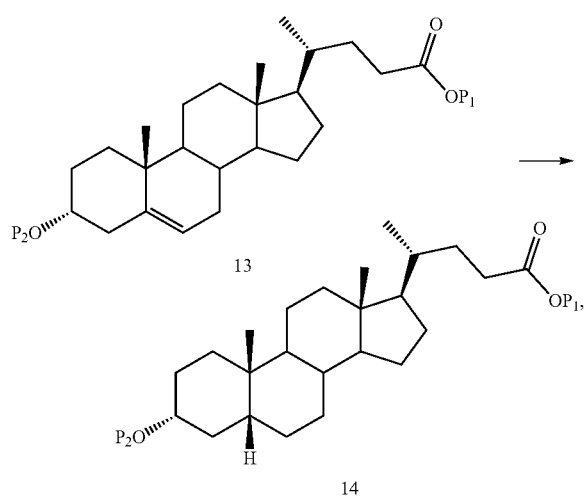

wherein $P_1$ is H or a protecting group and $P_2$ is a protecting group;

(2) selectively deprotecting 14 to yield 14a

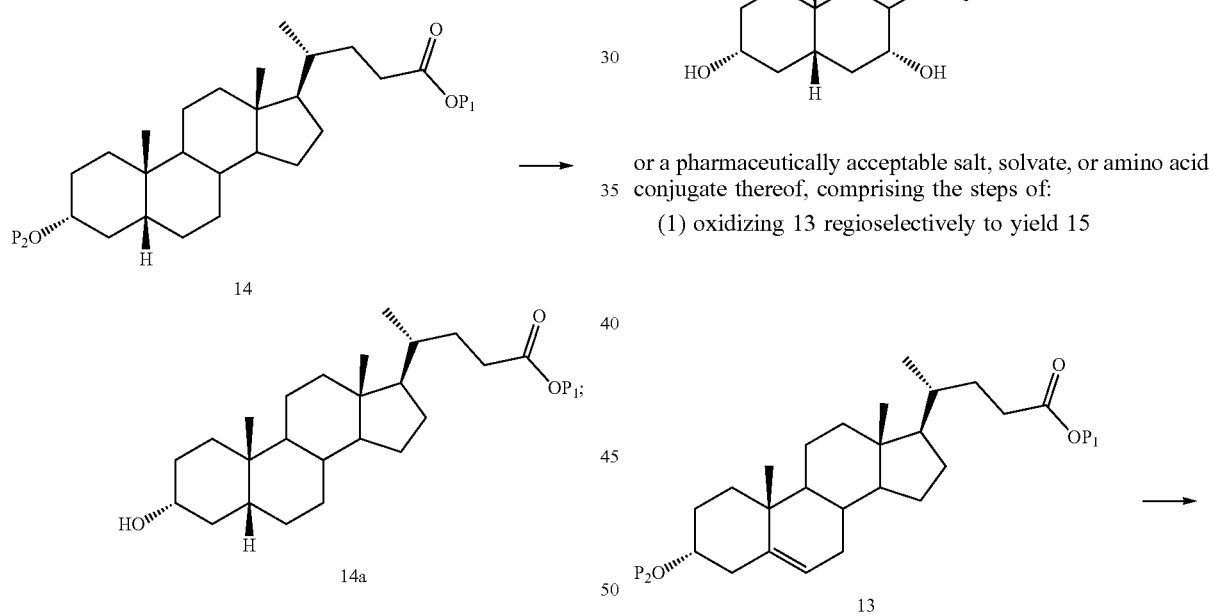

and (3) hydrolyzing 14a to form the compound of Formula (Ia)

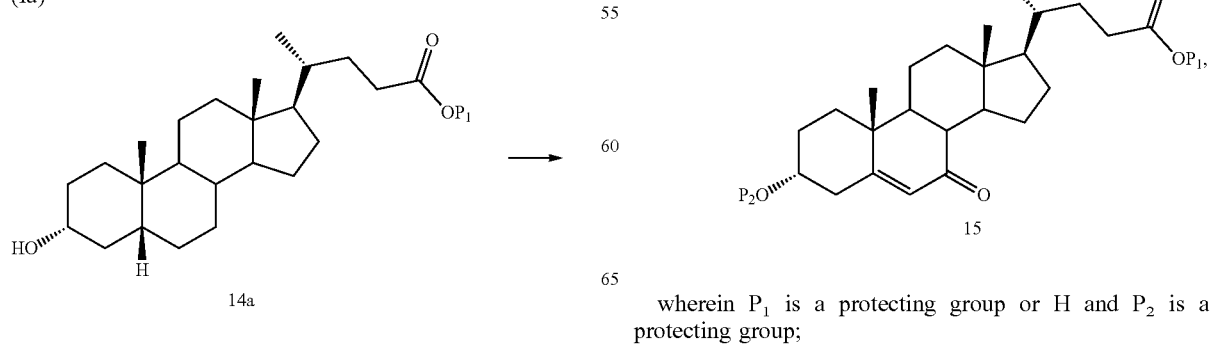

In some embodiments, the deprotecting in step 2 and the hydrolyzing in step 3 may occur in a single step.

In one aspect, the present application is directed to a process for preparing a compound of Formula (Ib);

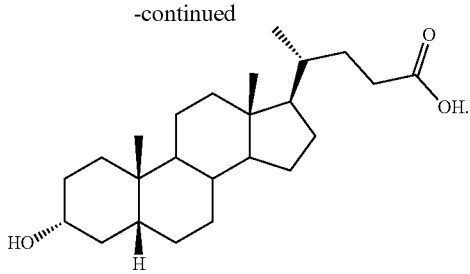

or a pharmaceutically acceptable salt, solvate, or amino acid conjugate thereof, comprising the steps of:

(1) oxidizing 13 regioselectively to yield 15 wherein $P_1$ is a protecting group or H and $P_2$ is a protecting group;

(2) stereoselectively reducing 15 to yield 16A

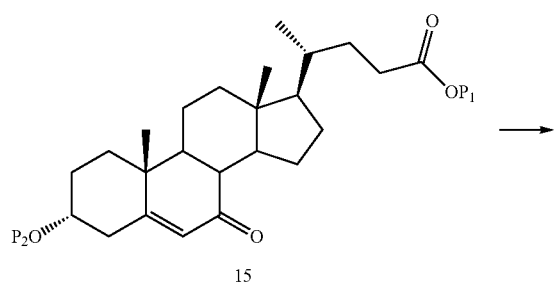

15

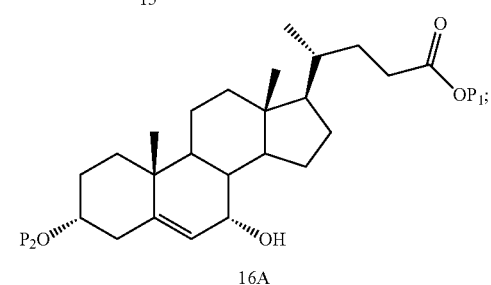

16A (3) stereoselectively reducing 16A to yield 17

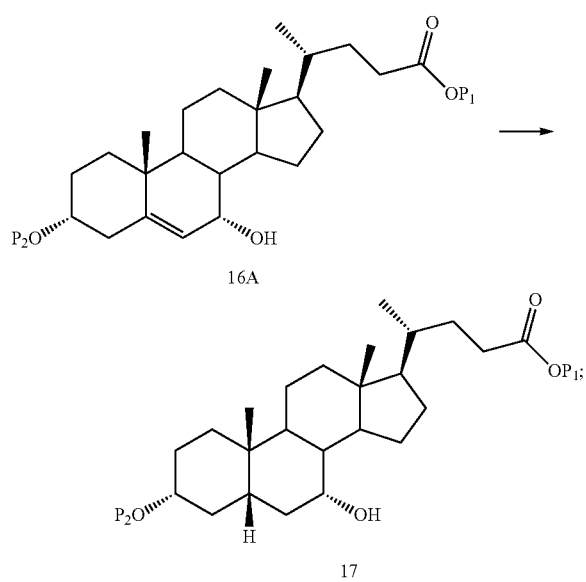

16A

17

(4) selectively deprotecting 17 to yield 17A

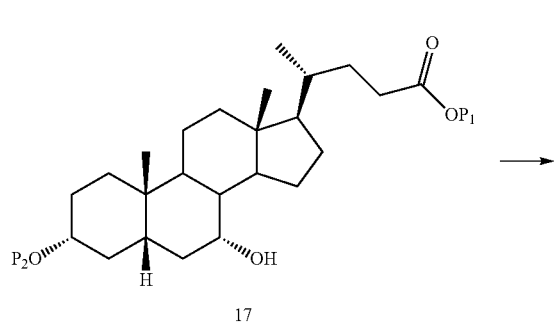

17

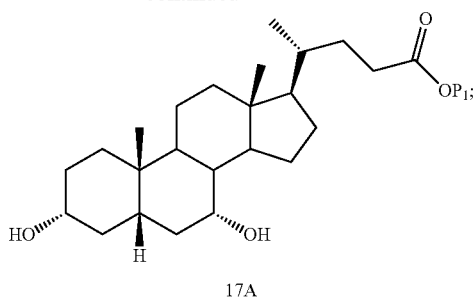

17A and (5) hydrolyzing 17A to yield the compound of Formula (Ib)

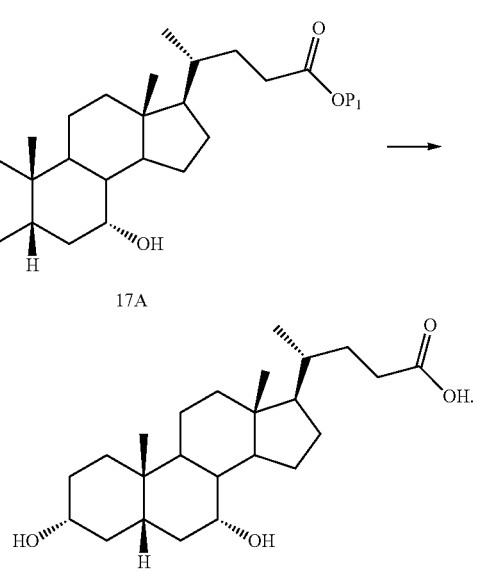

17A

In some embodiments of the process, the deprotecting in step 4 and the hydrolyzing in step 5 occur in a single step, where 17 and 17A are simultaneously deprotected.

In one aspect, the present application is directed to a process for preparing a compound of Formula (Ic):

(Ic)

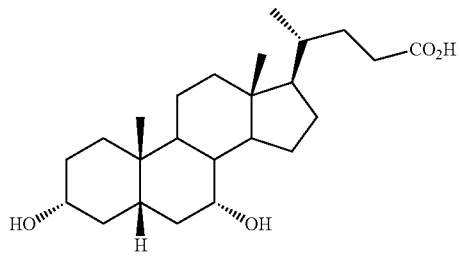

or a pharmaceutically acceptable salt, solvate, or amino acid conjugate thereof, comprising the steps of:

(1) oxidizing 13 to regioselectively yield 15
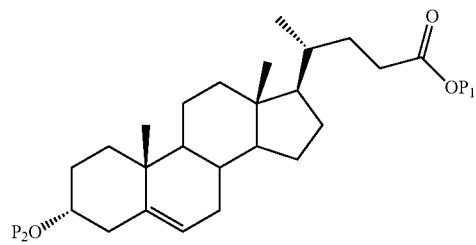
13
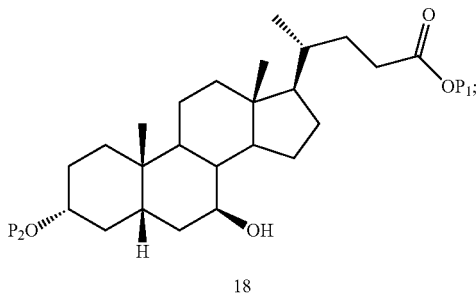
18
(4) deprotecting 18 to yield 18A
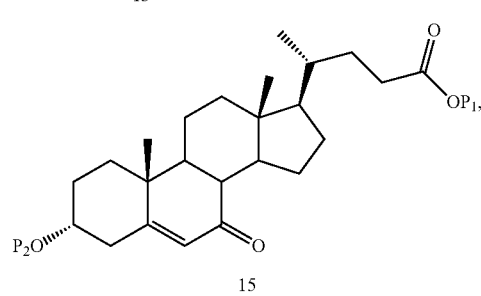
15
wherein $P_1$ is a protecting group or H and $P_2$ is a protecting group;
(2) stereoselectively reducing 15 to yield 16B
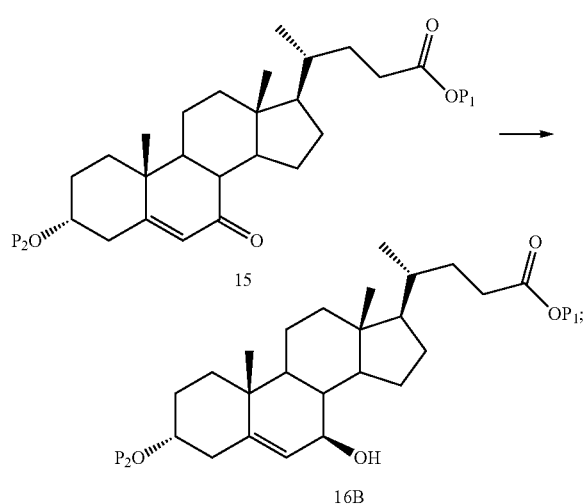
15
16B
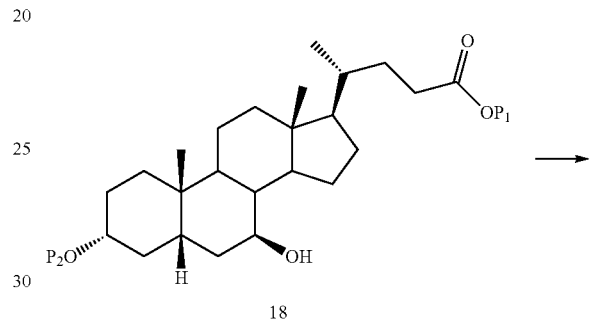
18
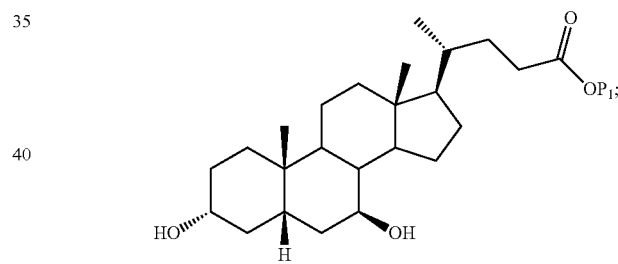
18A
and
(5) hydrolyzing 18A to yield the compound of Formula (Ic)
(3) stereoselectively reducing 16B to yield 18
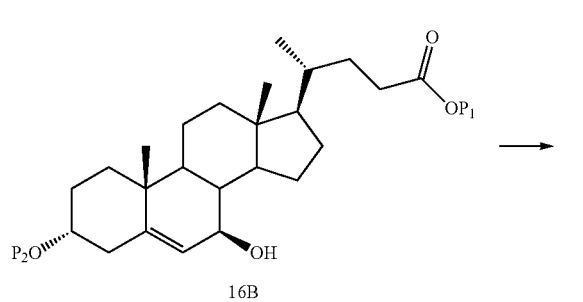
16B
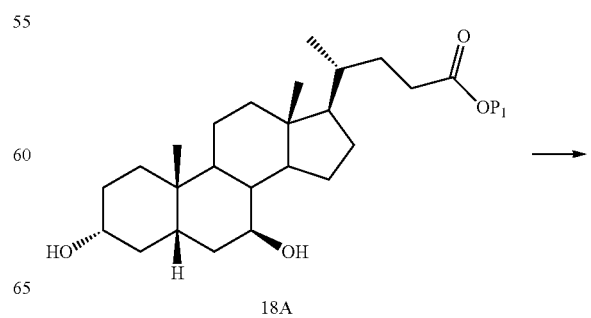
18A -continued

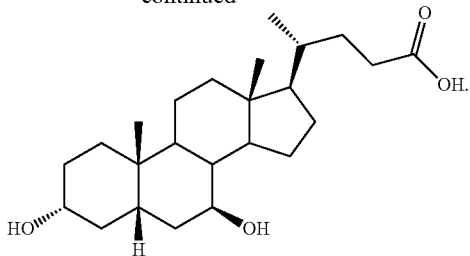

In some embodiments of the process, the deprotecting in step 4 and the hydrolyzing in step 5 occur in a single step, where 18 and 18A are simultaneously deprotected.

In one aspect, the present application is directed to a process for preparing a compound of Formula (I):

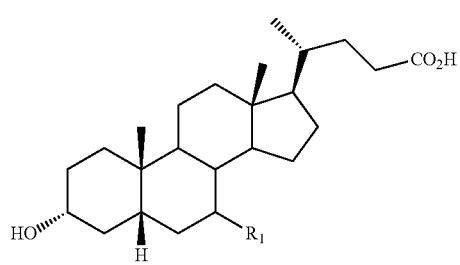

or a pharmaceutically acceptable salt, solvate, or amino acid conjugate thereof, wherein:

$R_1$ is H, α-OH, β-OH, or an oxo group, comprising the steps of:

stereoselectively reducing 13 to yield 14

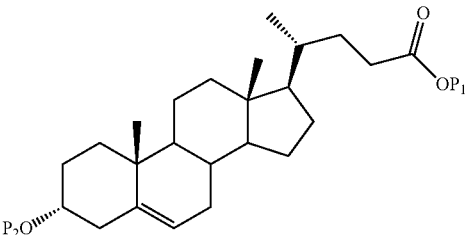

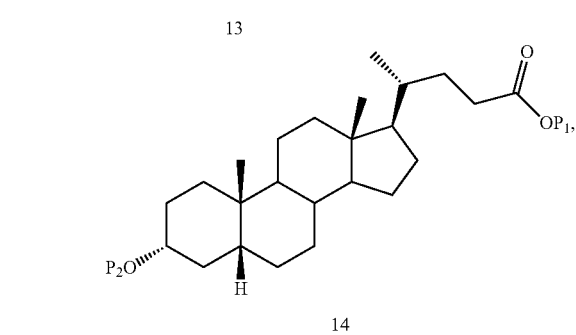

wherein $P_1$ is a protecting group or H and $P_2$ is a protecting group; and deprotecting 14 to yield the compound of formula (I).

In some embodiments, the stereoselective reduction comprises hydrogenation.

In some embodiments, the hydrogenation is conducted with a catalyst and hydrogen gas.

In some embodiments, the hydrogenation is conducted with a catalyst and syngas. In some embodiments, the hydrogenation may be also conducted under flow chemistry conditions, as described herein.

In one aspect, the present application is directed to a process for preparing a compound of Formula (I):

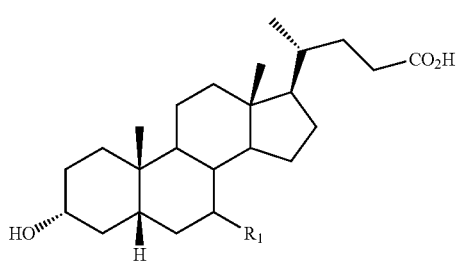

or a pharmaceutically acceptable salt, solvate, or amino acid conjugate thereof, wherein $R_1$ is α-OH, comprising the step of:

stereoselectively reducing 15 to yield 16A

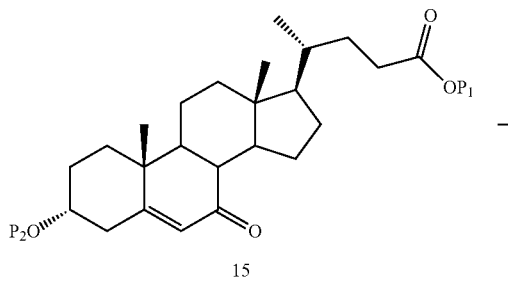

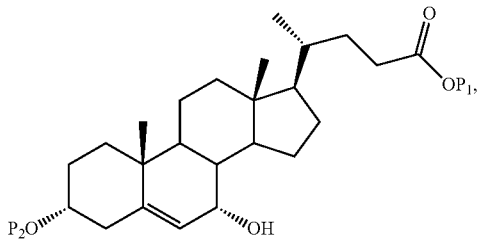

wherein $P_1$ is a protecting group or H and $P_2$ is a protecting group.

In some embodiments, the stereoselective reduction of 15 to 16A comprises reacting 15 with K-Selectride. In other embodiments, the stereoselective reduction of 15 to 16A may be carried out under flow chemistry conditions.

In one aspect, the present application is directed to a process for preparing a compound of Formula (I):

15

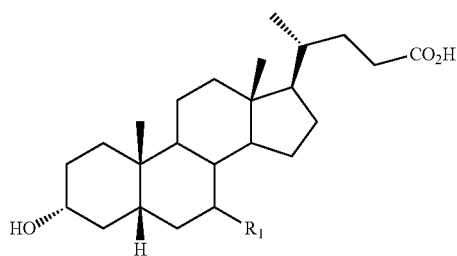

or a pharmaceutically acceptable salt, solvate, or amino acid conjugate thereof, wherein $R_1$ is α-OH, comprising the step of:

stereoselectively reducing 16A to yield 17

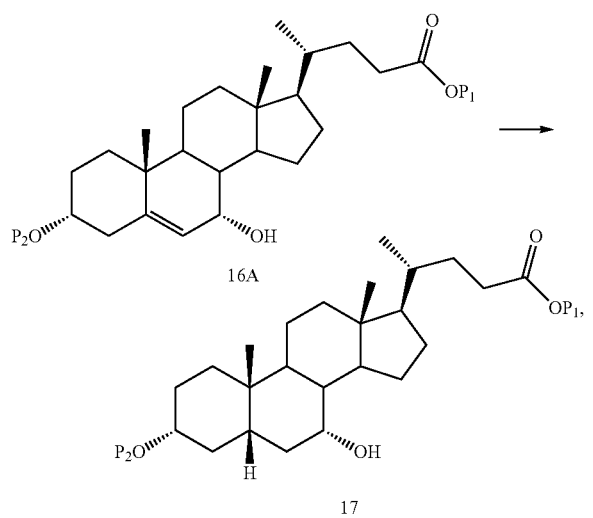

wherein $P_1$ is a protecting group or H and $P_2$ is a protecting group; and
deprotecting 17 to yield the compound of Formula (I) wherein $R_1$ is α-OH.

In some embodiments, the stereoselective reduction comprises hydrogenation.

In some embodiments, the hydrogenation is conducted with a catalyst and hydrogen gas.

In some embodiments, the hydrogenation is conducted with a catalyst and syngas. In some embodiments, the hydrogenation may also be conducted under flow chemistry conditions, as described herein.

In one aspect, the present application is directed to a process for preparing a compound of Formula (I):

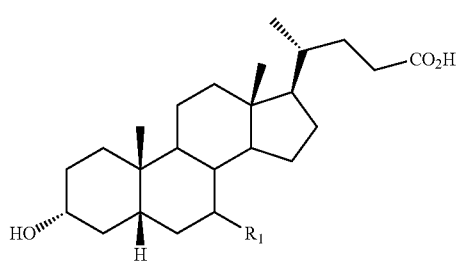

or a pharmaceutically acceptable salt, solvate, or amino acid conjugate thereof, wherein $R_1$ is α-OH, comprising the steps of:

16

(1) stereoselectively reducing 15 to yield 16A

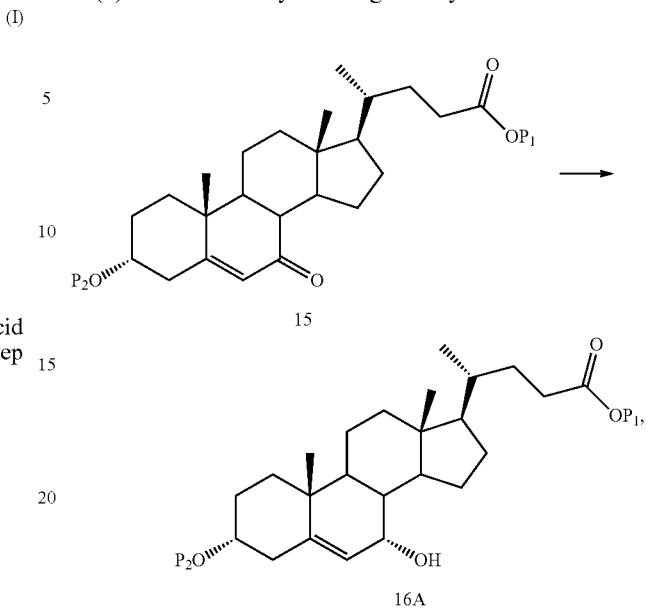

wherein $P_1$ is a protecting group or H and $P_2$ is a protecting group;
(2) stereoselectively reducing 16A to yield 17

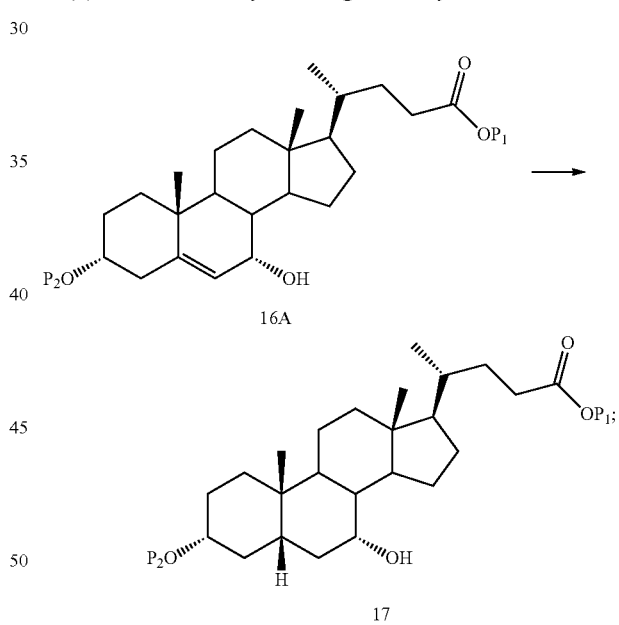

and
deprotecting 17 to yield the compound of Formula (I) wherein $R_1$ is α-OH.

In some embodiments, the stereoselective reduction of 15 to 16A comprises reacting 15 with K-Selectride.

In some embodiments, the stereoselective reduction of 16A to 17 comprises hydrogenation.

In some embodiments, the hydrogenation comprises reacting 16A with a catalyst and hydrogen gas.

In some embodiments, the hydrogenation is conducted with a catalyst and syngas.

Optionally, the hydrogenation may be conducted under flow chemistry conditions.

In one aspect, the present application is directed to a process for preparing a compound of Formula (I):

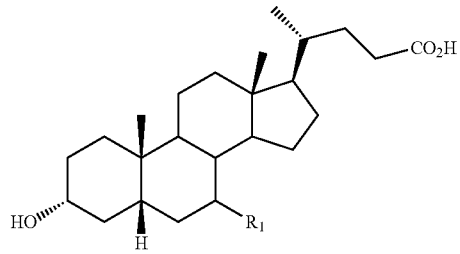
(I)

or a pharmaceutically acceptable salt, solvate, or amino acid conjugate thereof, wherein $R_1$ is α-OH, comprising the steps of:

(1) stereoselectively reducing 16A to yield 17

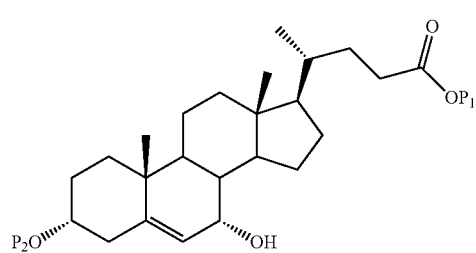

16A

17 wherein $P_1$ is a protecting group or H and $P_2$ is a protecting group;

(2) selectively deprotecting 17 to yield 17A

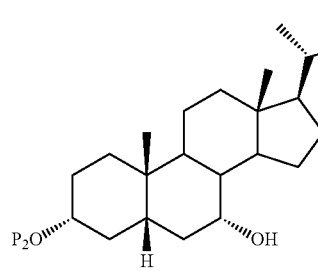

17

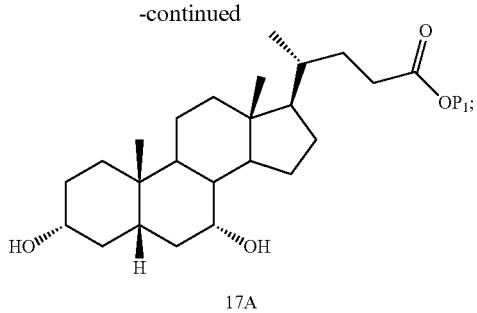

17A and (3) hydrolyzing 17A to yield a compound of Formula (I) wherein $R_1$ is α-OH

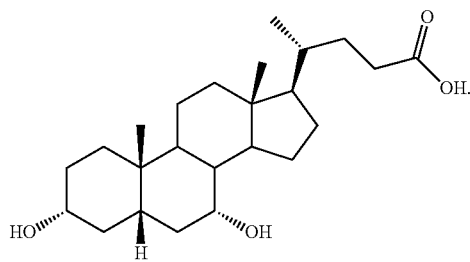

17A

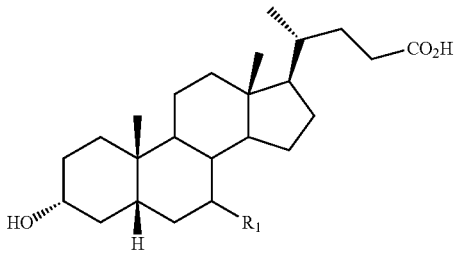

In one aspect, the present application is directed to a process for preparing a compound of Formula (I):

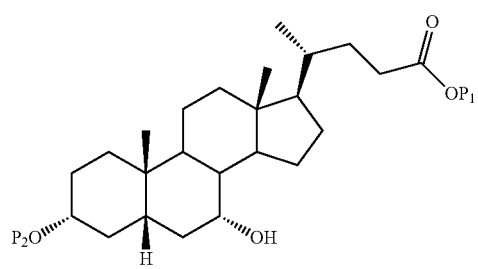
(I)

or a pharmaceutically acceptable salt, solvate, or amino acid conjugate thereof, wherein $R_1$ is β-OH, comprising the step of:

stereoselectively reducing 15 to yield 16B

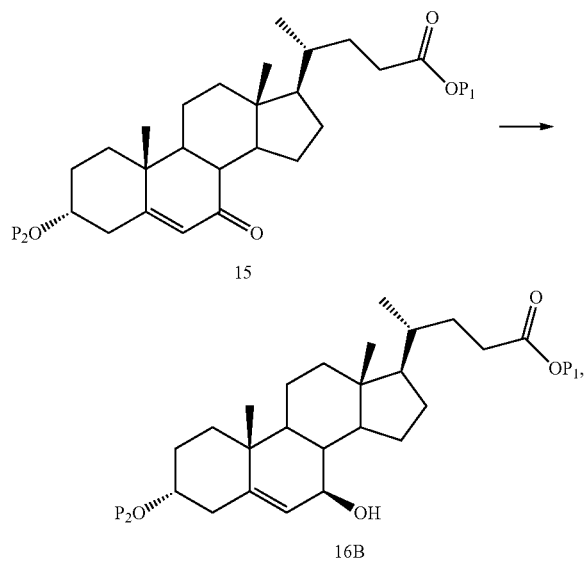

wherein P₁ is a protecting group or H and P₂ is a protecting group; and deprotecting 16B to yield the compound of Formula (I) wherein R₁ is β-OH.

In some embodiments, the stereoselective reduction of 15 to 16B comprises reacting 15 with NaBH₄ and CeCl₃.7H₂O.

In one aspect, the present application is directed to a process for preparing a compound of Formula (I):

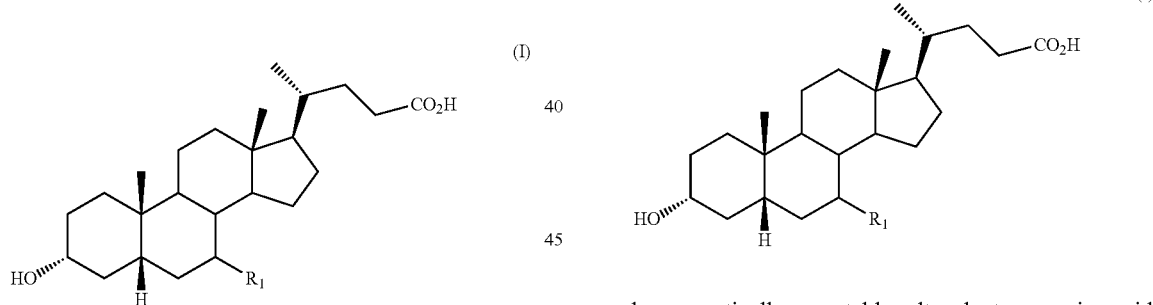

or a pharmaceutically acceptable salt, solvate, or amino acid conjugate thereof, wherein R₁ is β-OH, comprising the step of:

stereoselectively reducing 16B to yield 18

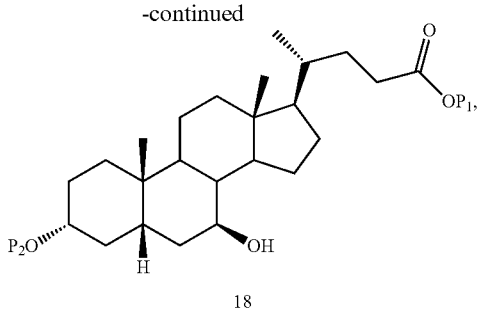

wherein P₁ is a protecting group or H and P₂ is a protecting group; and deprotecting 18 to yield the compound of Formula (I) wherein R₁ is β-OH.

In some embodiments, the stereoselective reduction comprises hydrogenation.

In some embodiments, the hydrogenation is conducted with a catalyst and hydrogen gas.

In some embodiments, the hydrogenation is conducted with a catalyst and syngas.

Optionally, the hydrogenation may be conducted under flow chemistry conditions.

In one aspect, the present application is directed to a process for preparing a compound of Formula (I):

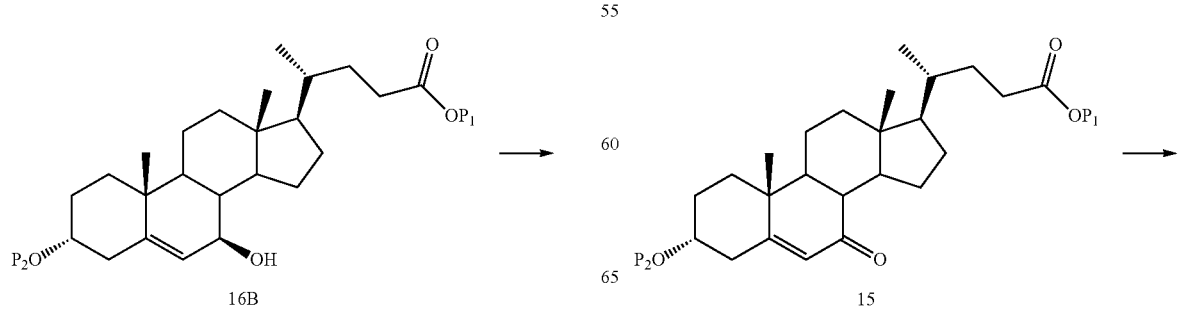

or a pharmaceutically acceptable salt, solvate, or amino acid conjugate thereof, wherein R₁ is β-OH, comprising the steps of:

(1) stereoselectively reducing 15 to yield 16B

-continued

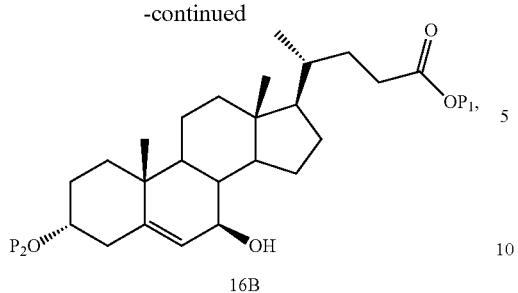
16B wherein P₁ is a protecting group or H and P₂ is a protecting group;

(2) stereoselectively reducing 16B to yield 18

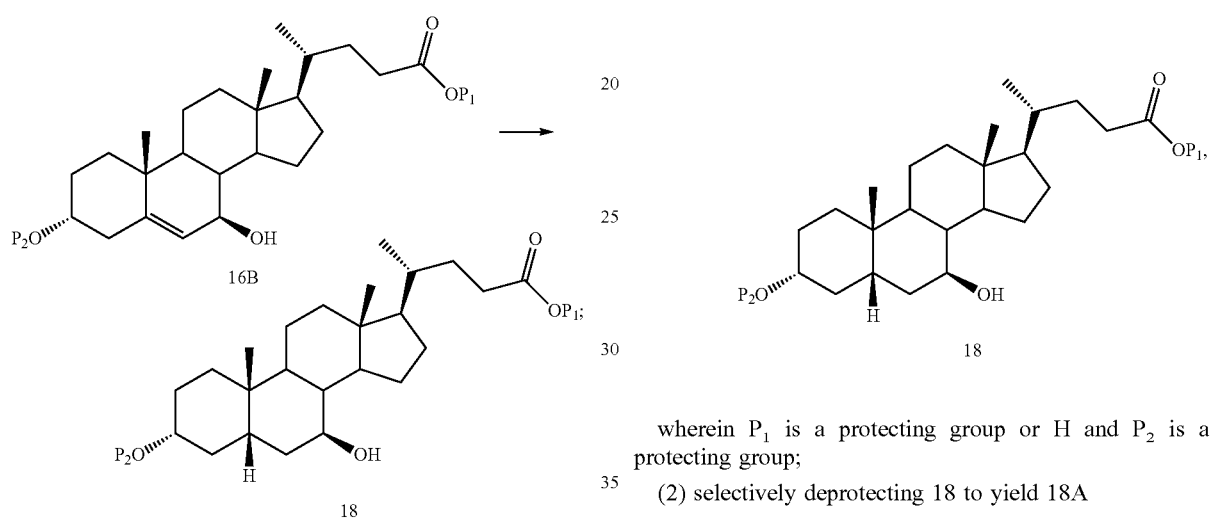

and
deprotecting 18 to yield the compound of Formula (I) wherein R₁ is β-OH.

In some embodiments, the stereoselective reduction of 15 to 16B comprises reacting 15 with NaBH₄ and CeCl₃·7H₂O.

In some embodiments, the stereoselective reduction of 16B to 18 comprises hydrogenation.

In some embodiments, the hydrogenation comprises reacting 16B with a catalyst and hydrogen gas.

In some embodiments, the hydrogenation is conducted with a catalyst and syngas.

Optionally, the hydrogenation steps may be carried out under flow chemistry conditions.

In one aspect, the present application is directed to a process for preparing a compound of Formula (I):

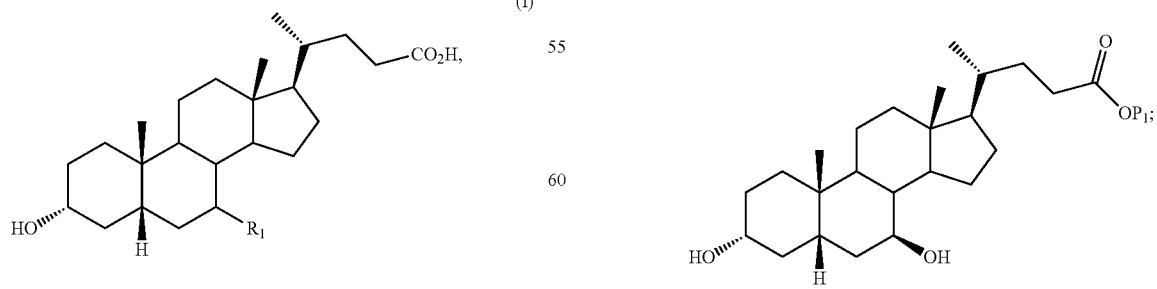

or a pharmaceutically acceptable salt, solvate, or amino acid conjugate thereof, wherein R₁ is β-OH, comprising the steps of:

(1) stereoselectively reducing 16B to yield 18

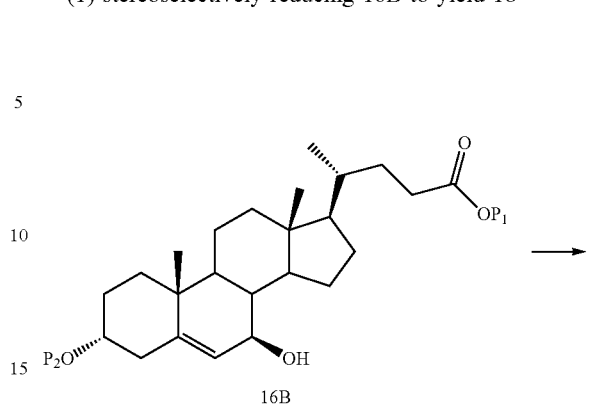

wherein P₁ is a protecting group or H and P₂ is a protecting group;

(2) selectively deprotecting 18 to yield 18A and
(3) converting 18A to yield a compound of Formula (I)
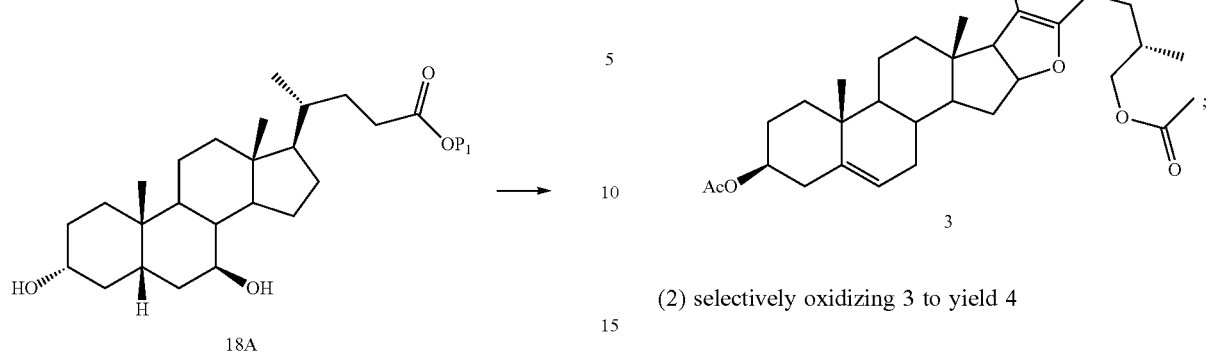
18A
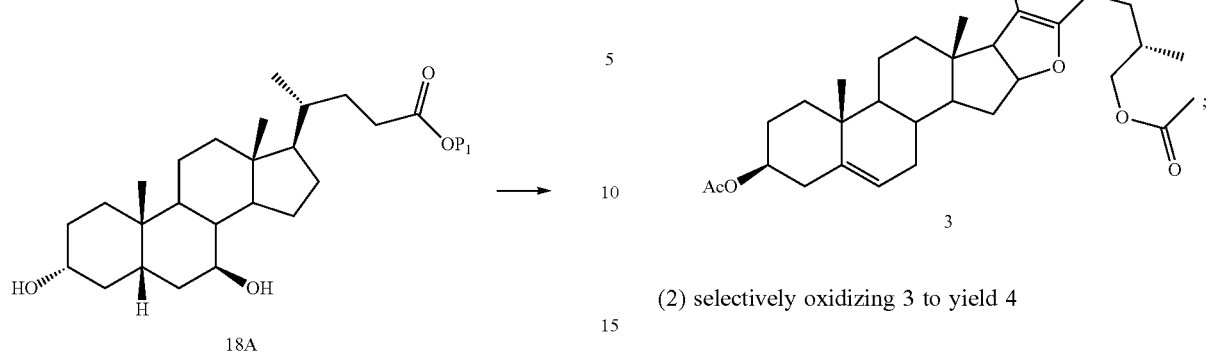
In one aspect, the present application is directed to a process for preparing a compound of Formula (I):
(I)
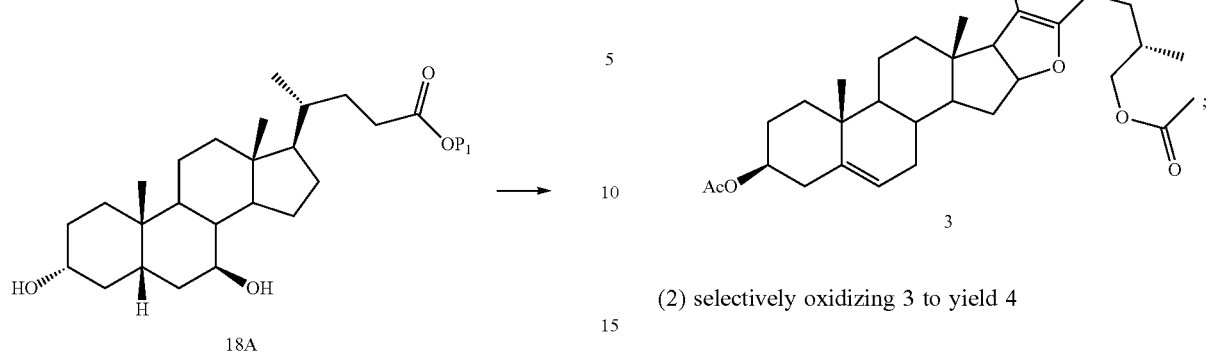
or a pharmaceutically acceptable salt, solvate, or amino acid conjugate thereof, wherein $R_1$ is H, comprising the steps of:
(1) converting 2 to 3
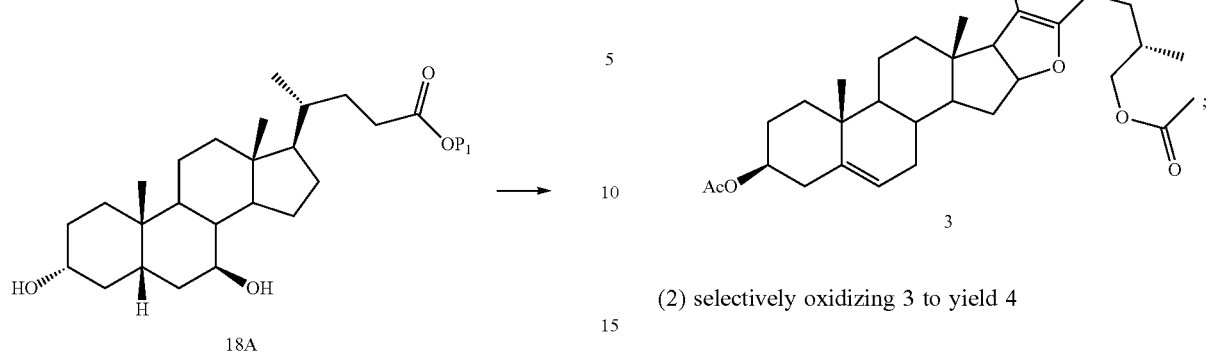
2
-continued
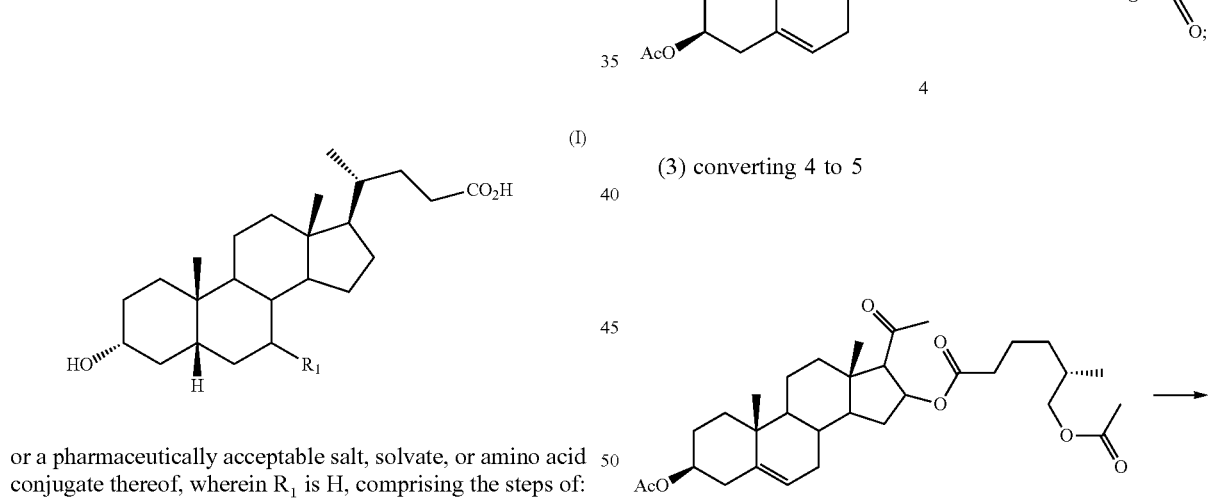
3
(2) selectively oxidizing 3 to yield 4
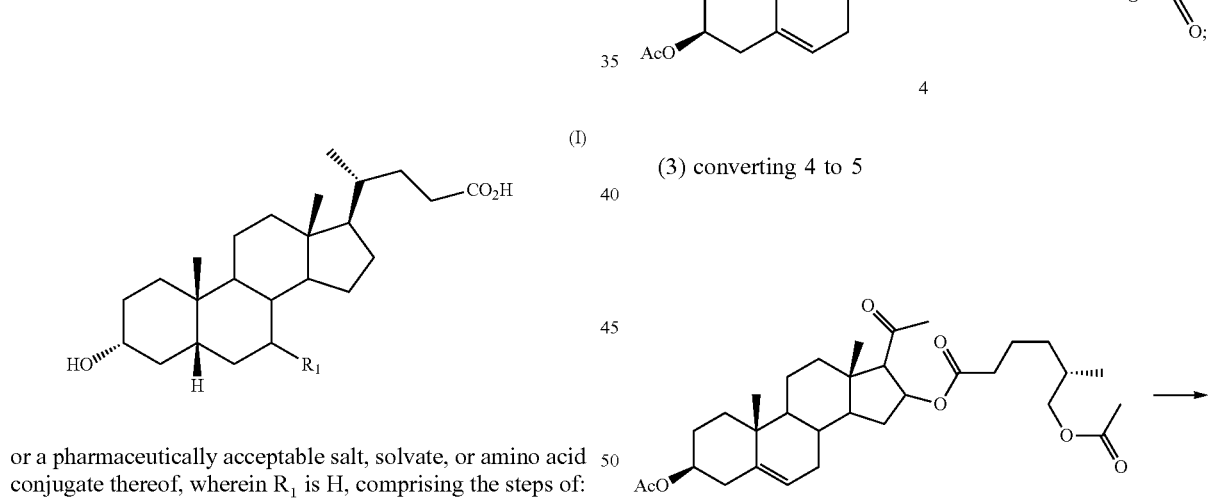
3
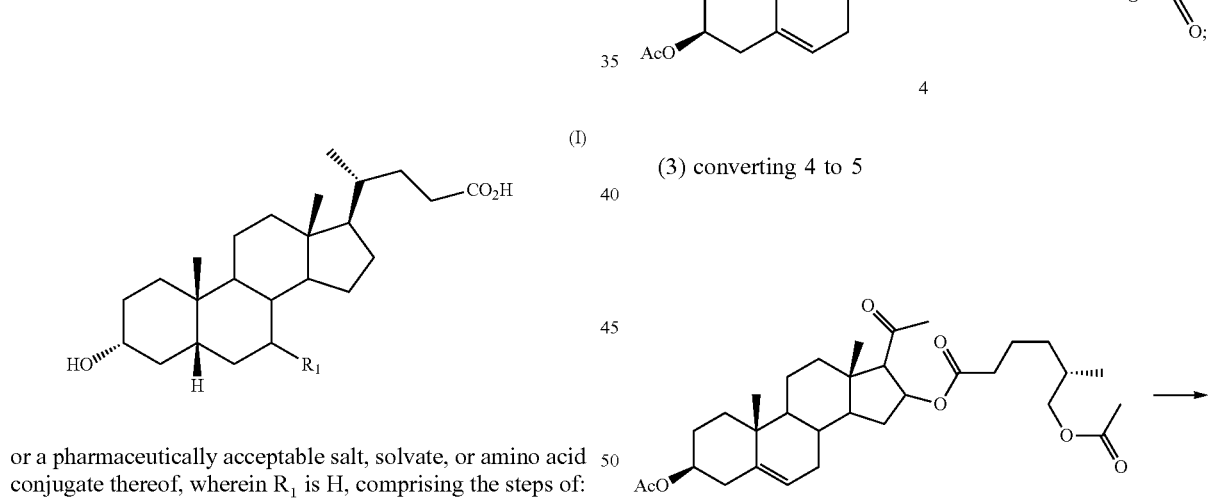
4
(3) converting 4 to 5
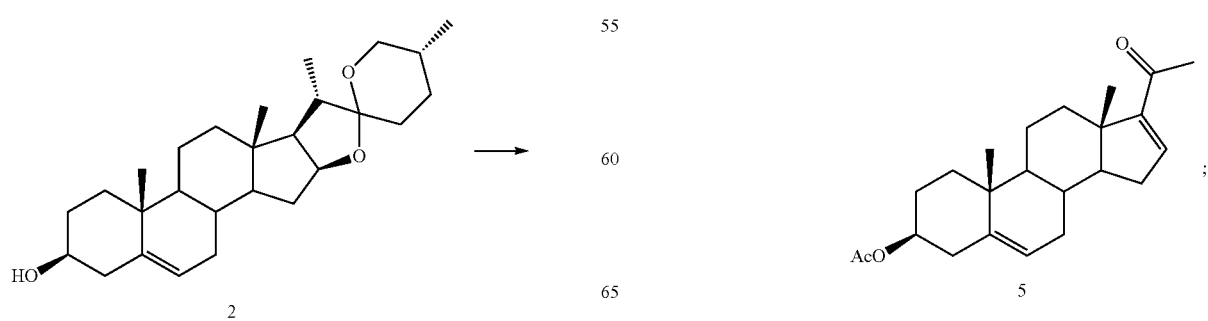
4
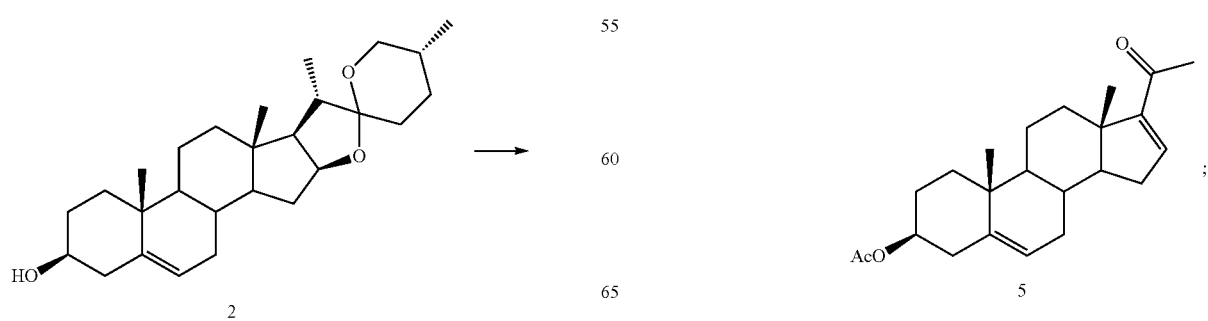
5

(4) converting 5 to oxime 6
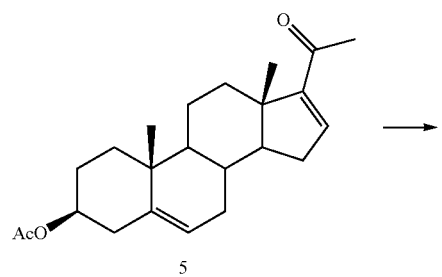
5
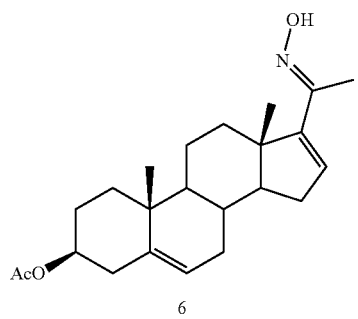
6
(5) converting oxime 6 to 7
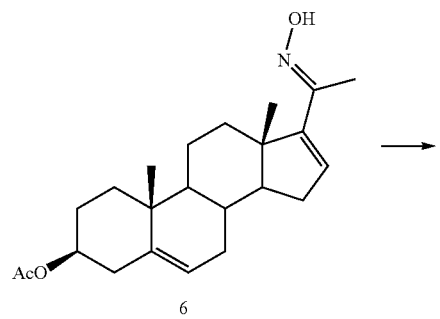
6
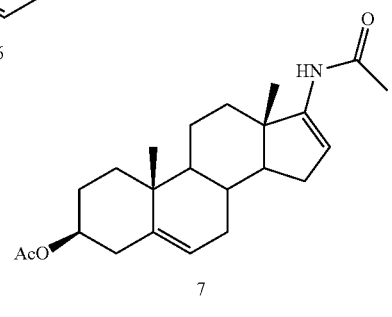
7
(6) converting 7 to ketone 8
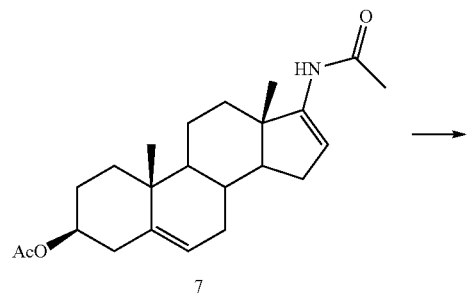
7
-continued
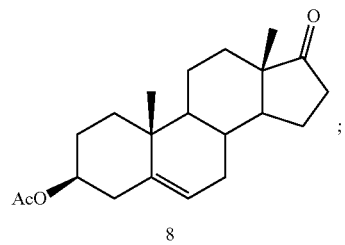
8
(7) deprotecting ketone 8 to form ketone 9;
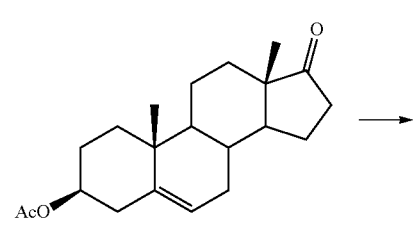
8
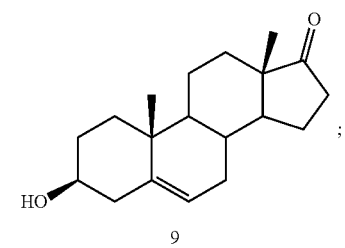
9
(8) olefinating 9 to yield 10
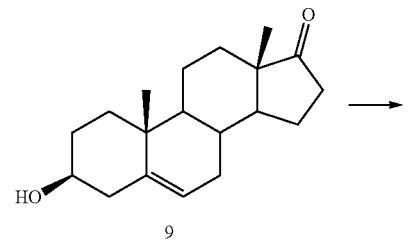
9
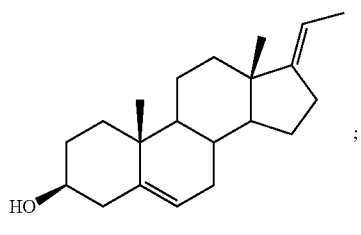
10

(9) alkylating olefin 10 regioselectively and stereoselectively to yield 11
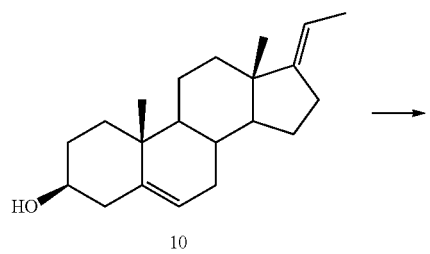
10
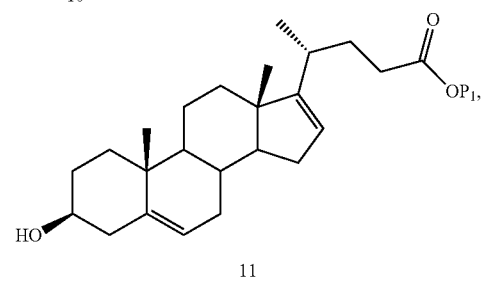
11
wherein $P_1$ is a protecting group or H;
(10) converting 11 to yield 12
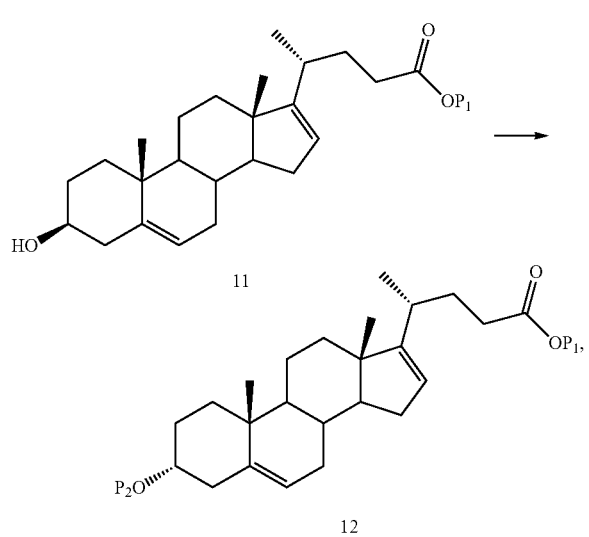
wherein $P_2$ is a protecting group;
(11) regioselectively and stereoselectively reducing 12 to yield 13
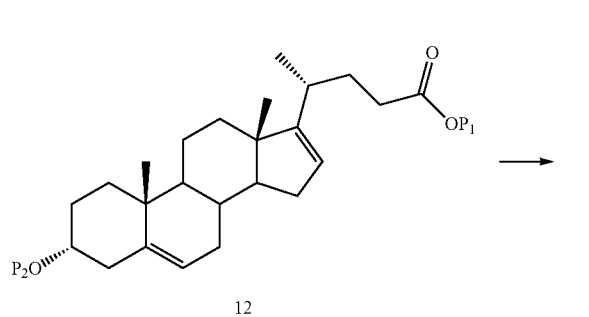
-continued
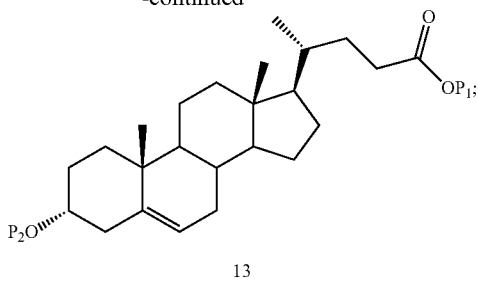
13
(12) stereoselectively reducing 13 to yield 14
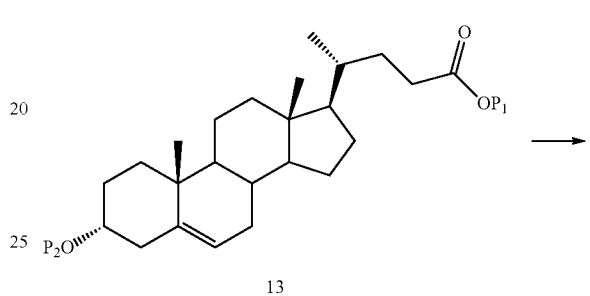
13
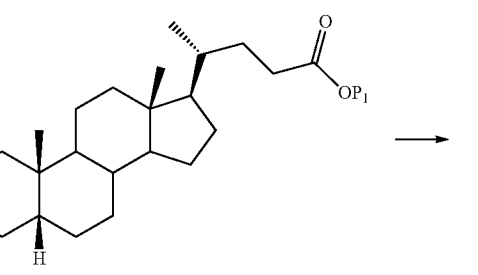
14
(13) selectively deprotecting 14 to yield 14a
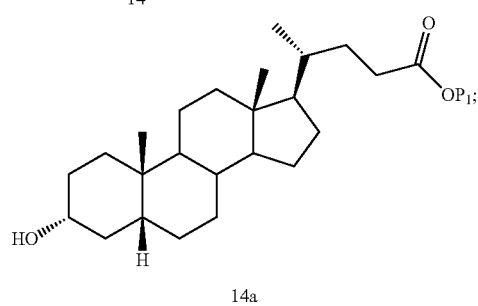
14a and
(14) hydrolyzing 14a to form a compound of Formula (I)
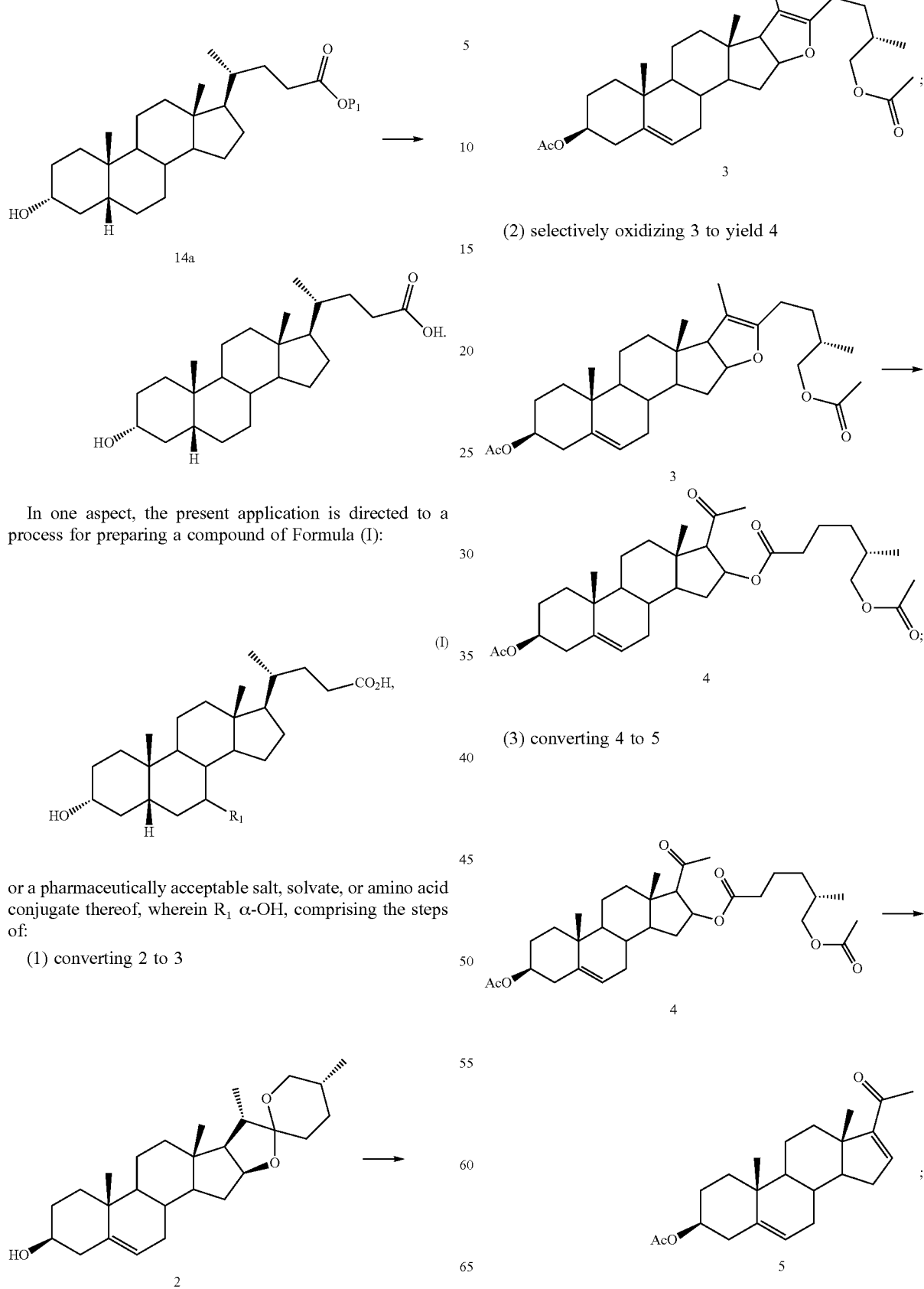
In one aspect, the present application is directed to a process for preparing a compound of Formula (I):
or a pharmaceutically acceptable salt, solvate, or amino acid conjugate thereof, wherein $R_1$ α-OH, comprising the steps of:
(1) converting 2 to 3
(2) selectively oxidizing 3 to yield 4
(3) converting 4 to 5

(4) converting 5 to oxime 6
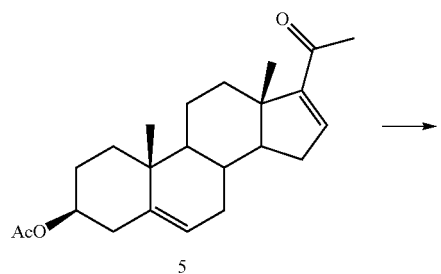
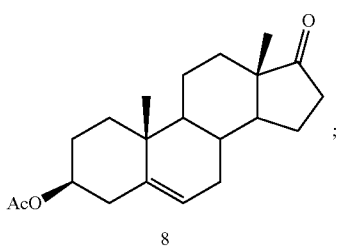
(7) deprotecting ketone 8 to form ketone 9;
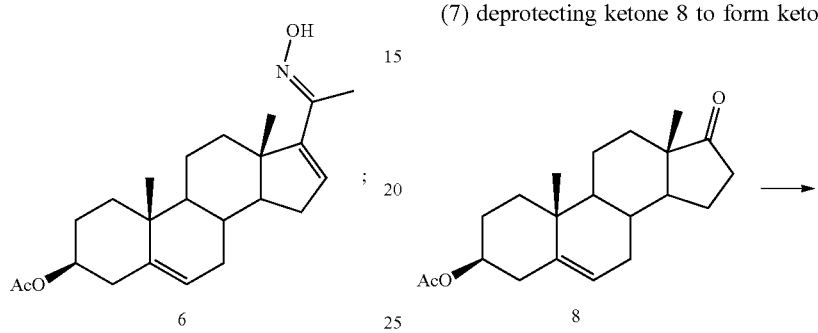
(5) converting oxime 6 to 7
(8) olefinating 9 to yield 10
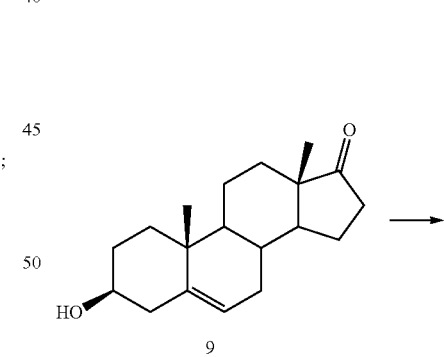
(6) converting 7 to ketone 8
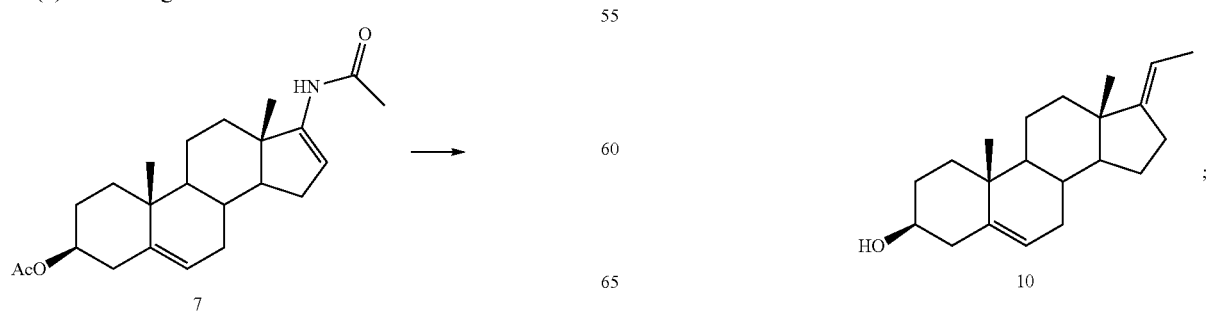

(9) alkylating olefin 10 regioselectively and stereoselectively to yield 11
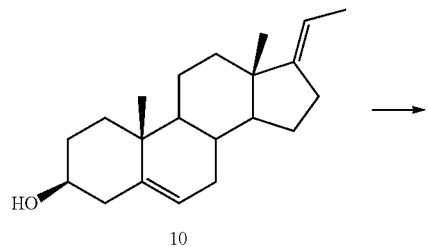
10
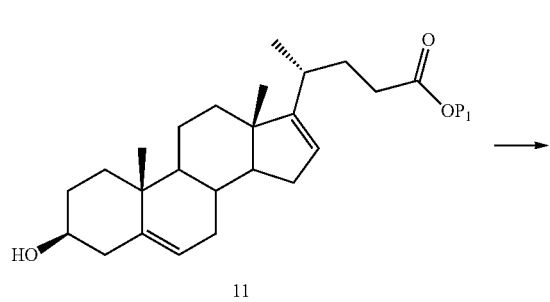
11
wherein $P_1$ is a protecting group or H;
(10) converting 11 to yield 12
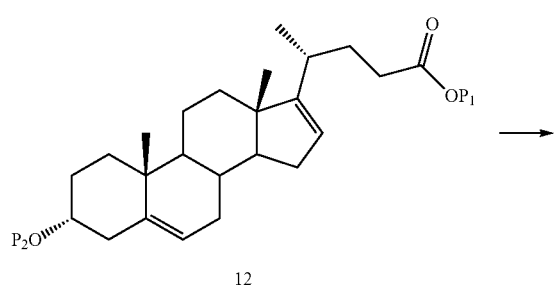
11
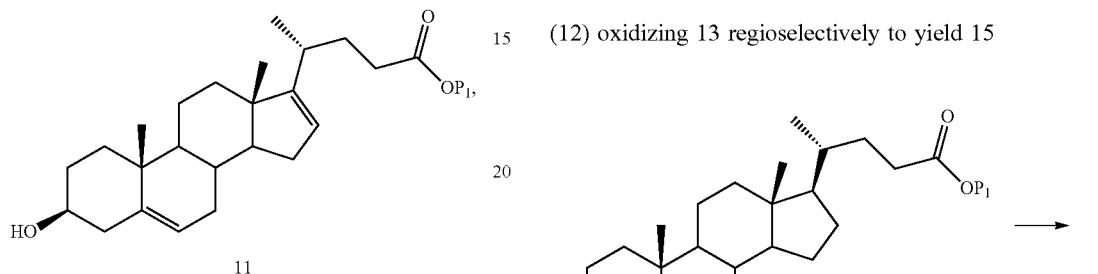
12
wherein $P_2$ is a protecting group;
(11) regioselectively and stereoselectively reducing 12 to yield 13
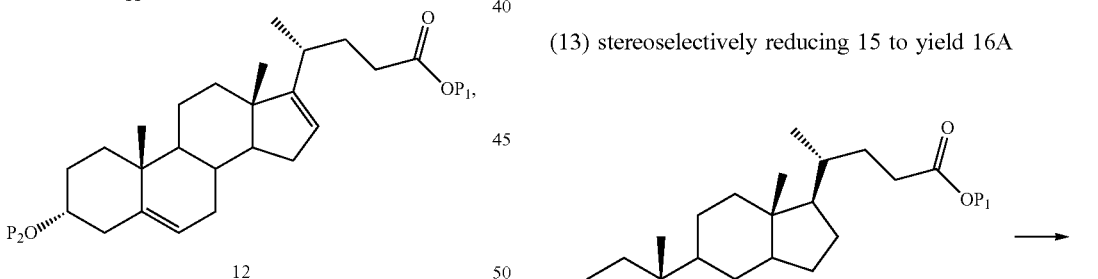
12
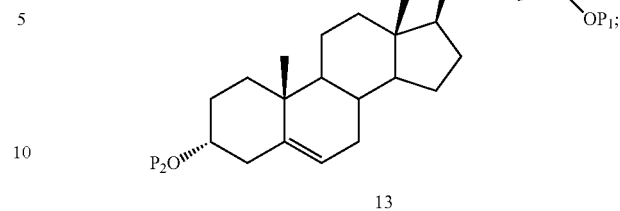
13
(12) oxidizing 13 regioselectively to yield 15
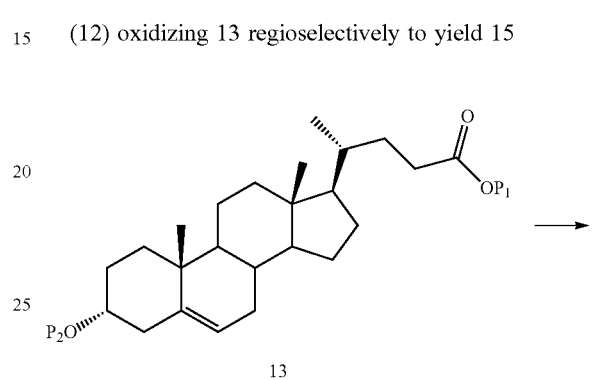
13
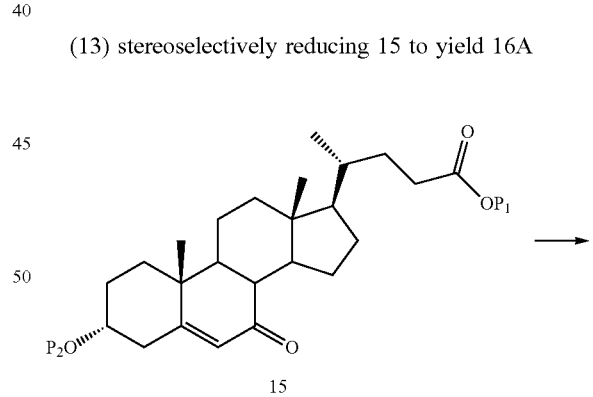
15
(13) stereoselectively reducing 15 to yield 16A
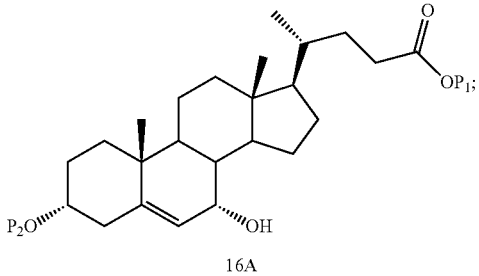
15
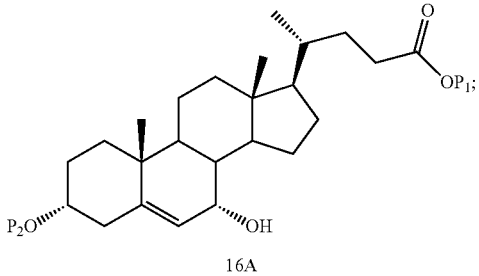
16A

(14) stereoselectively reducing 16A to yield 17

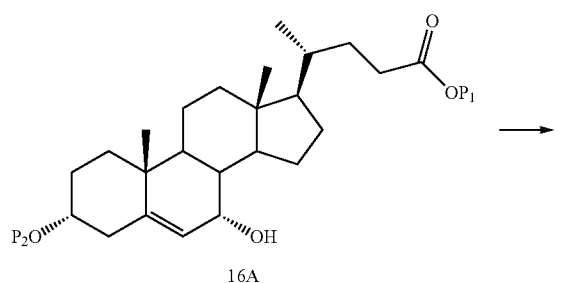

16A

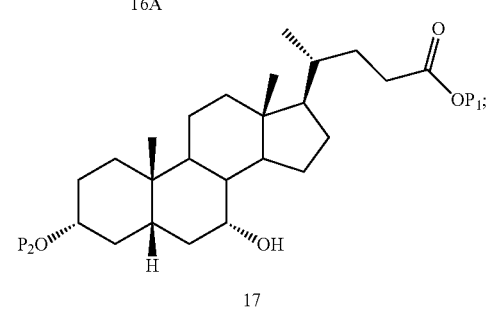

17

(15) selectively deprotecting 17 to yield 17A

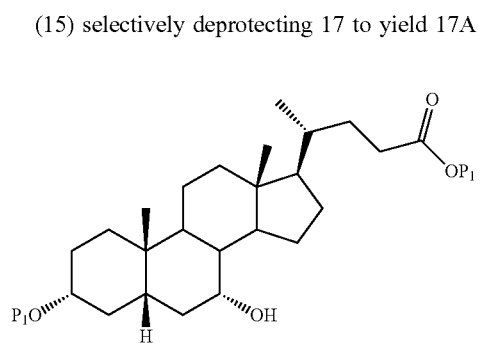

17

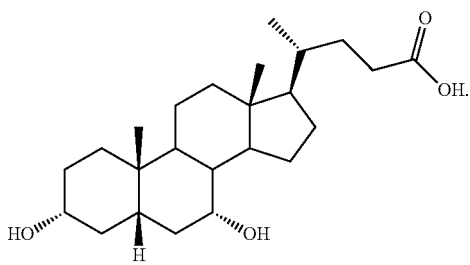

and
(16) converting 17A to yield a compound of Formula (I) wherein $R_1$ is α-OH

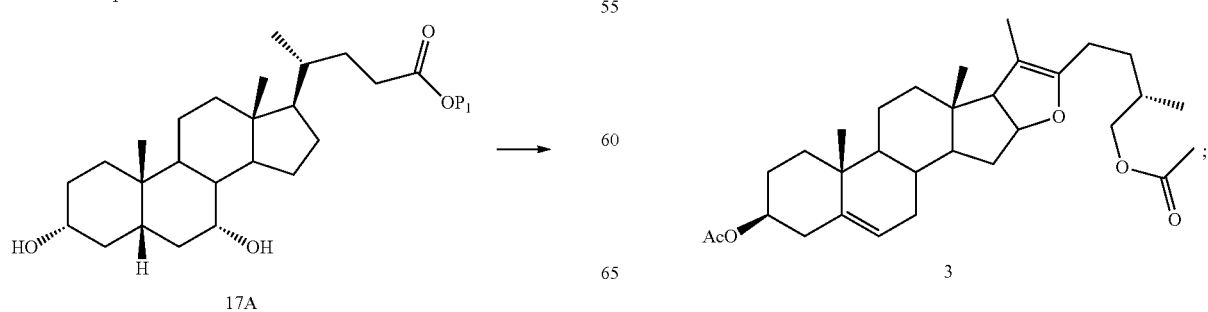

In one aspect, the present application is directed to a process for preparing a compound of Formula (I):

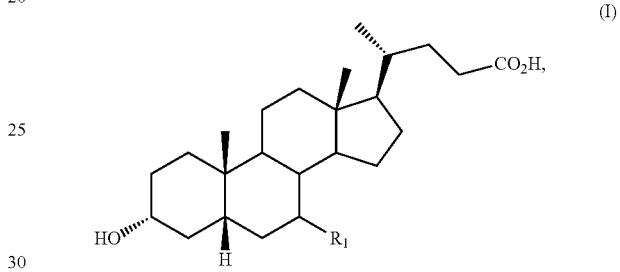

(I)

or a pharmaceutically acceptable salt, solvate, or amino acid conjugate thereof, wherein $R_1$ is β-OH, comprising the steps of:

(1) converting 2 to 3

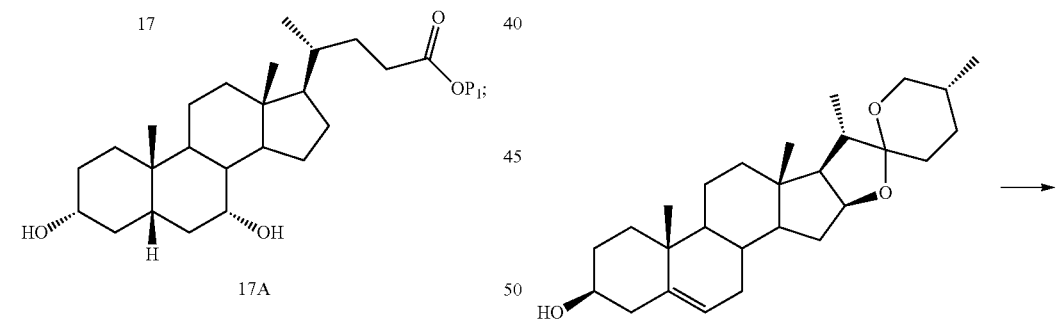

(2) selectively oxidizing 3 to yield 4
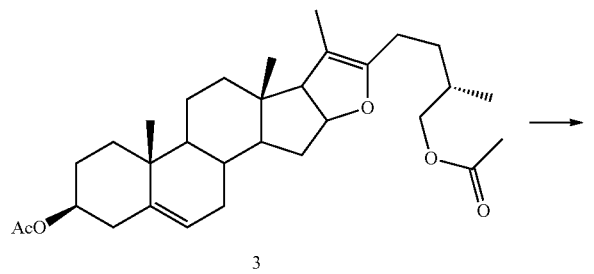
3
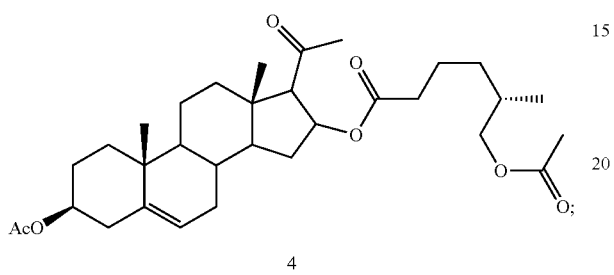
4
(3) converting 4 to 5
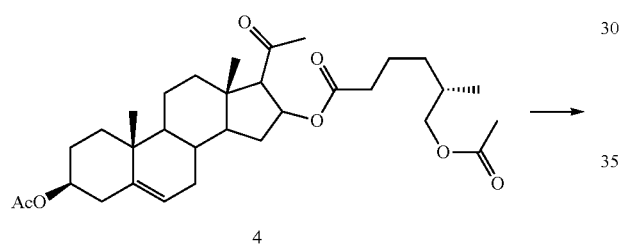
4
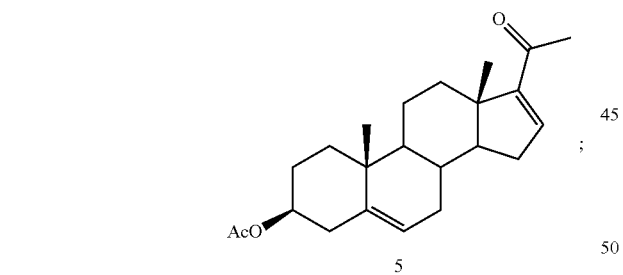
5
(4) converting 5 to oxime 6
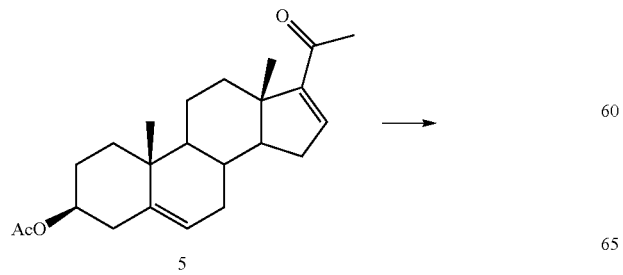
5
-continued
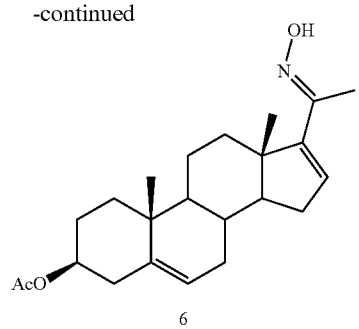
6
(5) converting oxime 6 to 7
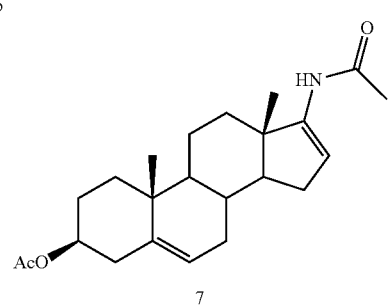
6
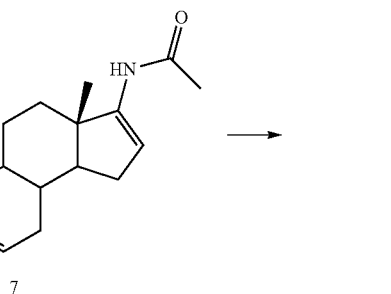
7
(6) converting 7 to ketone 8
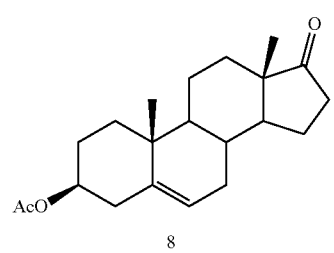
7
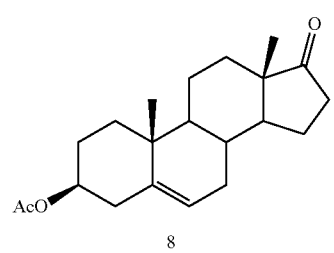
8

(7) deprotecting ketone 8 to form ketone 9;
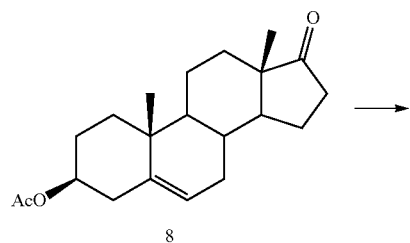
8
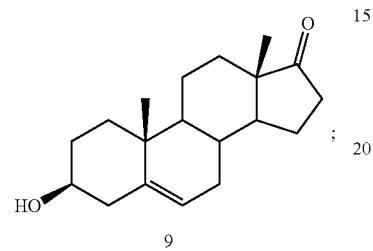
9
(8) olefinating 9 to yield 10
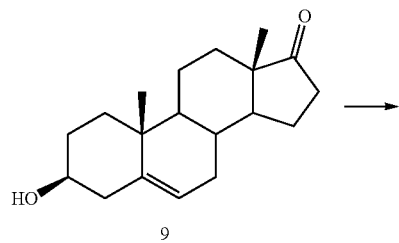
9
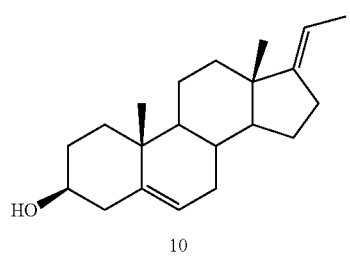
10
(9) alkylating olefin 10 regioselectively and stereoselectively to yield 11
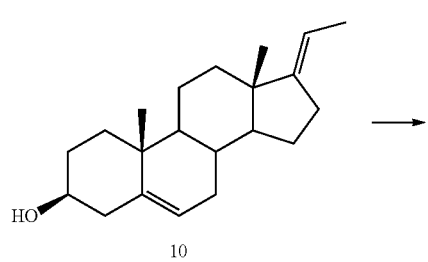
10
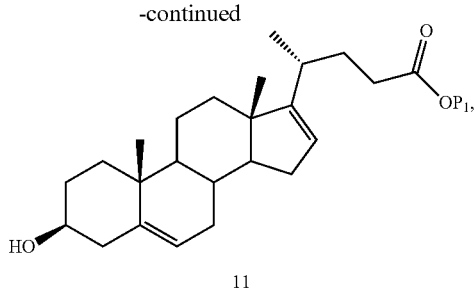
11
wherein $P_1$ is a protecting group or H;
(10) converting 11 to yield 12
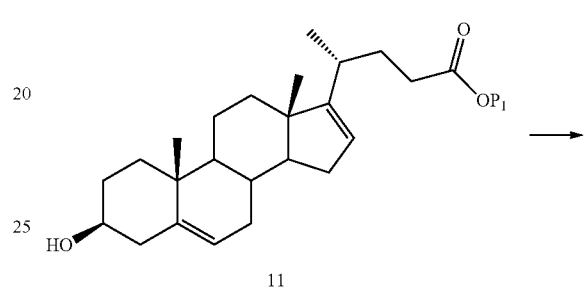
11
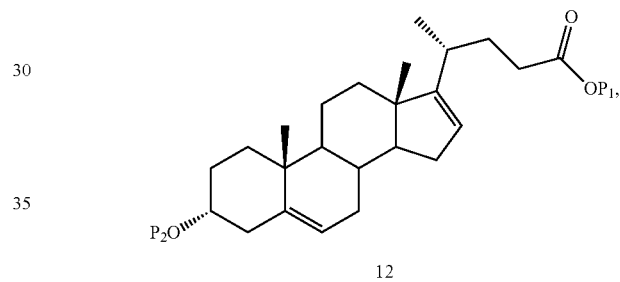
12
wherein $P_2$ is a protecting group;
(11) regioselectively and stereoselectively reducing 12 to yield 13
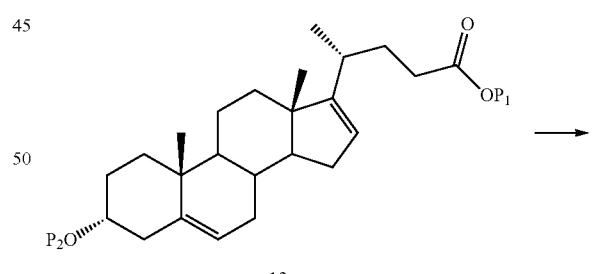
12
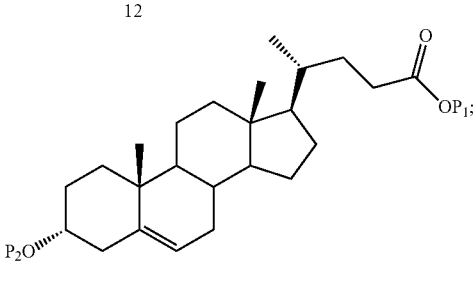
13

(12) oxidizing 13 regioselectively to yield 15
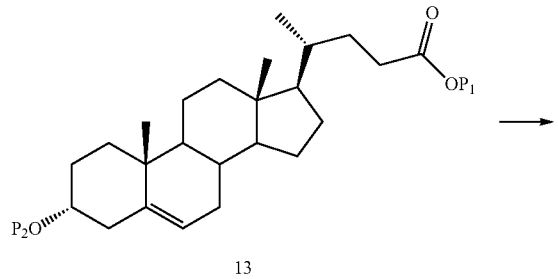
13
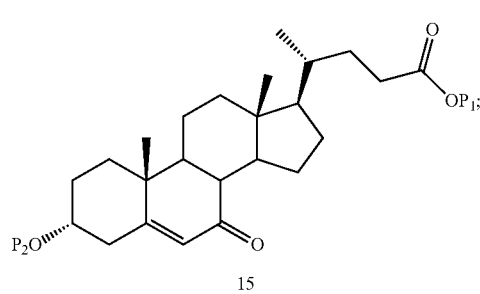
15
(13) stereoselectively reducing 15 to yield 16B
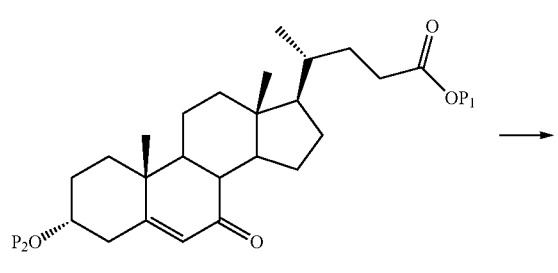
15
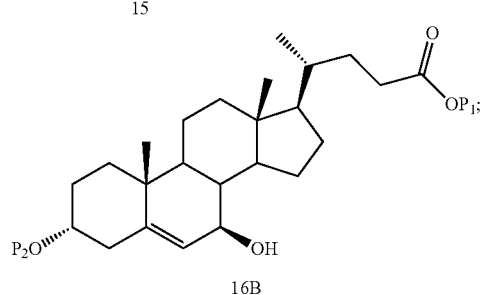
16B
(14) stereoselectively reducing 16B to yield 18
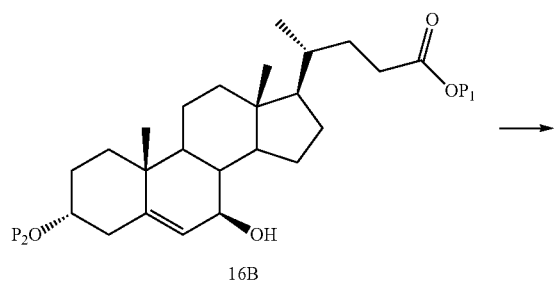
16B
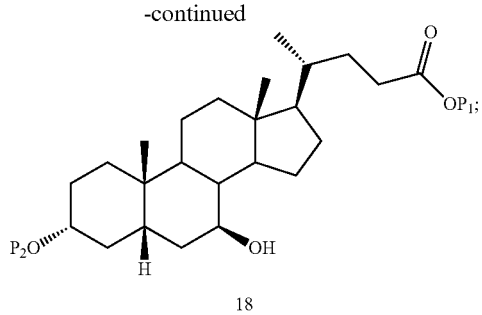
18
(15) deprotecting 18 to yield 18A
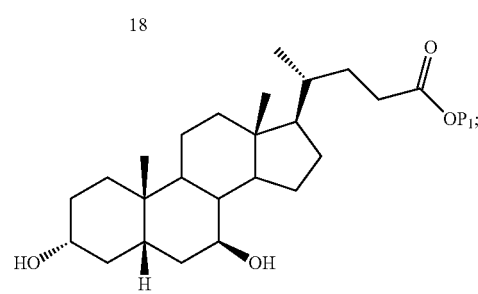
18
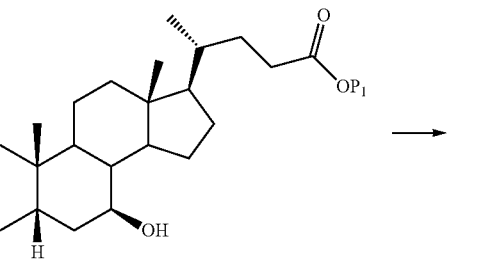
18A
and
(16) hydrolyzing 18A to yield a compound of Formula (I)
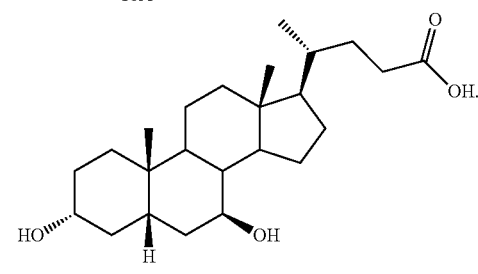
18A In one aspect, the present application is directed to a process for preparing compound 7:
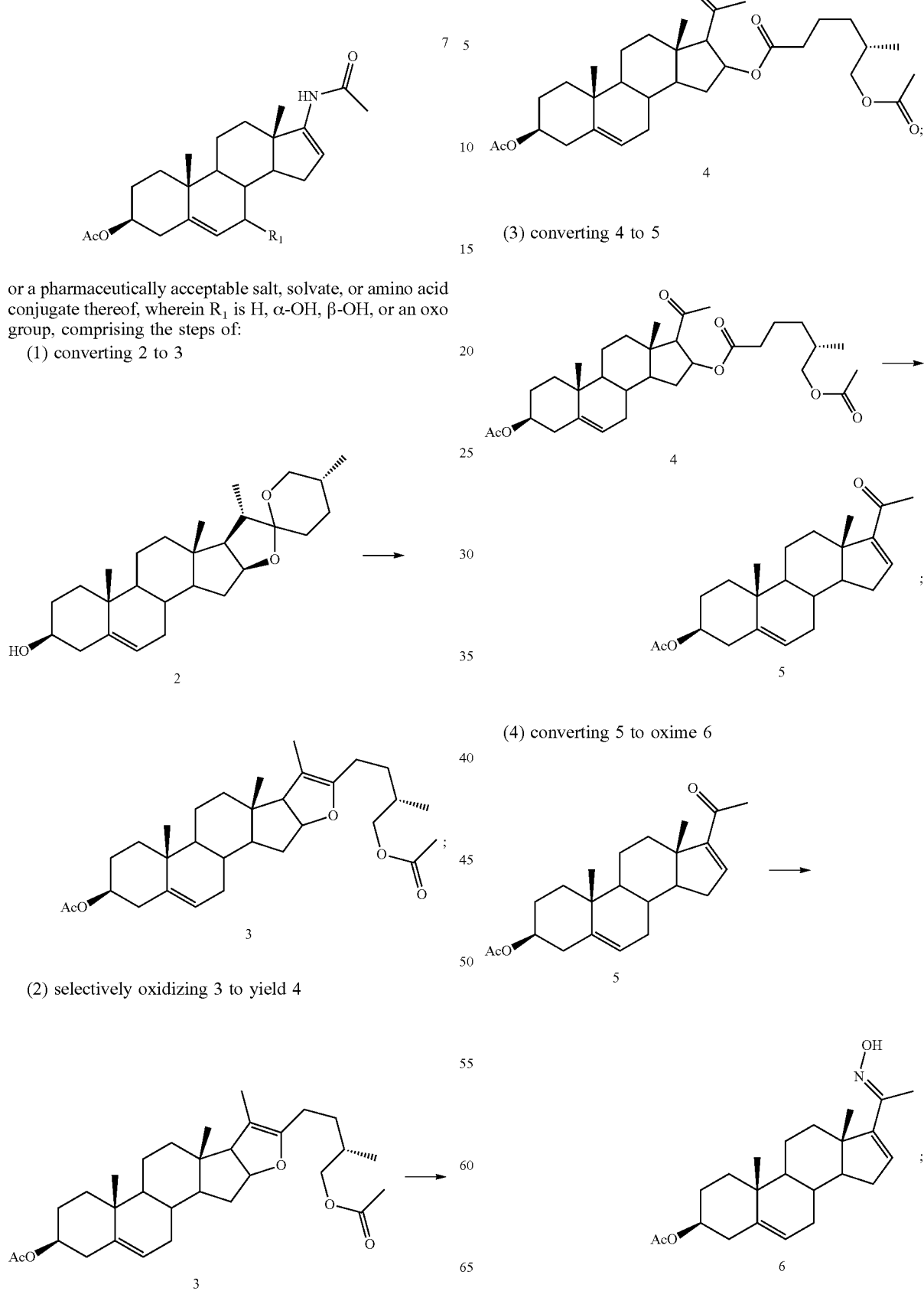
or a pharmaceutically acceptable salt, solvate, or amino acid conjugate thereof, wherein $R_1$ is H, α-OH, β-OH, or an oxo group, comprising the steps of:
(1) converting 2 to 3
(2) selectively oxidizing 3 to yield 4
(3) converting 4 to 5
(4) converting 5 to oxime 6 and (5) converting oxime 6 to 7

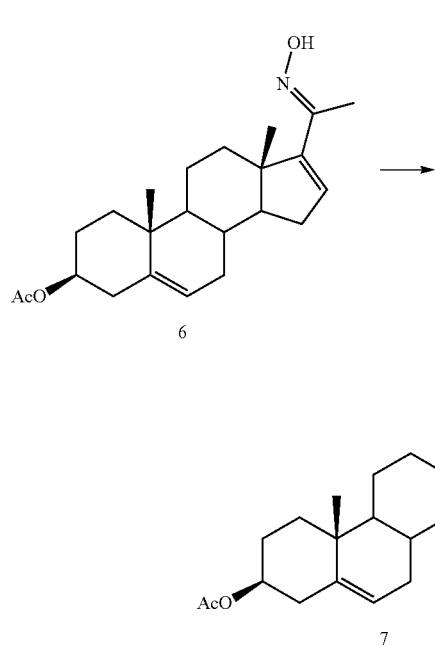

In another aspect, the present application is directed to a process for preparing Compound 4 wherein $R_1$ is H, α-OH, β-OH, or an oxo group, comprising selectively oxidizing 3 to 4,

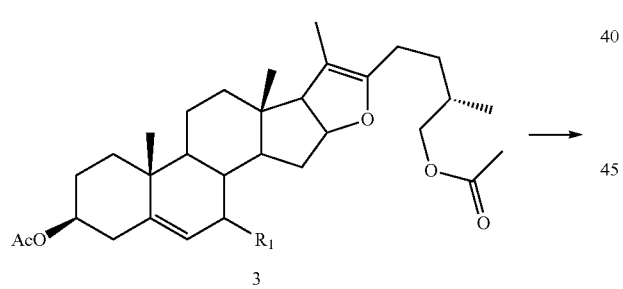

In one aspect, the present application is directed to a process for preparing Compound 5 wherein $R_1$ is H, α-OH, β-OH, or an oxo group, comprising converting 4 to 5,

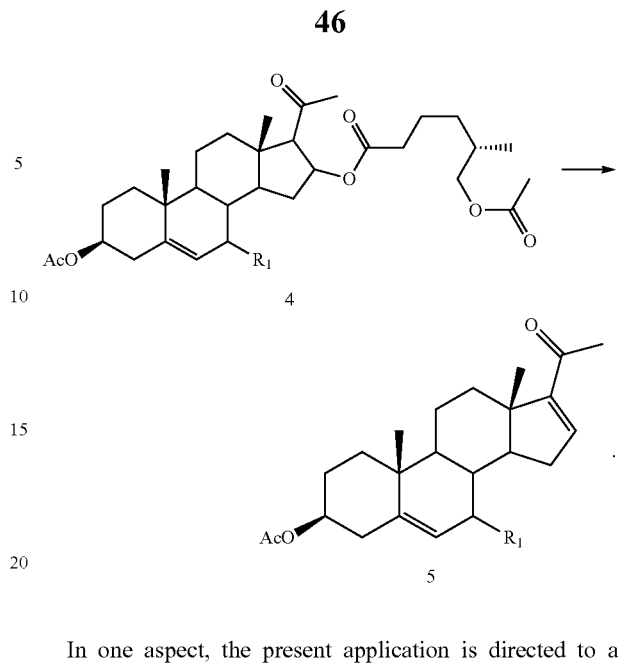

In one aspect, the present application is directed to a process for preparing Compound 8 wherein $R_1$ is H, α-OH, β-OH, or an oxo group, comprising converting 7 to 8,

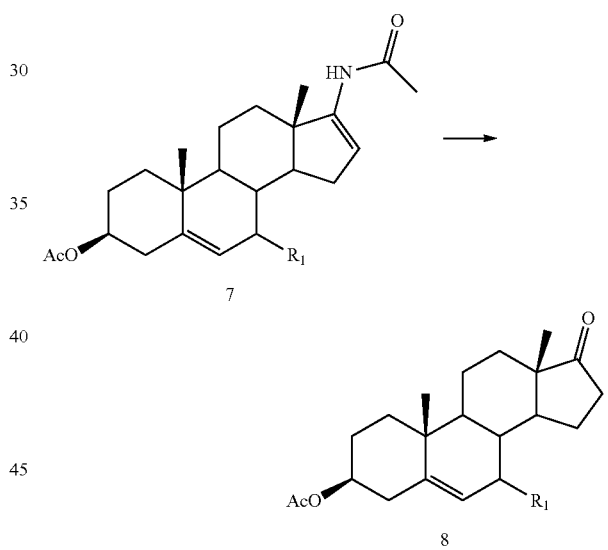

In another aspect, the present application is directed to a process for preparing Compound 11 wherein $R_1$ is H, α-OH, β-OH, or an oxo group; and $P_1$ is H or a protecting group, comprising alkylating olefin 10 regioselectively and stereoselectively to yield 11,

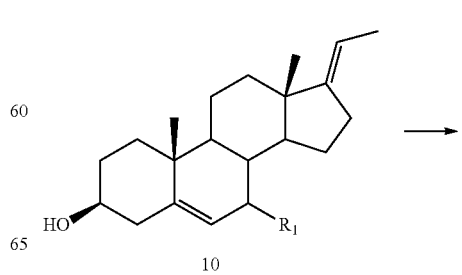

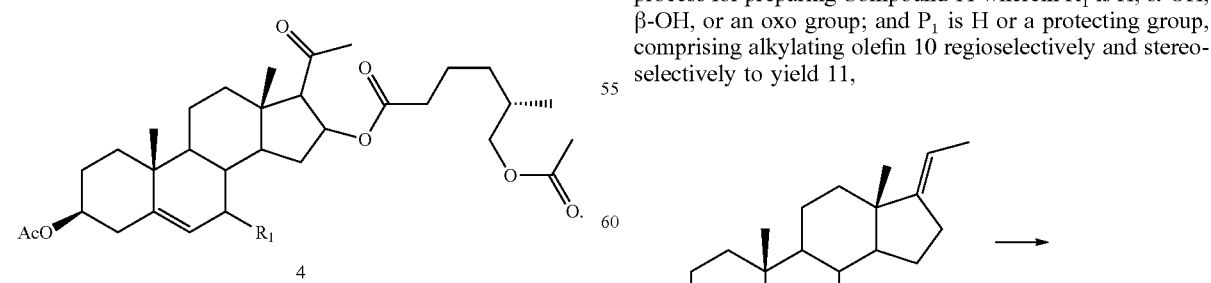

-continued

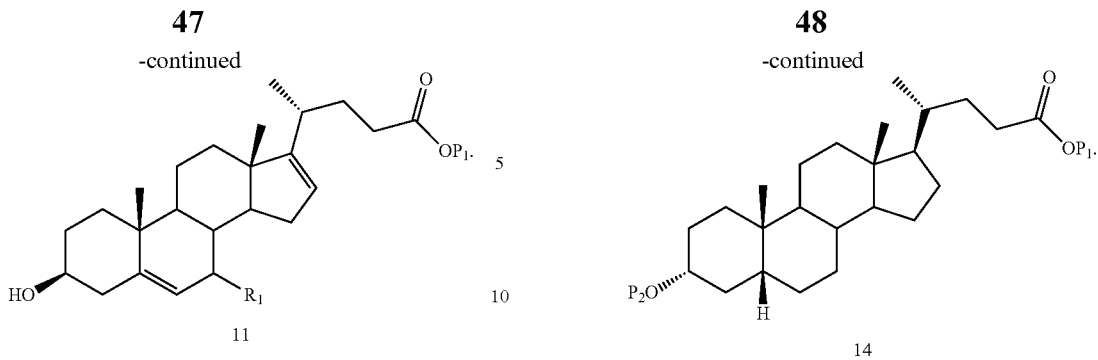

11

In one aspect, the present application is directed to a process for preparing Compound 13 wherein: $P_1$ is H or a protecting group and $P_2$ is a protecting group, comprising regioselectively and stereoselectively reducing 12 to 13,

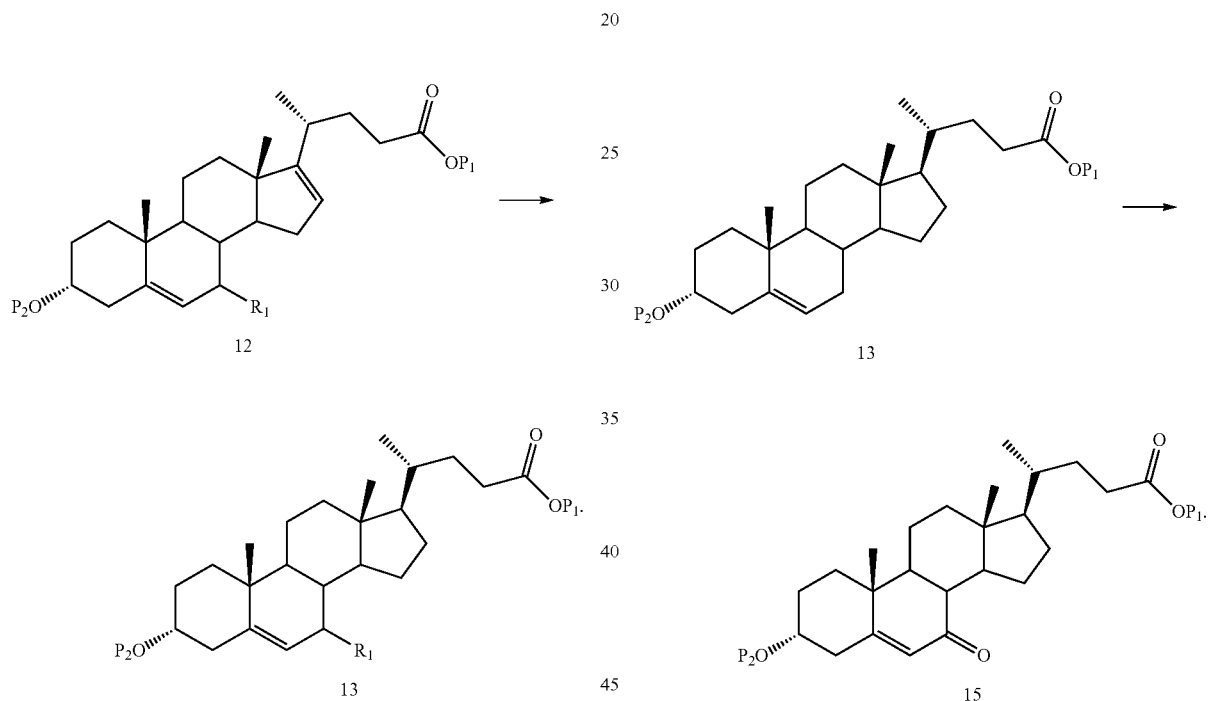

In one aspect, the present application is directed to a process for preparing Compound 14 wherein $P_1$ is H or a protecting group and $P_2$ is a protecting group, comprising oxidizing 13 to 14, -continued

14

In one aspect, the present application is directed to a process for preparing Compound 15 wherein $P_1$ is H or a protecting group and $P_2$ is a protecting group, comprising selectively oxidizing 13 to 15, In one aspect, the present application is directed to a process for preparing Compound 16A wherein $P_1$ is H or a protecting group and $P_2$ is a protecting group, comprising selectively reducing 15 to 16A or 16B,

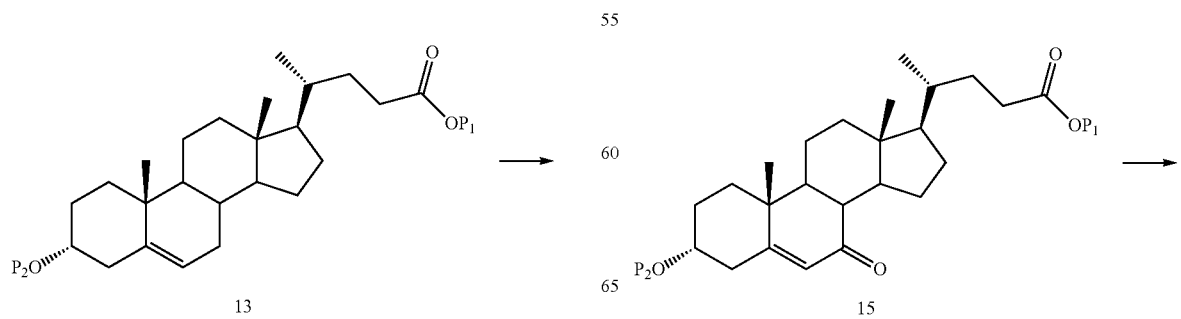

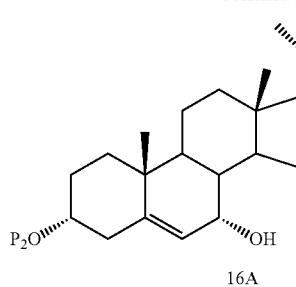

16A

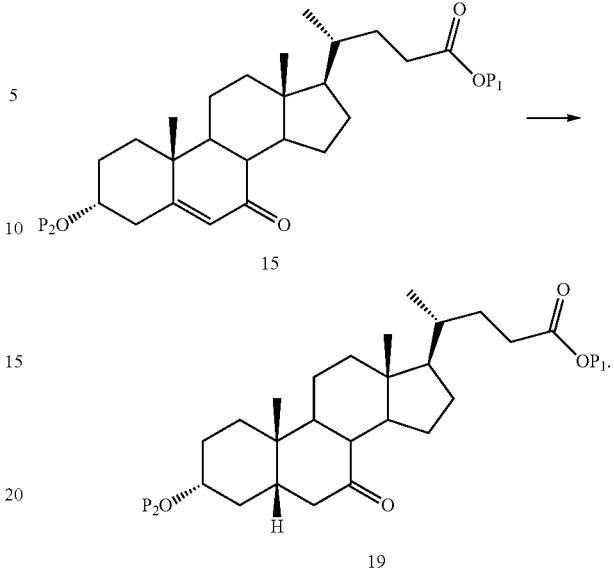

15

19

In one aspect, a compound of Formula (I) synthesized from the disclosed methods is selected from the group consisting of:

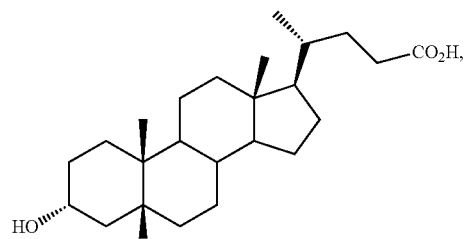

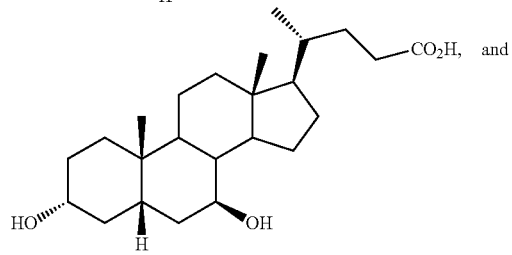

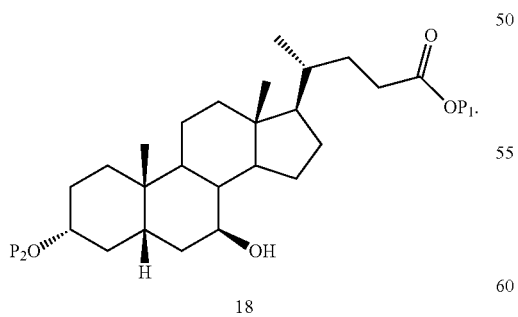

or a pharmaceutically acceptable salt, solvate, or amino acid conjugate thereof.

16B

In one aspect, the present application is directed to a process for preparing Compound 18 wherein $P_1$ is H or a protecting group and $P_2$ is a protecting group, comprising selectively reducing 16B to 18,

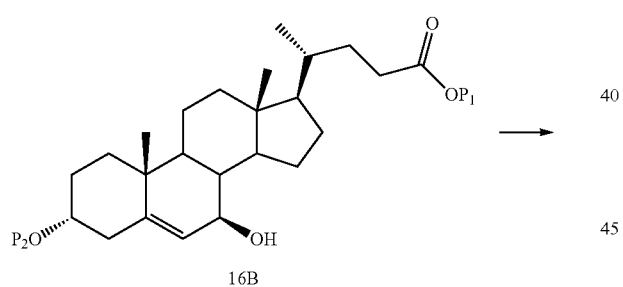

16B → 18

In one aspect, the present application is directed to a process for preparing compound 19 wherein $P_1$ is H or a protecting group and $P_2$ is a protecting group, comprising selectively reducing 15 to 19,

DETAILED DESCRIPTION

The present application is directed to the synthesis of bile acids (BAs) from diosgenin, a naturally occurring steroid sapogenin found in abundance in various plant species.

More specifically, the present application relates to the synthesis of chenodeoxycholic acid (CDCA) and related compositions from diosgenin, including but not limited to lithocholic acid (LCA), 7-oxo-lithocholic acid (also known as 7-keto-lithocholic acid, or 7-KLCA), ursodeoxycholic acid (UDCA), and useful intermediates thereof. The synthesis of the present application advantageously does not rely on microorganisms. Accordingly, the bile acids prepared by the methods of the present application are free of toxins and contaminants associated with preparation of bile acids from starting materials from mammalian and microbial organisms. The isolation of intermediates may be performed by known purification methods including, but not limited to, column chromatography and crystallization.

Methods of Synthesis

The present application provides a method of synthesizing compounds of Formula (I),

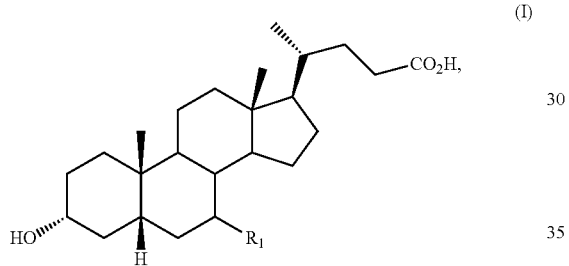

(I)

or a pharmaceutically acceptable salt, solvate, or amino acid conjugate thereof, wherein $R_1$ is H, α-OH, β—OH, or an oxo group, from Compound 2 (diosgenin):

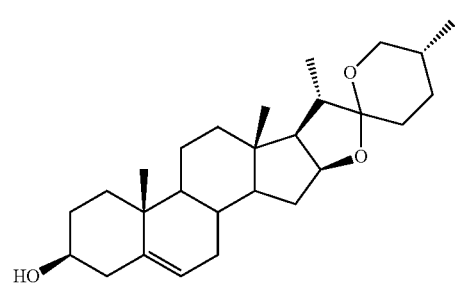

2

The compound of formula (I), wherein $R_1$ is α-OH or β-OH, can be oxidized to afford the corresponding oxo compound.

For the sake of clarity, but without limiting the scope of the invention, $R_1$ is specified as H, α-OH, β-OH, or an oxo group in the formulas of the synthetic schemes.

In one embodiment, the present application comprises converting Compound 2 to Compound 5:

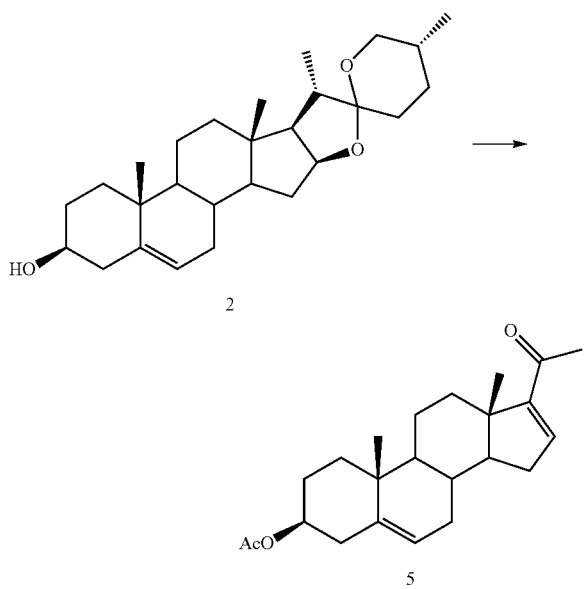

by acetolysis followed by selective oxidation and hydrolysis.

In one embodiment, the conversion of Compound 2 to Compound 5 is achieved by opening the spiroketal ring system of Compound 2 by acetolysis with acetic anhydride to produce Compound 3:

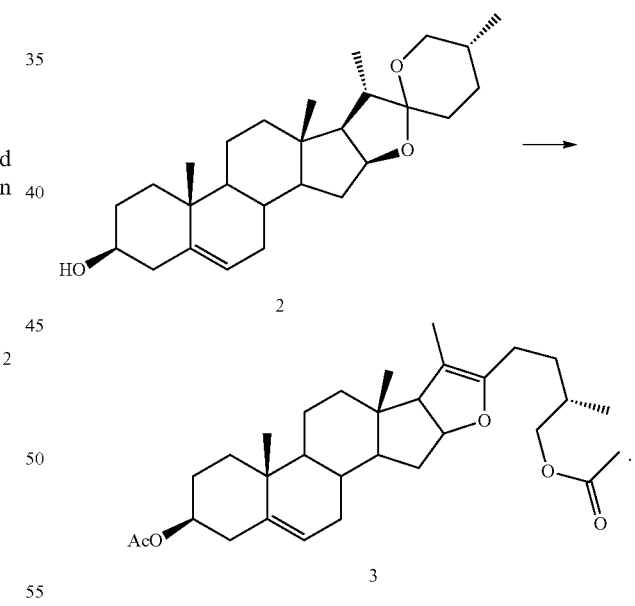

In some embodiments, acetolysis of Compound 2 may be performed uncatalyzed under elevated pressure or acid or base-catalyzed without pressure. In one embodiment, acetolysis may be performed with acetic anhydride. In another embodiment, acetolysis may be performed with acetic acid trifluoroacetic mixed anhydride (ATFAA) and $BF_3.OEt_2$. In yet another embodiment, the reaction may be performed in xylene, methylene chloride or 1,2-$Cl_2C_6H_4$ and combinations thereof. When acetolysis is catalyzed, suitable catalysts may include, but are not limited to, hydrochloric acid, p-toluenesulfonic acid, acetyl chloride, aluminum chloride, octanoic acid, pyridine/acetyl chloride and pyridinium hydrochloride. In one embodiment, acetolysis by acetic anhydride is performed in net conditions at reflux or with microwave irradiation. The conversion may be performed at an elevated temperature of between about 100° C. to about 200° C., e.g. 100° C. 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C. and 200° C. as well as any degree increment in between, and may, for example, be held at the elevated temperature until the reaction is complete.

In certain embodiments, the reaction can be performed or conducted under flow chemistry conditions. Advantages of using continuous-flow chemistry include synthetic efficiency and productivity, a high product quality, improved eco-sustainability with a reduced production of waste, and a lower cost of the process. Methods developed with integrated flow systems facilitate the optimization of the process allowing to the finding of robust and reliable large scale preparation of target compounds eventually purified with in-line apparatus. Moreover, product outcome can be easily controlled with in-line analytical devices eventually supported by software. This approach is therefore applicable to a range of different embodiments as well as a range of different reaction steps, such as, without limitation, oxidation reactions, ozonolysis reactions, hydrogenation reactions, reduction reactions, olefination reactions, etc. Specifically, reactions such as those characterized herein include, converting compound 2 to compound 3, selectively oxidizing compound 3 to yield compound 4, converting compound 4 to compound 5, converting compound 7 to ketone 8, olefinating compound 9 to yield compound 10, regioselectively and stereoselectively reducing 12 to yield 13, stereoselectively reducing compound 15 to yield compound 16A, stereoselectively reducing compound 16A to compound 17, stereoselectively reducing the compound of 16B to yield compound 18. The present invention contemplates one or more of these steps being carried out or conducted under flow chemistry conditions. In some cases, all of the steps may be conducted under flow chemistry conditions.

The conversions may be performed under super critical conditions, for example $CH_2Cl_2$ may be used at 200° C. On demand hydrogen and supported catalysts, such as palladium nanoparticles, can be employed for embodiments involving hydrogenation reactions. Microreactors or capillary flow reactors may be used in embodiments involving hydrogenation or ozonolysis. Microreactors can be of 2, 5, or 10 mL volume and flow rates may be from 0.25 to 1 mL/min (and any increment in between), reactor volumes are from 0.07 to 10 mL (and any increment in between), formed typically from 1 mm ID tubing. The reaction temperatures may range from −70° C. up to 250° C. In some embodiments, pressurized reaction conditions may be employed with pressures of up to about 40 bar, but can comprise any amount ranging from atmospheric pressure and above, e.g., 1 bar, 2 bar, 3 bar, 4 bar, 5 bar, 6 bar, 7 bar, 8 bar, 9 bar, 10 bar, 11 bar, 12 bar, 13 bar, 14 bar, 15 bar, 16 bar, 17 bar, 18 bar, 19 bar, 20 bar, 21 bar, 22 bar, 23 bar, 24 bar, 25 bar, 26 bar, 27 bar, 28 bar, 29 bar, 30 bar, 31 bar, 32 bar, 33 bar, 34 bar, 35 bar, 36 bar, 37 bar, 38 bar, 39 bar and 40 bar.

In one embodiment, the reaction is conducted from about 2 hours to about 24 hours, about 4 hours to about 20 hours, about 8 hours to about 18 hours, e.g., 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours and including any increment in between.

Compound 3 is then selectively oxidized at the 20(22) enolic double bond to produce Compound 4:

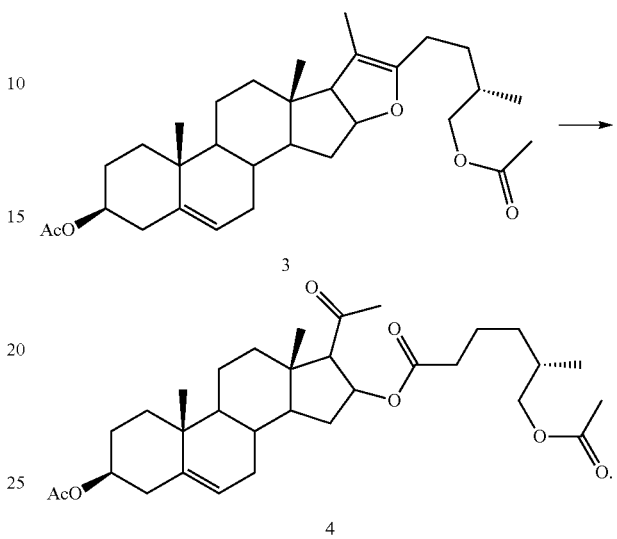

In some embodiments, the heated reaction mixture containing compound 3 is cooled, and oxidation is performed at a temperature of between about −20° C. to about 20° C., e.g. −20° C., −15° C., −10° C., −5° C., 0° C., 5° C., 10° C., 15° C. and 20° C., as well as any degree increment in between. Oxidation may be performed using a suitable oxidant in solvent, e.g., $CrO_3$, in $CH_3CO_2H$. In one embodiment, the oxidation may be performed by the use of catalytic $CrO_3$ in the presence of an oxidant (e.g., Oxone or an organic per-acid). In another embodiment, the oxidation may be performed with $NaIO_4$ and $RuCl_3$, followed by the addition of $H_2SO_4$. In another embodiment, the oxidation may be performed with $KMnO_4$, $NaIO_4$ and TEBAC. In another embodiment, the oxidation may be performed with ozone. In yet another embodiment, the reaction may be performed in ethyl acetate, methylene chloride or acetic acid and combinations thereof. After the oxidant has been added to the reaction mixture, the mixture may be heated, for example, to room temperature. In some embodiments, the mixture is stirred. In other embodiments, the reaction may be conducted under flow chemistry conditions, as described herein.

In one embodiment, the oxidation reaction is conducted for about 2 hours to about 8 hours, about 4 hours to about 6 hours, e.g., 2 hours, 3 hours, 4 hours, 5 hours, 6 hours, 7 hours, 8 hours and including any increment in between.

Compound 4 is then converted to Compound 5 by hydrolysis:

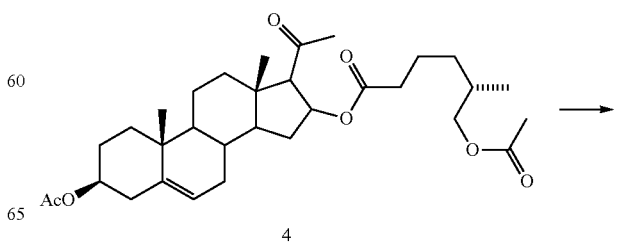

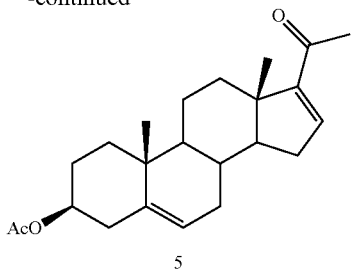

5

Hydrolysis may be performed by a base. In one embodiment, the base is a metal hydroxide (e.g. sodium hydroxide or potassium hydroxide). In another embodiment, the base is a metal carboxylate (e.g. sodium acetate or potassium acetate). In another embodiment, the base is a metal carbonate (e.g. sodium carbonate or potassium carbonate). In one embodiment, the base is a tertiary amine (e.g. diisopropylethylamine or triethylamine). In some embodiments, the reaction is refluxed for a period of between about 1 hour and about 5 hours, e.g., 1 hour, 2 hours, 3 hours, 4 hours, 5 hours and any increment in between. In certain aspects, the hydrogenation step may be performed under flow chemistry conditions.

In some embodiments, the yield of Compound 5 from Compound 2 may be from about 50% to about 90% of Compound 2, from about 60% to about 70% of Compound 2, e.g., about 50%, about 55%, about 60%, about 65%, about 70%, about 75%, about 80%, about 85%, about 90%, and any percentage increment in between.

In one embodiment, Compound 5 is washed and filtered after the reaction is completed.

In one embodiment, the method of the present application further comprises converting Compound 5 to oxime Compound 6:

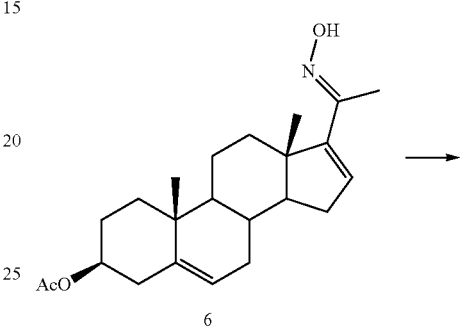

In some embodiments, Compound 6 is produced by the reaction of Compound 5 in a protic solvent, for example, ethanol, with NH$_2$OH.HCl and diisopropylamine (DIPA). In some embodiments, the mixture is refluxed for about 30 minutes to about 3 hours, from about 1 hour to about 3 hours, e.g., 30 minutes, 1 hour, 1.5 hours, 2 hours, 2.5 hours, 3 hours and any increment in between.

In one embodiment, the reaction mixture containing Compound 6 is cooled, washed, and dried.

In one embodiment, the yield of Compound 6 is from about 80% to 90%.

In one embodiment, the reaction mixture containing Compound 6 is washed and filtered.

In one embodiment, the method of the present application further comprises converting Compound 6 to Compound 9:

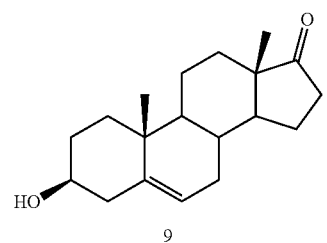

In some embodiments, Compound 6 is converted to compound 9 by way of intermediate Compounds 7 and 8:

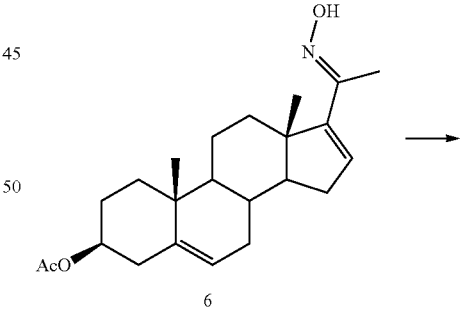

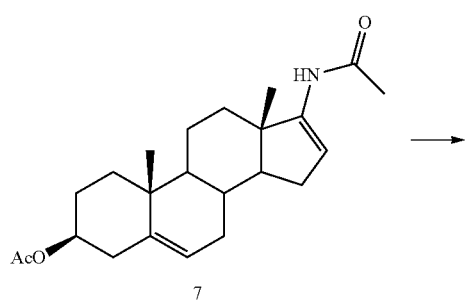

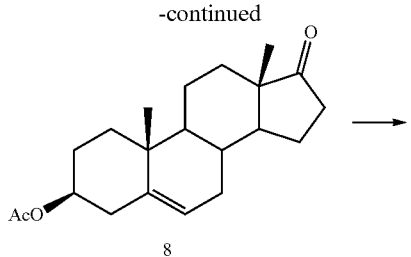

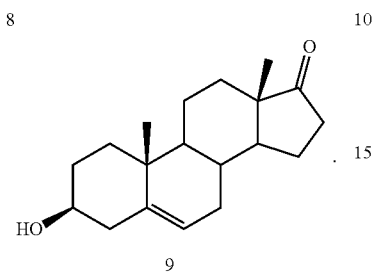

In some embodiments, conversion of Compound 6 to Compound 9 is performed by reacting Compound 6 with POCl$_3$ and trimethylamine or pyridine in an organic solvent, for example, THF, benzene, toluene, or pyridine, in the presence of an inert gas, for example, argon. In some embodiments, the reaction may be performed at a lower temperature, e.g., 0° C., followed by a higher temperature, e.g., room temperature. In some embodiments, the reaction is conducted from about 1 hour to about 4 hours, e.g., about 1 hour, about 1.5 hours, about 2 hours, about 2.5 hours, about 3 hours, about 3.5 hours, about 4 hours, and any increment in between.

In some embodiments, the reaction product containing Compound 7 may be converted to Compound 9 by way of Compound 8, where the hydroxyl protecting group, acetyl (Ac), on Compound 8 is removed to yield Compound 9. In certain embodiments, Compound 7 may be converted to Compound 9 under flow chemistry conditions.

In some embodiments, the reaction mixture comprising Compound 7 is reacted with a base, for example a Group II metal hydroxide, e.g., KOH, LiOH, Ca(OH)$_2$, Mg(OH)$_2$ or NaOH, in a protic solvent, e.g., methanol, ethanol, isopropanol, propanol, or butanol, and the mixture is refluxed for about 6 hours to about 24 hours, e.g., about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, about 24 hours and any increment in between. The mixture may then be extracted with an aprotic solvent. In one embodiment, the aprotic solvent is an alkyl acetate, e.g., methyl acetate, ethyl acetate, isobutyl acetate or butyl acetate. In another embodiment, the aprotic solvent is a dialkyl ether, e.g., diethyl ether or methyl t-butyl ether (MTBE). In one embodiment, the aprotic solvent is toluene or CH$_2$Cl$_2$. The organic layer may be removed to obtain Compound 9. In some embodiments, Compound 9 is recrystallized, for example, with methanol, ethanol, isopropanol, propanol, butanol with or without water.

In one embodiment, the method of the present application further comprises converting Compound 9 to Compound 11

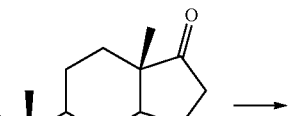

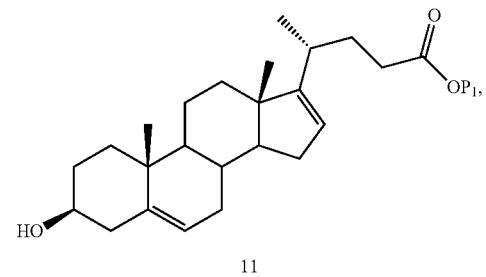

wherein P$_1$ is H or a protecting group, following by alkylation. Protecting group P$_1$ is an appropriate moiety for masking an acid functionality and may be, for example, an alkyl, benzyl, trialkylsilyl, or P$_1$ forms an oxazoline ring with the carbonyl, or any other group that is non-reactive with further steps of the synthesis. One skilled in the art will recognize the particular moieties employed for protecting a carboxylic acid instead of another functionality, e.g. hydroxyl. The protecting group can be any protecting group that is stable/non-reactive under the reaction condition (e.g., non-reactive with an agent used in the reaction). In one embodiment, the protecting group is selected from alkyl, benzyl, and trialkyl silyl. In one embodiment, the trialkylsilyl is selected from trimethylsilyl (TMS), triethylsilyl (TES), triisopropylsilyl (TIPS), tert-butyldimethylsilyl (TBDMS), and tert-butyldiphenylsilyl (TBDPS). In one embodiment, the protecting group is benzyl or ethyl.

For example, Compound 9 may be olefinated to produce Compound 10 which is then alkylated to produce Compound 11:

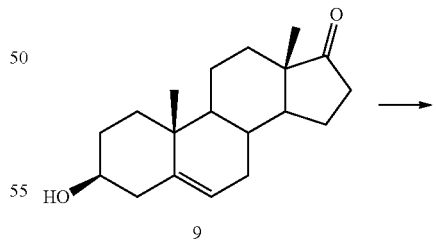

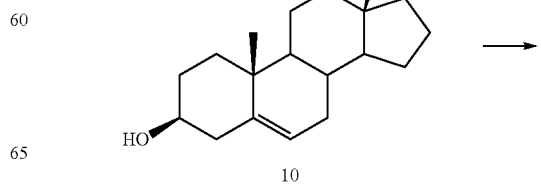

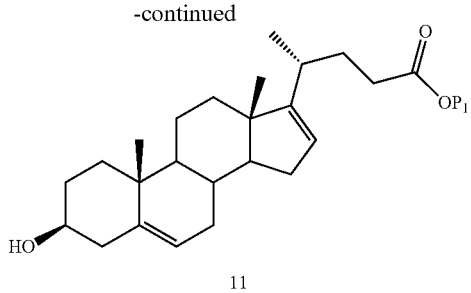

11

In one embodiment, the olefination of Compound 9 involves a Wittig reaction including the Horner-Emmons procedure. In a separate embodiment, the olefination of Compound 9 involves the Peterson olefination process. In further embodiments, organometallic reagents involving geminal dimetallic derivatives ($L_n$ $M^1$-CHR-$M^2$ $L_n$) or nucleophilic metallocarbenes (Ln M=CHR) can be used for the preparation of the olefin. L represents a ligand and M represents a metal in the organometallic reagents. In one embodiment, the metal is ruthenium. In certain aspects, the olefination may be conducted under flow chemistry conditions.

In further embodiments, a two-step olefination involving the addition of an organometallic reagent (e.g., Et-MgX, where X is Cl, Br, or I; Et-Li) to the D-ring carbonyl, followed by treatment of the intermediate alcohol product with a dehydration agent (e.g., $POCl_3$) may be used. See Giacopello, et al., 1992, Zeitschrift fuer Naturforschung, 47, 891 and Hershber, et al., 1951, JACS, 73, 5073.

In some embodiments, Compound 9 may undergo a Wittig reaction with $EtPPh_3Br$ to insert an ethylidene group in the C17 position to yield Compound 10. In some embodiments, the reaction is performed in the presence of t-BuOK and an aprotic solvent, where Compound 9 in aprotic solvent, for example, THF, is added dropwise to a suspension of $EtPPh_3Br$, t-BuOK and THF, and then refluxed.

In some embodiments, the reaction is conducted for about 2 hours to about 10 hours, e.g., 2 hours, 2.5 hours, 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, and any increment in between.

In some embodiments, Compound 9 is olefinated with methyl acrylate or methyl propiolate in the presence of $EtAlCl_2$ or $MeAlCl_2$ to yield Wittig-ene adduct Compound 10.

In accordance with embodiments, the reaction may be performed at a reduced temperature, for example about 0° C. to about –20° C., e.g., 0° C., –5° C., –10° C., –15° C., –20° C., and any degree increment in between, and the mixture may then be heated to a higher temperature, e.g., room temperature.

In some embodiments, the reaction is conducted for about 24 to about 76 hours, e.g., 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, 72 hours, 73 hours, 74 hours, 75 hours, 76 hours, and any increment in between.

In one embodiment, the method of the present application further comprises converting Compound 11 to Compound 12 having a protecting group $P_2$ on the hydroxyl group at the $C_3$ α-position, and regioselectively and stereoselectively reducing Compound 12 to produce Compound 13.

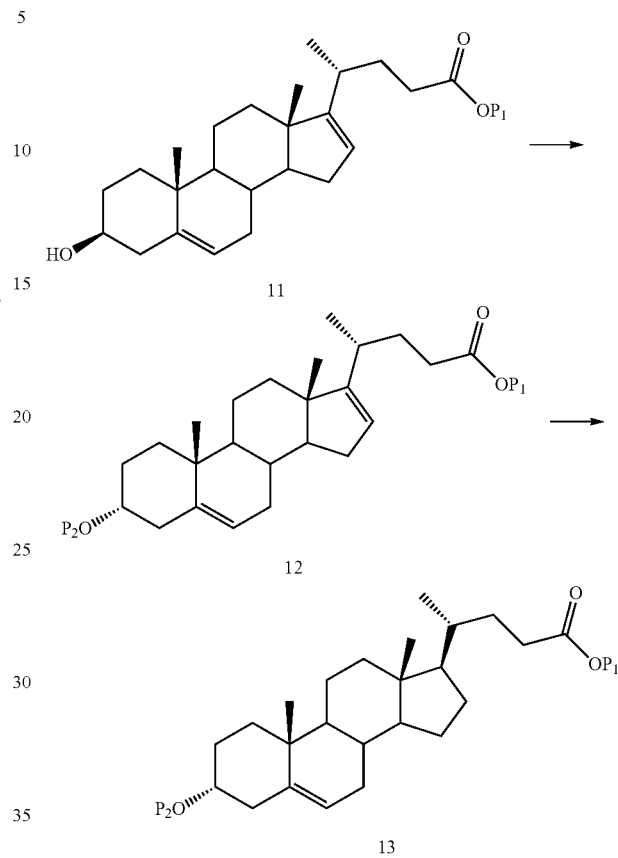

The $P_2$ protecting group is an appropriate moiety for masking a hydroxyl functionality is stable/non-reactive under the reaction condition (e.g., non-reactive with an agent used in the reaction). One skilled in the art will recognize the particular moieties employed for protecting a hydroxyl group instead of another functionality, e.g. carboxylic acid. In one embodiment, the $P_2$ protecting group is selected from $C_1$-$C_6$ alkoxycarbonyl, optionally substituted aryloxycarbonyl, acetyl, benzoyl, benzyl, pivaloyl, tetrahydropyranyl ether (THP), tetrahydrofuranyl, 2-methoxyethoxymethyl ether (MEM), methoxymethyl ether (MOM), ethoxyethyl ether (EE), p-methoxybenzyl ether (PMB), methylthiomethyl ether, triphenylmethyl (trityl, or Tr), dimethoxytrityl (DMT), methoxytrityl (MMT), and silyl ether. In one embodiment, the silyl ether is selected from trimethylsilyl ether (TMS), triethylsilyl ether (TES), triisopropylsilyl ether (TIPS), tert-butyldimethylsilyl ether (TBDMS), and tert-butyldiphenylsilyl ether (TBDPS). In one embodiment, the protecting group is benzoyl or acetyl.

Compound 12 may be selectively reduced to produce Compound 13. In accordance with embodiments, the C16-C17 double bond may be reduced to yield Compound 13. In some embodiments, reduction is achieved by hydrogenation of Compound 12 in the presence of a catalyst, for example, palladium catalyst (e.g., Pd/C), platinum catalyst (e.g., $PtO_2$), nickel catalyst (e.g., Raney nickel and Urushibara nickel), any of which may be used on or in the absence of carbon. In another embodiment, the catalyst may be used homogeneously in a solution. In other embodiments, the hydrogenation can be performed with a catalyst and syngas. In certain aspects, the reduction step may be carried out under flow chemistry conditions. In other aspects, the hydrogenation step may be carried out under flow chemistry conditions.

In one embodiment, the method of the present application further comprises stereoselective reduction of Compound 13 to produce Compound 14.

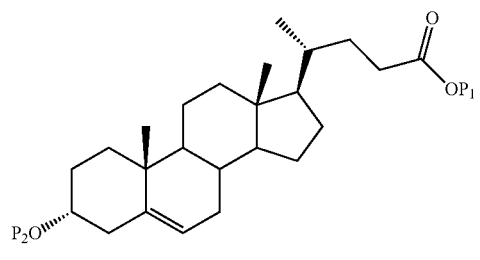

13

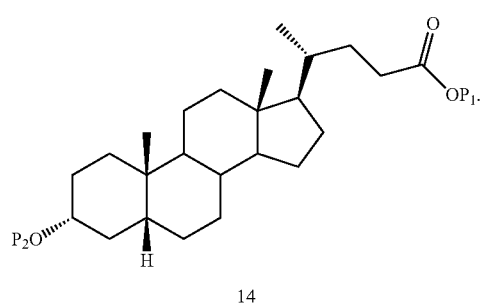

14

In accordance with embodiments, the C5-C6 double bond of Compound 13 can be stereoselectively reduced by hydrogenation. Hydrogenation may take place, for example, in the presence of a catalyst for example, palladium catalyst (e.g., Pd/C), platinum catalyst (e.g., PtO$_2$), nickel catalyst (e.g., Raney nickel and Urushibara nickel), any of which may be used on or in the absence of carbon. In one embodiment, hydrogenation is catalyzed by platinum on carbon. In another embodiment, the catalyst may be used homogeneously in a solution. In another embodiment, the hydrogenation can be performed with a catalyst and syngas. The hydrogenation step may be carried out or conducted under flow chemistry conditions.

The protecting groups P$_1$ and P$_2$ may then be removed to yield LCA, a compound of Formula (I):

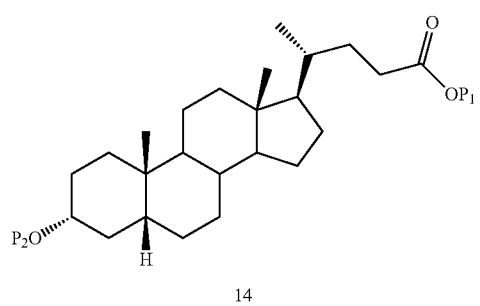

14

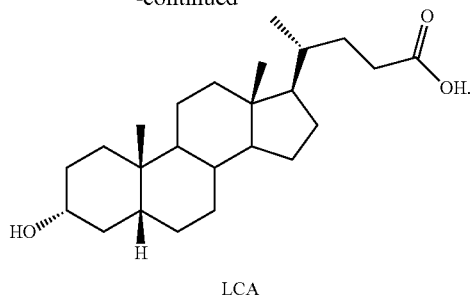

LCA

In one embodiment, Compound 14 is selectively deprotected to remove the hydroxyl group at the C3 position to yield Compound 14a:

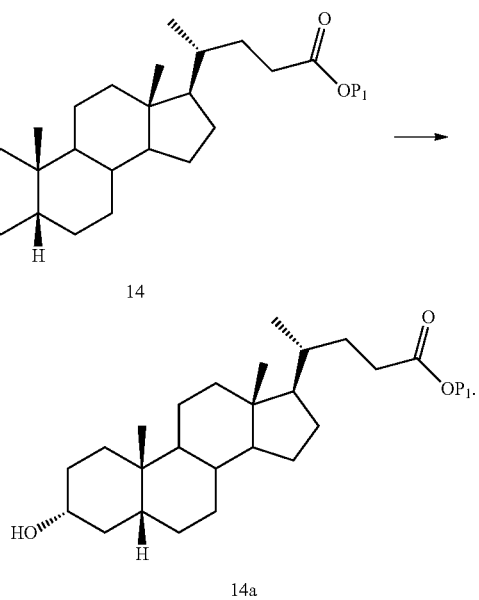

14

14a

In one embodiment, deprotection of the hydroxyl groups is conducted under an acid condition or a basic condition. In one embodiment, the deprotection is conducted under an acid condition using an acid, such as HCl. In one embodiment, the deprotection is conducted under a basic condition using a base, such as metal hydroxide (e.g., sodium hydroxide and potassium hydroxide) or carbonate (e.g., sodium carbonate).

In some embodiments, the remaining protecting group is removed by hydrolysis:

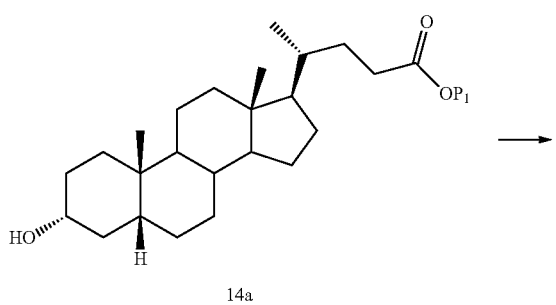

14      14a

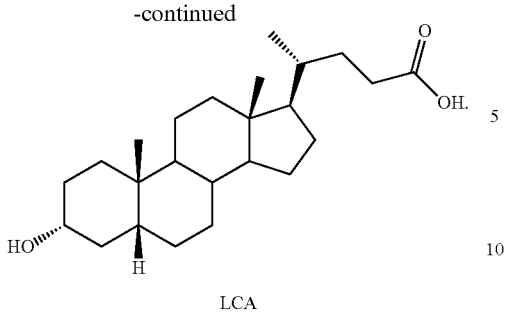

LCA

In another embodiment, the present application comprises regioselective allylic oxidation of Compound 13 to produce Compound 15 having a keto group in the C7 position:

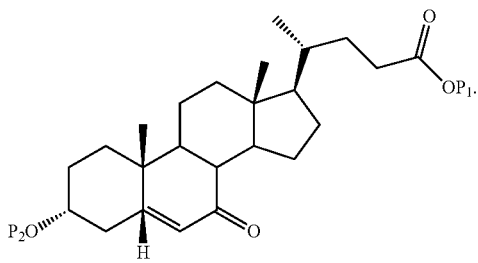

15

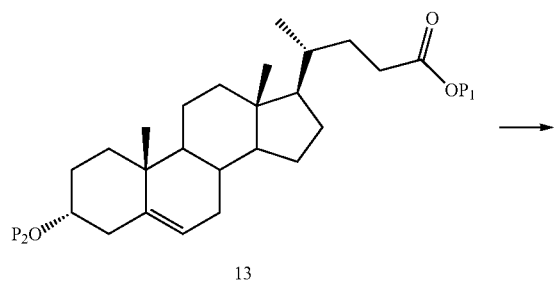

13

Compound 15 may be selectively reduced and the resultant ketone can be deprotected to afford the compound of formula (I), wherein $R_1$ is oxo.

In some embodiments, the present application further comprises the stereoselective reduction of the keto group to yield Compound 16A and/or Compound 16B. In other embodiments, the present application comprises the stereoselective reduction of the C5-C6 olefin to yield Compound 19.

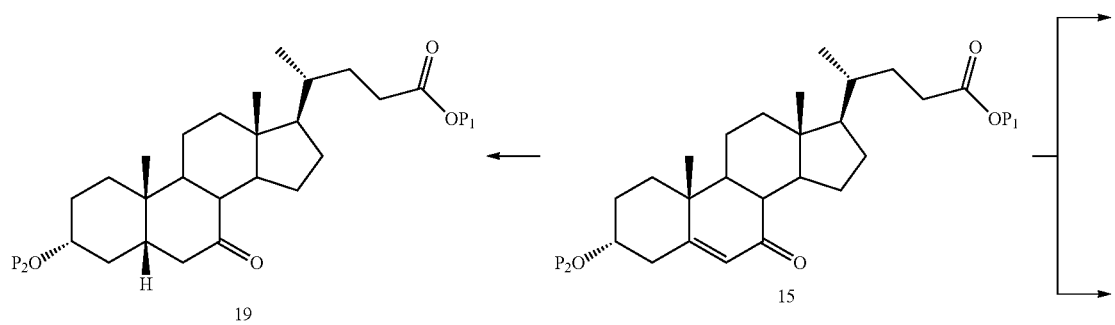

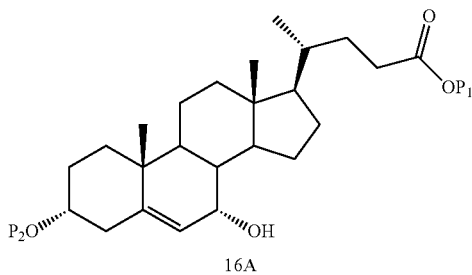

16A

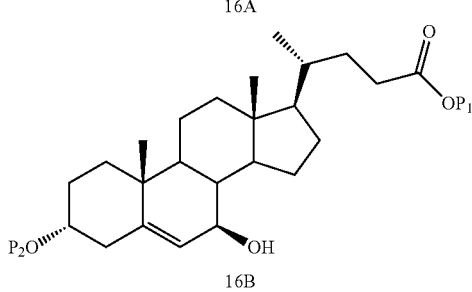

16B

The reduction of 15 to 16A produces alpha (α) stereochemistry and reduction of 15 to 16B yields beta (β) stereochemistry of the hydroxyl group at the C7 position. In some embodiments, the reduction can be carried out by hydrogenation under flow chemistry conditions.

Stereoselective reduction of 15 to 16A may be achieved by, for example, K-Selectride®, DIBAL or Red-Al®. This reduction may be achieved by alternative reducing reagents such as aluminium borohydride, sodium borohydride or dialkyl borane. The reaction may take place at a reduced temperature, e.g., −78° C., under an inert atmosphere, for example, an argon atmosphere. K-Selectride® may, for example, be added to a solution of 15 in aprotic solvent, and the reaction may be stirred. The reaction may continue for about 1 to about 5 hours, e.g., 1 hour, 1.5 hours, 2 hours, 2.5 hours, 3 hours, 3.5 hours, 4 hours, 4.5 hours, 5 hours, and any increment in between, followed by the addition of HCl.

Stereoselective reduction of 15 to 16B may be achieved by reducing 15 with $CeCl_3 \cdot 7H_2O$ and $NaBH_4$. The reaction may be performed at a reduced temperature, e.g., 0° C., and may be stirred, e.g. for about 1 hour, 1.5 hours, 2 hours, 2.5 hours, 3 hours, 3.5 hours, 4 hours, 4.5 hours, or 5 hours, and then the reaction mixture may be heated to room temperature and stirred, e.g., for about 10-20 hours, e.g., 10 hours, 10.5 hours, 11 hours, 11.5 hours, 12 hours, 12.5 hours, 13 hours, 13.5 hours, 14 hours, 14.5 hours, 15 hours, 15.5 hours, 16 hours and any increment in between.

Stereoselective reduction of the C5-C6 olefin of 15 to 19 may be achieved by reducing 15 under hydrogenation over $PtO_2$ in a protic solvent. The reaction may be performed at a reduced temperature, e.g., 0° C., and may be stirred, e.g. for about 1 hour, 1.5 hours, 2 hours, 2.5 hours, 3 hours, 3.5 hours, 4 hours, 4.5 hours, or 5 hours, and then the reaction mixture may be heated to room temperature and stirred, e.g., for about 10-20 hours, e.g., 10 hours, 10.5 hours, 11 hours, 11.5 hours, 12 hours, 12.5 hours, 13 hours, 13.5 hours, 14 hours, 14.5 hours, 15 hours, 15.5 hours, 16 hours and any increment in between. The stereoselective reduction may be carried out by hydrogenation, which can be performed using a catalyst and syngas. In certain embodiments, the reduction may be carried out by hydrogenation under flow conditions.

Following stereoselective reduction of the keto group to yield α or β stereochemistry, Compounds 16A and 16B may be selectively reduced to yield Compound 17 or Compound 18 respectively, and protecting groups $P_1$ and $P_2$ may be removed to yield a compounds of Formula (I); CDCA or UDCA, respectively. In certain embodiments, the reduction can be performed or conducted by hydrogenation under flow chemistry conditions. Alternatively, Compound 19 may be selectively reduced to afford Compound 17 or 18:

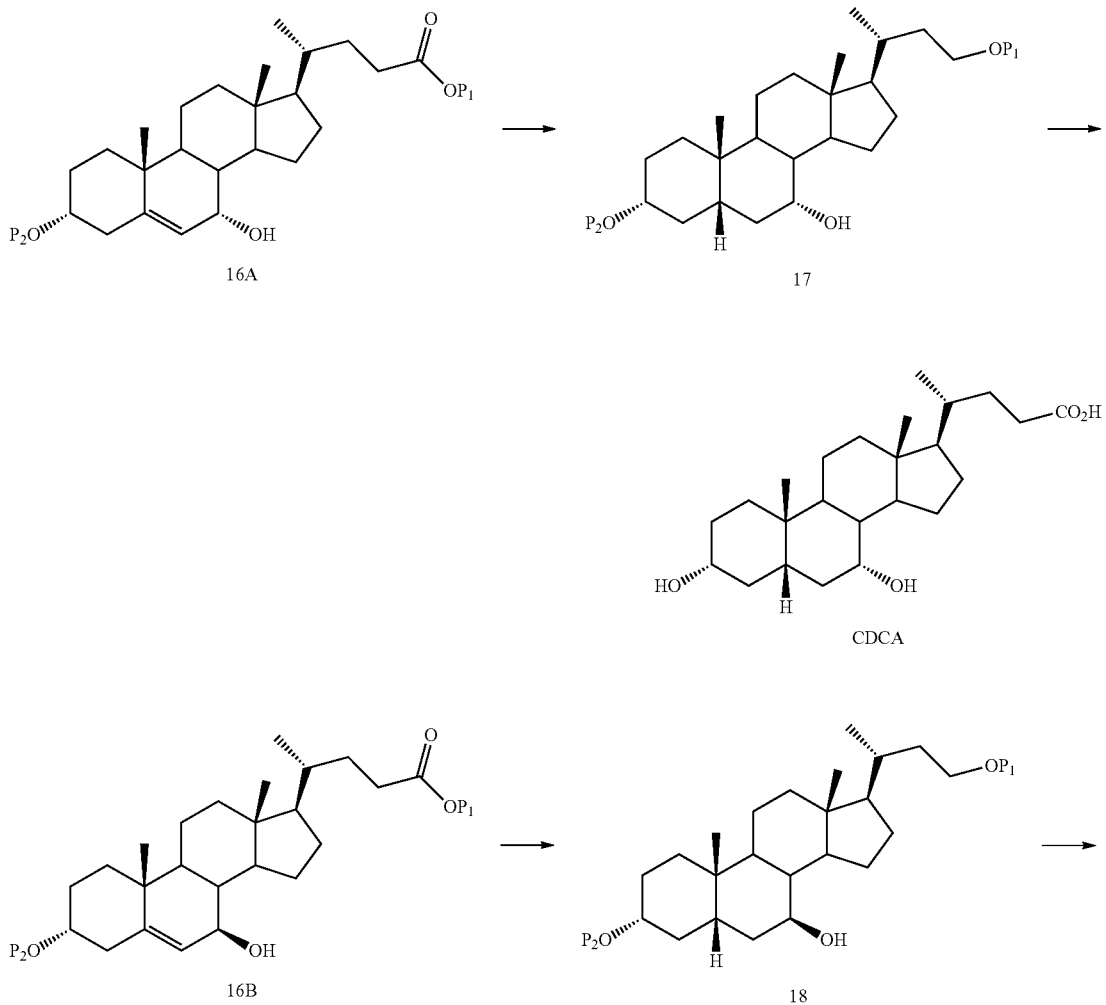

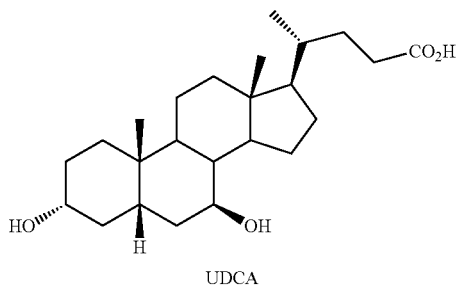

UDCA

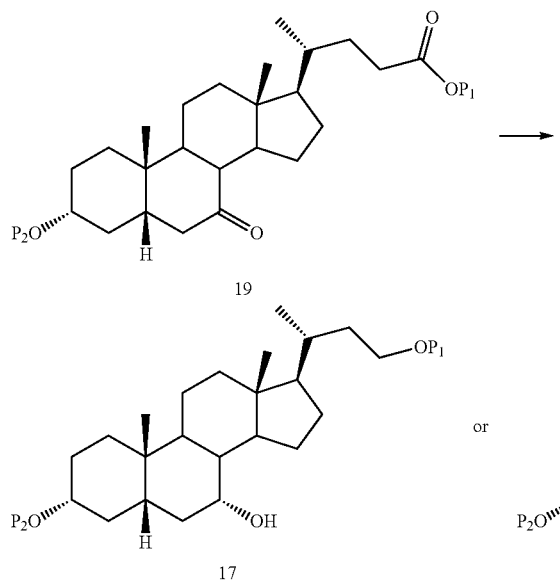

In one embodiment, Compound 17 is selectively deprotected to remove the hydroxyl group at the C3 position to yield Compound 17A:

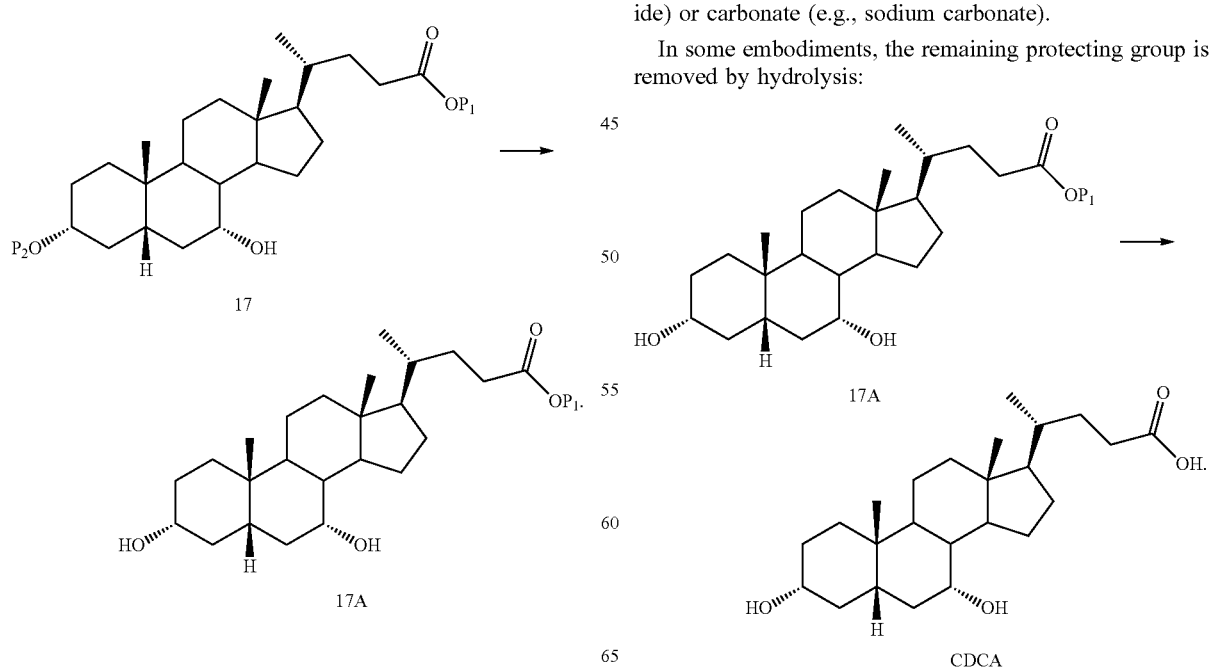

In one embodiment, deprotection is conducted under an acid condition or a basic condition. In one embodiment, deprotection is conducted under acidic conditions using an acid, such as HCl. In one embodiment, the deprotection is conducted under basic conditions using a base, such as metal hydroxide (e.g., sodium hydroxide and potassium hydroxide) or carbonate (e.g., sodium carbonate).

In some embodiments, the remaining protecting group is removed by hydrolysis:

In one embodiment, Compound 18 is selectively deprotected to remove the hydroxyl group at the C3 position to yield Compound 18A:

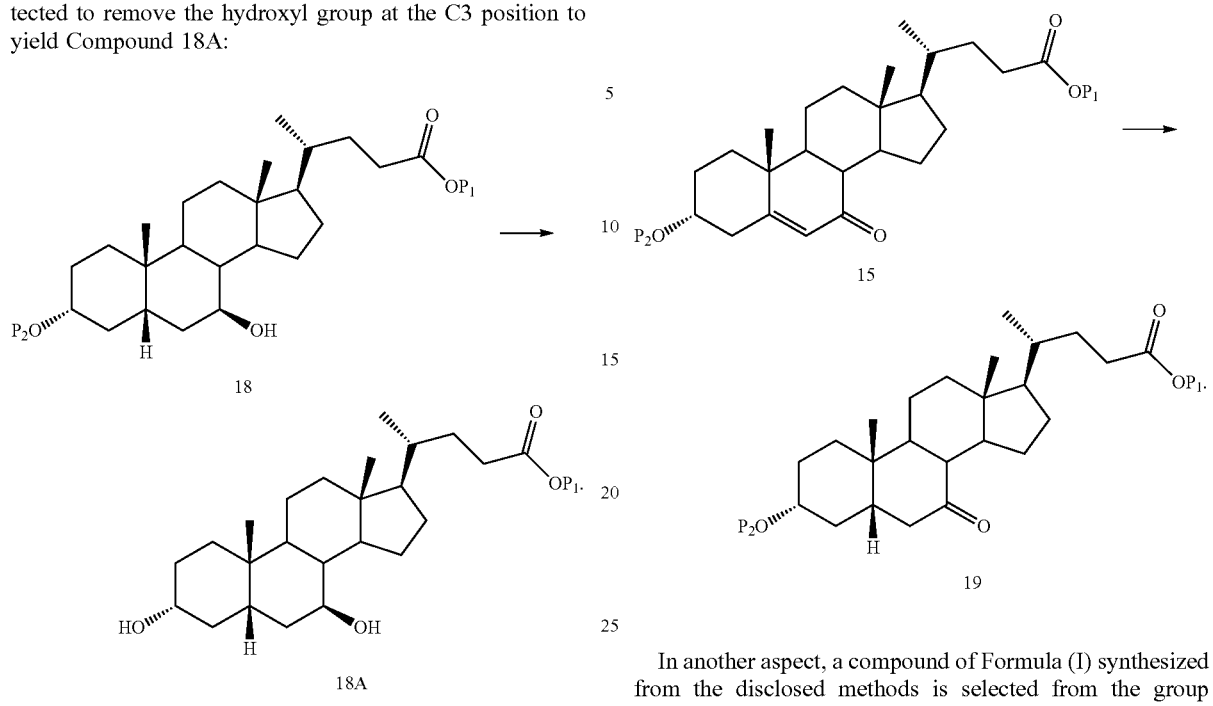

In one embodiment, deprotection is conducted under an acid condition or a basic condition. In one embodiment, deprotection is conducted under acidic conditions using an acid, such as HCl. In one embodiment, the deprotection is conducted under basic conditions using a base, such as metal hydroxide (e.g., sodium hydroxide and potassium hydroxide) or carbonate (e.g., sodium carbonate).

In some embodiments, the remaining protecting group is removed by hydrolysis:

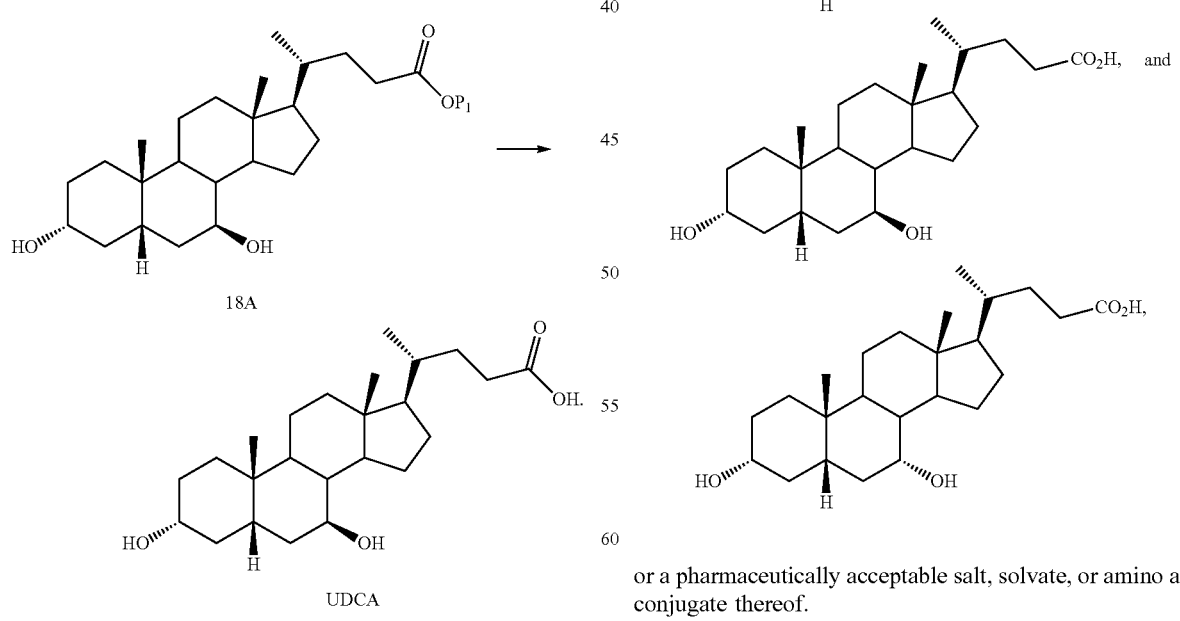

In one aspect, a process for preparing compound 19 is provided, wherein $P_1$ is H or a protecting group and $P_2$ is a protecting group, comprising selectively reducing 15 to 19,

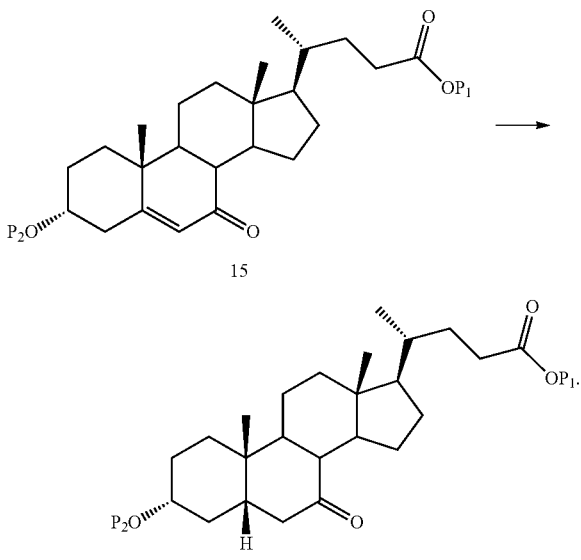

In another aspect, a compound of Formula (I) synthesized from the disclosed methods is selected from the group consisting of:

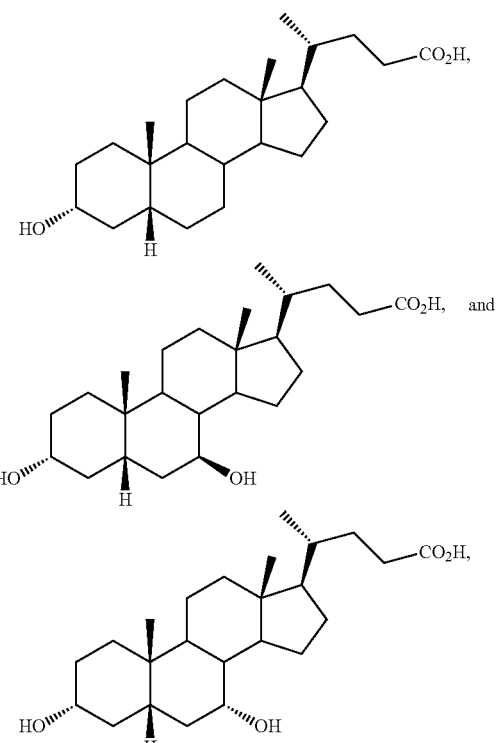

or a pharmaceutically acceptable salt, solvate, or amino acid conjugate thereof.

In one embodiment, the method of the present application is conducted at a temperature above −20° C. In one embodiment, the method of the present application is conducted at a temperature between about −20° C. to about 150° C., e.g., −20° C., −15° C., −10° C., −5° C., 0° C., 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., and any degree increment in between.
In one embodiment, the method of the present application is shown in Scheme I below:
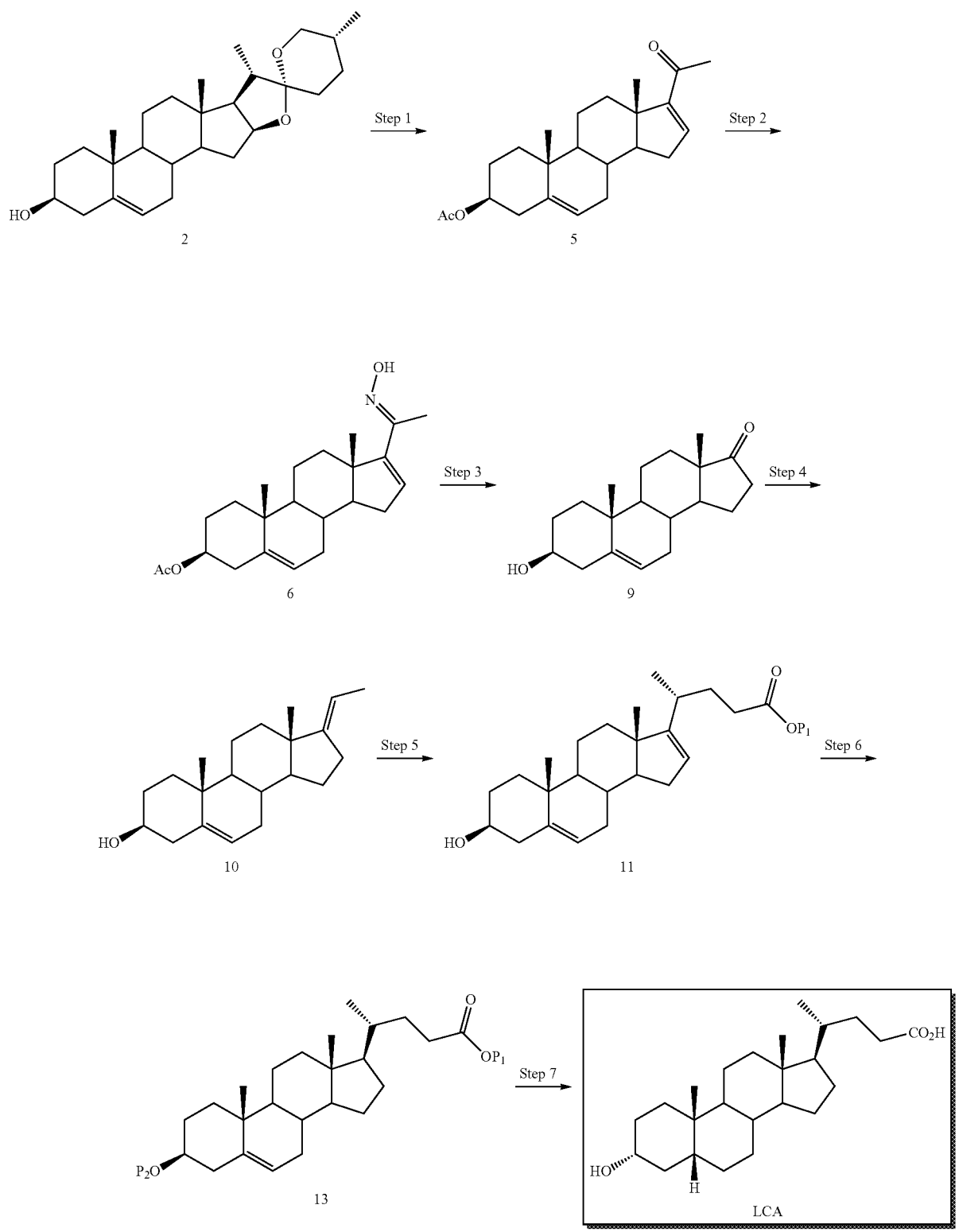

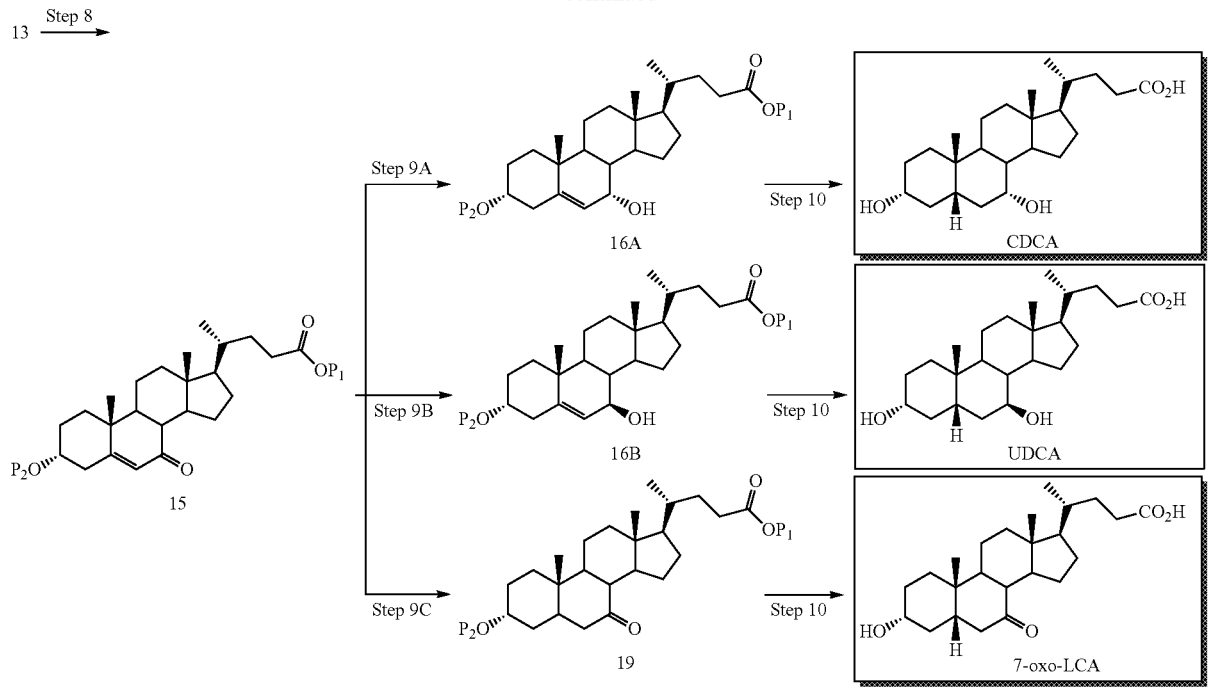

In Scheme 1, Compounds of Formula (I) are prepared in a 7-10-step synthetic process. Compound 15 is prepared in a 7-step synthetic process with the starting material diosgenin (Compound 2) and Compounds 18 and 19 are prepared in a 10-step synthetic process with starting material diosgenin (Compound 2).

In one embodiment, the method of the present application produces a compound of Formula (I), or a pharmaceutically acceptable salt, solvate, or amino acid conjugate thereof, at least 50%, at least 55%, at least 60%, at least 65%, at least 70%, at least 75%, at least 80%, at least 85%, at least 90%, or at least 95% yield. In one embodiment, the method of the present application produces a compound of Formula (I) at least 65%, at least 70%, at least 75%, at least 80%, at least 85%, at least 90%, or at least 95% yield.

In one embodiment, the method of the present application produces a substantially pure compound of Formula (I), or a pharmaceutically acceptable salt, solvate, or amino acid conjugate thereof. The term "purity" as used herein refers to the amount of compound of Formula I based on analytic methods commonly used in the art (e.g., HPLC). Purity is based on the "organic" purity of the compound, and does not include a measure of any amount of water, solvent, metal, inorganic salt, etc. In one embodiment, the purity of the compound of Formula (I) is compared to the purity of the reference standard by comparing the area under the peak in HPLC. In one embodiment, the known standard for purity is a CDCA or related acid reference standard. In one embodiment, the compound of Formula (I) has a purity of greater than about 96%. In one embodiment, the compound of Formula (I) has a purity of greater than about 98%. For example, the purity of the synthesized compound of Formula (I) is 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of the synthesized compound of Formula (I) is 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of the synthesized compound of Formula (I) is 98.0%, 98.5%, 99.0%, 99.5%, 99.6%, 99.7%, 99.8%, or 99.9%. For example, the purity of the synthesized compound of Formula (I) is 98.5%, 99.0%, or 99.5%. In one embodiment, the purity is determined by HPLC.

The present application provides methods for the synthesis of highly pure compounds of Formula (I) which is safe and which produces compounds of Formula (I) on a large scale. In one embodiment, the method of the present application produces compounds of Formula (I) in high yield (>80%) and with limited impurities.

Oral Formulation and Administration

The present application provides compounds of Formula (I) for oral administration. In one embodiment, the formulation is oral administration for the prevention and treatment of FXR and/or TGR5 mediated diseases and conditions.

Formulations suitable for oral administration may be provided as discrete units, such as tablets, capsules, cachets (wafer capsule used by pharmacists for presenting a drug), lozenges, each containing a predetermined amount of one or more compounds of Formula (I); as powders or granules; as solutions or suspensions in aqueous or non-aqueous liquids; or as oil-in-water or water-in-oil emulsions.

Formulations of the present application may be prepared by any suitable method, typically by uniformly and intimately admixing one or more compounds of Formula (I) with liquids or finely divided solid carriers or both, in the required proportions and then, if necessary, shaping the resulting mixture into the desired shape.

For example a tablet may be prepared by compressing an intimate mixture comprising a powder or granules of one or more compounds of Formula (I) and one or more optional ingredients, such as a binder, lubricant, inert diluent, or surface active dispersing agent, or by molding an intimate mixture of powdered active ingredient and inert liquid diluent.

For example, one or more tablets may be administered to get to a target dose level based on the subject's weight, e.g., a human between about 50 kg to about 100 kg.

In addition to the ingredients specifically mentioned above, the oral formulations of the present application may include other agents known to those skilled in the art of pharmacy, having regard for the type of formulation in issue. Oral formulations suitable may include flavoring agents.

In one embodiment, the present application relates to a pharmaceutical formulation of one or more compounds of Formula (I), or a pharmaceutically acceptable salt, solvate, or amino acid conjugate thereof, wherein one or more compounds of Formula (I) is produced by a process of the application. In another embodiment, the formulation is administered orally.

In one embodiment, the formulation is in tablet form. In another embodiment, the formulation comprises one or more compounds of Formula (I) and one or more components selected from microcrystalline cellulose, sodium starch glycolate, magnesium stearate, coating material, or colloidal silicon dioxide. In one embodiment, the coating material is an Opadry® coating material.

All percentages and ratios used herein, unless otherwise indicated, are by weight. The percent dimeric impurity is on an area percent basis, typically as quantified by analytical HPLC.

Pharmaceutical Compositions

Compounds of Formula (I), or pharmaceutically acceptable salts, solvates, or amino acid conjugates thereof, are useful for a variety of medicinal purposes. Compounds of Formula (I) may be used in methods for the prevention or treatment of FXR and/or TGR5 mediated diseases and conditions. In one embodiment, the disease or condition is selected from biliary atresia, cholestatic liver disease, chronic liver disease, nonalcoholic steatohepatitis (NASH), hepatitis C infection, alcoholic liver disease, primary biliary cirrhosis (PBC), liver damage due to progressive fibrosis, liver fibrosis, and cardiovascular diseases including atherosclerosis, arteriosclerosis, hypercholesteremia, and hyperlipidemia. In one embodiment, the compounds of Formula (I) may be used in methods for lowering triglycerides and/or increasing HDL. Other effects of compounds of Formula (I) include lowering alkaline phosphatase (ALP), bilirubin, ALT, AST, and GGT. In one embodiment, the present application relates to a pharmaceutical composition comprising one or more compounds of Formula (I) and a pharmaceutically acceptable carrier, wherein the one or more compounds of Formula (I), or a pharmaceutically acceptable salt, solvate, or amino acid conjugate thereof, is produced by a method of the present application.

In one embodiment, the compound or pharmaceutical composition is administered orally, parenterally, or topically. In one embodiment, the compound or pharmaceutical composition is administered orally.

In one embodiment, the present application relates to a method for inhibiting fibrosis in a subject who is suffering from a cholestatic condition, the method comprising the step of administering to the subject an effective amount of one or more compounds of Formula (I) or a pharmaceutical composition thereof, wherein the one or more compounds of Formula (I) is produced by the method of the present application. In one embodiment, the present application relates to a method for inhibiting fibrosis in a subject who is not suffering from a cholestatic condition, the method comprising the step of administering to the subject an effective amount of one or more compounds of Formula (I) or a pharmaceutical composition thereof, wherein the one or more compounds of Formula (I) is produced by the method of the present application. In one embodiment, the fibrosis to be inhibited occurs in an organ where FXR is expressed.

In one embodiment, the cholestatic condition is defined as having abnormally elevated serum levels of alkaline phosphatase, 7-glutamyl transpeptidase (GGT), and 5' nucleotidase. In another embodiment, the cholestatic condition is further defined as presenting with at least one clinical symptom. In another embodiment, the symptom is itching (pruritus). In another embodiment, the fibrosis is selected from the group consisting of liver fibrosis, kidney fibrosis, and intestinal fibrosis. In another embodiment, the cholestatic condition is selected from the group consisting of primary biliary cirrhosis, primary sclerosing cholangitis, drug-induced cholestasis, hereditary cholestasis, and intrahepatic cholestasis of pregnancy. In another embodiment, the subject is not suffering from a cholestatic condition associated with a disease or condition selected from the group consisting of primary liver and biliary cancer, metastatic cancer, sepsis, chronic total parenteral nutrition, cystic fibrosis, and granulomatous liver disease.

In one embodiment, the subject has liver fibrosis associated with a disease selected from the group consisting of hepatitis B; hepatitis C; parasitic liver diseases; post-transplant bacterial, viral and fungal infections; alcoholic liver disease (ALD); non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; $\alpha_1$-antitrypsin deficiency; Zellweger syndrome; tyrosinemia; fructosemia; galactosemia; vascular derangement associated with Budd-Chiari syndrome, veno-occlusive disease, or portal vein thrombosis; and congenital hepatic fibrosis.

In one embodiment, the subject has intestinal fibrosis associated with a disease selected from the group consisting of Crohn's disease, ulcerative colitis, post-radiation colitis, and microscopic colitis.

In one embodiment, the subject has renal fibrosis associated with a disease selected from the group consisting of diabetic nephropathy, hypertensive nephrosclerosis, chronic glomerulonephritis, chronic transplant glomerulopathy, chronic interstitial nephritis, and polycystic kidney disease.

Definitions

"Treating", includes any effect, e.g., lessening, reducing, modulating, or eliminating, that results in the improvement of the condition, disease, disorder, etc. "Treating" or "treatment" of a disease state includes: inhibiting the disease state, i.e., arresting the development of the disease state or its clinical symptoms; or relieving the disease state, i.e., causing temporary or permanent regression of the disease state or its clinical symptoms.

"Preventing" the disease state includes causing the clinical symptoms of the disease state not to develop in a subject that may be exposed to or predisposed to the disease state, but does not yet experience or display symptoms of the disease state.

"Disease state" means any disease, disorder, condition, symptom, or indication.

As used herein, the term "about" or "approximately", or the like, when used together with a numeric value, may include a range of numeric values which is more or less than the numeric value to which the term refers or relate. For example, the range can include numeric values that are from 10% less to 10% more, from 9% less to 9% more, from 8% less to 8% more, from 7% less to 7% more, from 6% less to 6% more, from 5% less to 5% more, from 4% less to 4% more, from 3% less to 3% more, from 2% less to 2% more, or from 1% less to 1% more, than the numeric value to which the term refers or relate. For example, "about 5" can include numeric values from 4.5 to 5.5, from 4.55 to 5.45, from 4.6 to 5.4, from 4.65 to 5.35, from 4.7 to 5.3, from 4.75 to 5.25, from 4.8 to 5.2, from 4.85 to 5.15, from 4.9 to 5.1, or from 4.95 to 5.05.

The term "effective amount" as used herein refers to an amount of one or more compounds of Formula (I) (e.g., an FXR-activating ligand) that produces an acute or chronic therapeutic effect upon appropriate dose administration. The effect includes the prevention, correction, inhibition, or reversal of the symptoms, signs and underlying pathology of a disease/condition (e.g., fibrosis of the liver, kidney, or intestine) and related complications to any detectable extent.

"A therapeutically effective amount" means the amount of one or more compounds of Formula (I) that, when administered to a mammal for treating a disease, is sufficient to effect such treatment for the disease. The "therapeutically effective amount" will vary depending on the disease and its severity and the age, weight, etc., of the mammal to be treated.

A therapeutically effective amount of a compound of Formula (I) can be formulated with a pharmaceutically acceptable carrier for administration to a human or an animal. Accordingly, the compounds of Formula (I) or their formulations can be administered, for example, via oral, parenteral, or topical routes, to provide an effective amount of the compound. In alternative embodiments, the compounds of Formula (I) are prepared in accordance with the present application can be used to coat or impregnate a medical device, e.g., a stent.

The application also comprehends isotopically-labelled compounds of Formula (I), or pharmaceutically acceptable salts, solvates, or amino acid conjugates thereof, which are identical to those recited in formulae of the application and following, but for the fact that one or more atoms are replaced by an atom having an atomic mass or mass number different from the atomic mass or mass number most commonly found in nature. Examples of isotopes that can be incorporated into compounds of Formula (I), or pharmaceutically acceptable salts, solvate, or amino acid conjugates thereof include isotopes of hydrogen, carbon, nitrogen, fluorine, such as $^3$H, $^{11}$C, $^{14}$C, and $^{18}$F.

Tritiated, i.e., $^3$H, and carbon-14, i.e., $^{14}$C, isotopes may be used for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be used in some circumstances, isotopically labelled compounds of Formula (I), or pharmaceutically acceptable salts, solvates, or amino acid conjugates thereof can generally be prepared by carrying out the procedures disclosed in the Schemes and/or in the Examples of the application, by substituting a readily available isotopically labelled reagent for a non-isotopically labelled reagent. However, one skilled in the art will recognize that not all isotopes can be included by substitution of the non-isotopically labelled reagent. In one embodiment, compounds of Formula (I), or pharmaceutically acceptable salts, solvates, or amino acid conjugates thereof are not isotopically labelled. In one embodiment, deuterated compounds of Formula (I) are useful for bioanalytical assays. In another embodiment, compounds of Formula (I), or pharmaceutically acceptable salts, solvates, or amino acid conjugates thereof are radiolabelled.

"Solvates" means solvent addition forms that contain either stoichiometric or non stoichiometric amounts of solvent. Compounds of Formula (I) may have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. Additionally, the compounds of the present application, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, "pharmaceutically acceptable salts" refer to derivatives of the compounds of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

As used herein, the term "metabolite", e.g., in the term "bile acid metabolites", refers to glucuronidated and sulphated derivatives of the compounds described herein, wherein one or more glucuronic acid or sulphate moieties are linked to the bile acid compounds described herein. Glucuronic acid moieties may be linked to the bile acid compounds through glycosidic bonds with the hydroxyl groups of the bile acid compounds (e.g., 3-hydroxyl and/or 7-hydroxyl). Sulphated derivatives of the bile acid compounds may be formed through sulfation of the hydroxyl groups (e.g., 3-hydroxy and/or, 7-hydroxyl, 12-hydroxyl, and/or 15-hydroxyl). Examples of bile acid metabolites include, but are not limited to, 3-O-glucuronide, 7-O-glucuronide, 3-O-7-O-glucuronide, of the bile acid compounds described herein, and 3-sulphate, 7-sulphate and 3,7-bisulphate, of the bile acid compounds described herein.

Compounds of the present application that contain nitrogens can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present application, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers" or "diastereomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold, and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

As used herein, the term "amino acid conjugates" refers to conjugates of the compounds of the application with any suitable amino acid. Taurine ($NH(CH_2)_2SO_3H$), glycine ($NHCH_2CO_2H$), and sarcosine ($N(CH_3)CH_2CO_2H$) are examples of amino acid conjugates. Suitable amino acid conjugates of the compounds have the added advantage of enhanced integrity in bile or intestinal fluids. Suitable amino acids are not limited to taurine, glycine, and sarcosine. The application encompasses amino acid conjugates of the compounds of the application.

A "pharmaceutical composition" is a formulation containing one or more compounds of Formula (I) in a form suitable for administration to a subject. In one embodiment, the pharmaceutical composition is in bulk or in unit dosage form. It is can be advantageous to formulate compositions in dosage unit form for ease of administration and uniformity of dosage. Dosage unit form as used herein refers to physically discrete units suited as unitary dosages for the subject to be treated; each unit containing a predetermined quantity of active reagent calculated to produce the desired therapeutic effect in association with the required pharmaceutical carrier. The specification for the dosage unit forms of the application are dictated by and directly dependent on the unique characteristics of the active reagent and the particular therapeutic effect to be achieved, and the limitations inherent in the art of compounding such an active agent for the treatment of individuals.

The unit dosage form is any of a variety of forms, including, for example, a capsule, an IV bag, a tablet, a single pump on an aerosol inhaler, or a vial. The quantity of one or more compounds of Formula (I) obeticholic acid (e.g., a formulation of CDCA, or a pharmaceutically acceptable salt, solvate, or amino acid conjugate thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, compounds of Formula (I) are mixed under sterile conditions with a pharmaceutically acceptable carrier, and with any preservatives, buffers, or propellants that are required.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human. In one embodiment, the subject is human child (e.g., between about 50 kg to about 100 kg). In one embodiment, the human child has had a Kasai procedure, where the Kasai procedure effectively gives them a functional bile duct when they are born either without a bile duct or one that is completely blocked at birth.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable salt" of a compound means a salt that is pharmaceutically acceptable and that possesses the desired pharmacological activity of the parent compound.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

While it is possible to administer compounds of the application directly without any formulation, compounds of Formula (I) are usually administered in the form of pharmaceutical formulations comprising a pharmaceutically acceptable excipient and one or more compounds of Formula (I). These formulations can be administered by a variety of routes including oral, buccal, rectal, intranasal, transdermal, subcutaneous, intravenous, intramuscular, and intranasal.

In one embodiment, compounds of Formula (I) can be administered transdermally. In order to administer transdermally, a transdermal delivery device ("patch") is needed. Such transdermal patches may be used to provide continuous or discontinuous infusion of a compound of the present application in controlled amounts. The construction and use of transdermal patches for the delivery of pharmaceutical agents is well known in the art. See, for example, U.S. Pat. No. 5,023,252. Such patches may be constructed for continuous, pulsatile, or on demand delivery of pharmaceutical agents.

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

The term "inhibiting" or "inhibition," as used herein, refers to any detectable positive effect on the development or progression of a disease or condition. Such a positive effect may include the delay or prevention of the onset of at least one symptom or sign of the disease or condition, alleviation or reversal of the symptom(s) or sign(s), and slowing or prevention of the further worsening of the symptom(s) or sign(s).

As used herein, a "cholestatic condition" refers to any disease or condition in which bile excretion from the liver is impaired or blocked, which can occur either in the liver or in the bile ducts. Intrahepatic cholestasis and extrahepatic cholestasis are the two types of cholestatic conditions. Intrahepatic cholestasis (which occurs inside the liver) is most commonly seen in primary biliary cirrhosis, primary sclerosing cholangitis, sepsis (generalized infection), acute alcoholic hepatitis, drug toxicity, total parenteral nutrition (being fed intravenously), malignancy, cystic fibrosis, and pregnancy. Extrahepatic cholestasis (which occurs outside the liver) can be caused by bile duct tumors, strictures, cysts, diverticula, stone formation in the common bile duct, pancreatitis, pancreatic tumor or pseudocyst, and compression due to a mass or tumor in a nearby organ.

Clinical symptoms and signs of a cholestatic condition include: itching (pruritus), fatigue, jaundiced skin or eyes, inability to digest certain foods, nausea, vomiting, pale stools, dark urine, and right upper quadrant abdominal pain. A patient with a cholestatic condition can be diagnosed and followed clinically based on a set of standard clinical laboratory tests, including measurement of levels of alkaline phosphatase, γ-glutamyl transpeptidase (GGT), 5' nucleotidase, bilirubin, bile acids, and cholesterol in a patient's blood serum. Generally, a patient is diagnosed as having a cholestatic condition if serum levels of all three of the diagnostic markers alkaline phosphatase, GGT, and 5' nucleotidase, are considered abnormally elevated. The normal serum level of these markers may vary to some degree from laboratory to laboratory and from procedure to procedure, depending on the testing protocol. Thus, a physician will be able to determine, based on the specific laboratory and test procedure, what is an abnormally elevated blood level for each of the markers. For example, a patient suffering from a cholestatic condition generally has greater than about 125 IU/L alkaline phosphatase, greater than about 65 IU/L GGT, and greater than about 17 NIL 5' nucleotidase in the blood. Because of the variability in the level of serum markers, a cholestatic condition may be diagnosed on the basis of abnormal levels of these three markers in addition to at least one of the symptoms mentioned above, such as itching (pruritus).

The term "organ" refers to a differentiated structure (as in a heart, lung, kidney, liver, etc.) consisting of cells and tissues and performing some specific function in an organism. This term also encompasses bodily parts performing a function or cooperating in an activity (e.g., an eye and related structures that make up the visual organs). The term "organ" further encompasses any partial structure of differentiated cells and tissues that is potentially capable of developing into a complete structure (e.g., a lobe or a section of a liver).

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The application having now been described by way of written description, those of skill in the art will recognize that the application can be practiced in a variety of embodiments and that the foregoing description and examples below are for purposes of illustration and not limitation of the claims that follow.

In the specification, the singular forms also include the plural, unless the context clearly dictates otherwise. Unless defined otherwise, all technical and scientific terms used herein have the same meaning as commonly understood by one of ordinary skill in the art to which this application belongs. In the case of conflict, the present specification will control.

EXAMPLES

The following examples are intended to illustrate certain embodiments of the present invention, but do not exemplify the full scope of the invention.

Example 1: Synthesis of LCA from Diosgenin

3β-acetoxy-5,16-pregnadien-20-one (5)

A suspension of diosgenin 2 (22 g, 53.06 mmol) in acetic anhydride ($Ac_2O$) (100 ml) was refluxed for 2 h. The precipitate was filtered and recrystallized from methanol. The yellow solid thus obtained was dissolved in acetic anhydride (100 mL) and diluted with water (8 mL) and acetic acid (75 mL). The mixture was cooled to 0° C. and then a solution of $CrO_3$ (15.9 g, 159 mmol) in acetic acid (50 ml) was added dropwise in 1 h. After the addition the solution was allowed to warm to room temperature and stirred for additional 5 h. Then, AcONa (13 g, 159 mmol) in water (50 mL) was added and the mixture was refluxed for 3 h. The reaction mixture was cooled to room temperature and poured into ice-water to give a sticky solid. The crude was purified by flash chromatography (Eluent: Petroleum ether/AcOEt from 100:0 (v/v) to 80:20 (v/v) to afford 3β-acetoxy-5,16-pregnadien-20-one (5) (12.86 g, 36.08 mmol, 68%). $^1$H-NMR ($CDCl_3$, 400 MHz): δ 0.99 (s, 3H, 18-$CH_3$), 1.19 (s, 3H, 19-$CH_3$), 2.01 (s, 3H, 3-$CO_2CH_3$), 4.54-4.56 (m, 1H, 3α-CH), 5.38 (d, 1H, 6-CH), 6.4 (m, 1H, 16-CH). $^{13}$C-NMR ($CDCl_3$, 100.6 MHz): 12.8, 15.2, 16.7, 20.9, 21.3, 29.0, 32.0, 34.2, 34.7, 35.1, 35.4, 35.5, 39.5, 40.5, 46.2, 55.4, 78.6, 122.9, 142.3, 144.5, 170.5, 196.3.

3β-acetoxy-5,16-pregnadien-20-oxime (6)

To a suspension of compound 5 (2.50 g, 7.0 mmol) in ethanol (15 mL), diisopropylamine (DIPA, 5.2 mL) and hydroxylamine hydrochloride (0.98 g, 14.0 mmol) were sequentially added and the resulting mixture was refluxed for 1.5 h. The reaction mixture was concentrated under reduced pressure and the residue was dissolved in $CH_2Cl_2$ and washed with $H_2O$ and brine. The organic phase was dried over anhydrous $Na_2SO_4$ and concentrated under reduced pressure. The crude was filtered on a short silica pad (Eluent: Petroleum ether/$Et_2O$ from 100:0 v/v to 80:20 v/v) to give 3β-acetoxy-5,16-pregnadien-20-oxime (6) (11.35 g, 30.55 mmol, 87%) as white solid. $^1$H-NMR ($CDCl_3$, 400 MHz): δ 0.63 (s, 3H, 18-$CH_3$), 1.02 (s, 3H, 19-$CH_3$), 2.02 (s, 3H, 3-$CO_2CH_3$), 2.19 (s, 3H, 21-$CH_3$), 4.61 (m, 1H, 3α-CH), 5.38 (d, 1H, 6-CH), 6.4 (m, 1H, 16-CH).

Dehydroepiandrosterone (9)

To a solution of 3β-acetoxy-5,16-pregnadien-20-oxime (6) (10 g, 26.92 mmol) in freshly distilled pyridine (250 mL), $POCl_3$ (10 g, 65.22 mmol) was added at 0° C. and the resulting mixture was stirred at room temperature for 3 h under argon atmosphere. The reaction mixture was poured in ice water and the resulting orange suspension was extracted with $CH_2Cl_2$. The organic phase washed with $H_2O$, brine, dried over anhydrous $Na_2SO_4$ and concentrated under reduced pressure. The yellow solid thus obtained was refluxed in 5% (w/v) of NaOH in methanol (100 mL) for 12 h. The mixture was then extracted with ethyl acetate, and the organic layer was evaporated under reduced pressure. The crude was purified by flash chromatography (Eluent: Petroleum ether/$Et_2O$ from 100:0 (v/v) to 70:30 (v/v) to give dehydroepiandrosterone (9) (5.01 g, 17.37 mmol, 64%) as white solid. $^1$H-NMR ($CDCl_3$, 400 MHz): δ 0.90 (s, 3H, 18-$CH_3$), 1.04 (s, 3H, 19-$CH_3$), 3.52-3.54 (m, 1H, 3α-CH), 5.38 (d, 1H, 6-CH). $^{13}$C-NMR ($CDCl_3$, 100.6 MHz): 13.2, 19.4, 20.4, 21.8, 30.8, 37.2, 31.5 (2×), 31.6, 35.8, 36.7, 42.2, 47.5, 50.3, 51.8, 71.4, 120.8, 141.3, 221.3.

(Z)-3β-hydroxy-pregna-5, 17(20)-diene (10)

To a suspension of ethyltriphenylphosphonium bromide (26.07 g, 70.21 mmol) in freshly distilled THF (100 mL), 1 M solution of t-BuOK in dry THF (65 mL, 65 mmol) was added dropwise in 15 min at room temperature under argon atmosphere. The orange suspension was stirred for 3 h at room temperature and then a solution of dehydroepiandrosterone (9) (5 g, 17.34 mmol) in freshly distilled THF (50 mL) was added dropwise in 15 min and the mixture was refluxed for 5 h. The reaction mixture was treated with 250 mL of 3 N HCl and extracted with $CH_2Cl_2$. The organic phase was washed with $H_2O$ and brine, dried over anhydrous $Na_2SO_4$ and concentrated under reduced pressure. The crude brown oil was filtered on a silica pad (Eluent: Petroleum ether/$Et_2O$ from 100:0 (v/v) to 70:30 (v/v) to give (Z)-3β-hydroxy-pregna-5,17(20)-diene (10) (4.79 g, 15.95 mmol, 92%) as white amorphous solid. $^1$H-NMR ($CDCl_3$, 400 MHz): δ 0.90 (s, 3H, 18-$CH_3$), 1.03 (s, 3H, 19-$CH_3$), 3.51-3.54 (m, 1H, 3-CH), 5.14 (q, J=7.2 Hz, 1H, 20-CH), 5.36 (d, J=4.9 Hz, 1H, 6-CH). $^{13}$C-NMR ($CDCl_3$, 100.6 MHz): 13.1, 16.6, 19.3, 21.2, 24.4, 31.4 (2×), 31.6, 31.7, 36.5, 37.0, 37.2, 42.2, 44.0, 50.1, 56.5, 71.7, 113.4, 121.5, 140.7, 150.2.

Ethyl 3β-hydroxy-chol-5, 16-dien-24-oate (11)

To a solution of ethyl acrylate (2.4 mL, 22.96 mmol) in freshly distilled $CH_2Cl_2$ (100 mL), 1.8 M solution of ethylaluminum dichloride in toluene (16.6 mL, 49.94 mmol) was added dropwise in 15 min at −10° C. under argon atmosphere. After 15 min, a solution of (Z)-3β-hydroxy-pregna-5,17(20)-diene (10) (3 g, 9.98 mmol in freshly distilled $CH_2Cl_2$ (30 mL) was added dropwise in 15 min at −10° C. After 30 min, the cooling bath was removed and the reaction mixture was stirred at room temperature for 3 days. The reaction mixture was quenched with $H_2O$ and extracted with $CH_2Cl_2$. The organic phase was washed with brine, dried over anhydrous $Na_2SO_4$ and concentrated under reduced pressure. The crude was purified by flash chromatography (Eluent: Petroleum ether/$Et_2O$ from 100:0 v/v to 80:20 v/v) to give ethyl 3β-hydroxy-chol-5,16-dien-24-oate (11) (3.2 g, 7.98 mmol, 80%). $^1$H-NMR ($CDCl_3$, 400 MHz): δ 0.78 (s, 3H, 18-$CH_3$), 0.98-1.06 (m, 6H, 19-$CH_3$+21-$CH_3$), 1.23 (t, J=7.1 Hz, 3H, $CO_2CH_2CH_3$), 3.50-3.54 (m, 1H, 3α-CH), 4.12 (q, J=7.1 Hz, 3H, $CO_2CH_2CH_3$), 5.33 (s, 1H, 16-CH), 5.36 (d, J=4.9 Hz, 1H, 6-CH). $^{13}$C-NMR ($CDCl_3$, 100.6 MHz): 14.2, 16.0, 19.3, 20.8, 21.9, 30.6, 31.1, 31.2, 31.6 (2×), 31.9, 32.5, 35.0, 36.7, 37.2, 42.3, 46.9, 50.7, 57.3, 60.2, 71.7, 121.3, 121.5, 141.0, 159.4, 174.0.

Ethyl 3α-benzoyloxy-chol-5-en-24-oate (13)

To a suspension of $PPh_3$ (2.0 g, 7.6 mmol) in freshly distilled THF (60 mL), DIAD (1.7 mL, 7.6 mmol) was added at 0° C. under argon atmosphere. The mixture was stirred for 30 min at this temperature and then a solution of 3β-hydroxy-chol-5,16-dien-24-oate (11) (2 g, 5 mmol) in freshly distilled THF (30 mL) was added dropwise in 10 min. After 15 min, a solution of benzoic (1.6 g, 13.11 mmol) acid in freshly distilled THF (50 mL) was added dropwise over 10 min at 0° C. The solution turned from pale yellow to in colour. The reaction mixture was allowed to warm to room temperature and stirred for additional 6 h. The reaction mixture was concentrated under reduced pressure and the residue was dissolved in $CH_2Cl_2$ and washed with $H_2O$, brine, dried over anhydrous $Na_2SO_4$ and concentrated under reduced pressure. The crude oil thus obtained was dissolved in AcOEt (100 mL) and hydrogenated in a Parr apparatus at 25 psi in presence of 5% Pt/C (700 mg) for 2 h. The reaction mixture was filtered on a celite pad and concentrated under reduced pressure. The crude was purified by flash chromatography (cyclohexane/$Et_2O$ from 100:0 to 80:20 v/v) affording ethyl 3α-benzoyloxy-chol-5-en-24-oate (13) (2.9 g, 5.07 mmol, yield 66%) as colourless oil. $^1$H-NMR ($CDCl_3$, 400 MHz): δ 0.68 (s, 3H, 18-$CH_3$), 0.92 (d, J=6.4 Hz, 3H, 21-$CH_3$), 1.05 (s, 3H, 19-$CH_3$), 1.23 (t, J=7.1 Hz, 3H, $CO_2CH_2CH_3$), 2.19-2.23 (m, 1H), 2.31-2.36 (m, 2H), 2.53-2.61 (m, 1H), 4.11 (q, J=7.1 Hz, 3H, $CO_2CH_2CH_3$), 5.24 (s, 1H, 3β-CH), 5.31 (d, J=5 Hz, 1H, 6-CH), 7.41 (t, J=7.8 Hz, 2H, m-$C_6H_5$), 7.52 (t, J=7.4 Hz, 1H, p-$C_6H_5$), 7.98 (d, J=7.3 Hz, 2H, o-$C_6H_5$). $^{13}$C-NMR ($CDCl_3$, 100.6 MHz): 11.8, 14.2, 15.2, 18.2, 18.9, 20.7, 24.1, 26.3, 28.0, 30.9 (2×), 31.2, 31.7, 31.8, 33.9, 35.3, 36.5, 37.0, 39.6, 42.3, 50.1, 55.7, 56.6, 60.1, 65.8, 71.1, 122.2, 128.2, 129.4, 129.5, 129.9, 131.0, 132.6, 138.3, 165.9, 174.3.

3α-hydroxy-5β-cholan-24-oic acid (LCA)

A solution of ethyl 3α-benzoyloxy-chol-5-en-24-oate (13) (100 mg, 0.197 mmol) in EtOH/AcOH (5 mL, 50:1 v/v), was hydrogenated over 10% Pd/C (20 mg) in a Parr apparatus at 55 psi for 24 h. The suspension was filtered on a celite pad, concentrated under reduced pressure and refluxed with 5% (w/v) NaOH in methanol (5 mL) for 18 h. The reaction mixture was acidified with 3 N HCl (pH 2) and extracted with $CH_2Cl_2$. The organic phase was washed with brine, dried over anhydrous $Na_2SO_4$ and concentrated under reduced pressure. The crude was purified by flash chromatography (Eluent: $CHCl_3$/iPrOH from 100:0 (v/v) to 95:5 (v/v)+0.1% AcOH) to give 3α-hydroxy-5β-cholan-24-oic acid (LCA) (54 mg, 0.142 mmol, 68%). $^1$H-NMR ($CD_3OD$, 400 MHz): δ 0.70 (s, 3H, 18-$CH_3$), 0.93 (s, 3H, 19-$CH_3$), 0.96 (d, J=6.5 Hz, 3H, 21-$CH_3$), 3.31-3.37 (m, 1H, 3β-CH). $^{13}$C-NMR ($CD_3OD$, 100.6 MHz): 10.7, 17.4, 20.3, 22.0, 23.2, 27.8, 29.9, 30.5, 30.8, 30.9, 32.6, 34.4, 34.8, 35.1, 35.3, 39.0, 39.3, 39.6, 41.7, 42.2, 50.1, 55.9, 71.4 176.7.

Example 2: 3α,7α-dihydroxy-5β-cholan-24-oic acid (CDCA)

Ethyl 3α-benzoyloxy-chol-5-en-24-oate (13) was prepared in accordance with Example 1.

Ethyl 3α-benzoyloxy-7-keto-chol-5-en-24-oate (15)

To a solution of ethyl 3α-benzoyloxy-chol-5-en-24-oate (7) (300 mg, 0.60 mmol) in EtOAc (3 mL), t-BuOOH (aqueous solution 80% w/w, 0.93 mL) and NaClO (aqueous solution 8% w/w, 1.5 mL) were sequentially added at −5° C. The resulting mixture was stirred at room temperature for 16 h. The crude was quenched with a saturated aqueous solution of $NaHCO_3$ (20 mL), extracted with EtOAc (3×10 mL), washed with brine, concentrated under vacuum and purified by flash chromatography (Eluent: Petroleum ether/$Et_2O$ from 100:0 (v/v) to 85:15 (v/v) to give ethyl 3α-benzoyloxy-7-keto-chol-5-en-24-oate (9) (222 mg, 0.43 mmol, 72%). $^1$H-NMR ($CDCl_3$, 400 MHz): δ 0.70 (s, 3H, 18-$CH_3$), 0.94 (d, J=6.4 Hz, 3H, 21-$CH_3$), 1.06 (s, 3H, 19-$CH_3$), 1.23 (t, J=7.1 Hz, 3H, $CO_2CH_2CH_3$), 4.11 (q, J=7.1 Hz, 3H, $CO_2CH_2CH_3$), 5.24 (s, 1H, 3β-CH), 5.45-5.75 (m, 1H, 6-CH), 7.40 (t, J=7.8 Hz, 2H, m-$C_6H_5$), 7.53 (t, J=7.4 Hz, 1H, p-$C_6H_5$), 7.97 (d, J=7.3 Hz, 2H, o-$C_6H_5$). $^{13}$C-NMR ($CDCl_3$, 100.6 MHz): 11.8, 14.2, 15.2, 18.2, 18.9, 20.7, 24.1, 26.3, 28.0, 30.9 (2×), 31.2, 31.7, 31.8, 33.9, 35.3, 36.5, 37.0, 39.6, 42.3, 50.1, 55.7, 56.6, 60.1, 65.8, 70.9, 122.2, 128.2, 129.4, 129.5, 129.9, 131.2, 132.8, 138.1, 165.6, 174.3, 202.8.

Ethyl 3α-benzoyloxy-7α-hydroxy-chol-5-en-24-oate (16A)

To a solution of ethyl 3α-benzoyloxy-7-keto-chol-5-en-24-oate (15) (300 mg, 0.576 mmol) in freshly distilled THF (8 mL), 1 M solution of K-Selectride in THF (4 mL, 4 mmol) was added dropwise in 10 min at −78° C. under argon atmosphere. The reaction mixture was stirred for 4 h at −78° C. and then 3 N HCl was slowly added. The reaction mixture was extracted with $CH_2Cl_2$ and the organic layers were washed with $H_2O$, brine, dried over anhydrous $Na_2SO_4$ and concentrated under reduced pressure. The crude was purified by flash chromatography (Eluent: Petroleum ether/AcOEt from 100:0 v/v to 70:30 v/v) to give ethyl 3α-benzoyloxy-7α-hydroxy-chol-5-en-24-oate (16A) (192 mg, 0.368 mmol, 64%). $^1$H-NMR ($CDCl_3$, 400 MHz): δ 0.70 (s, 3H, 18-$CH_3$), 0.96 (d, J=6.2 Hz, 3H, 21-$CH_3$), 1.09 (s, 3H, 19-$CH_3$), 1.25 (t, J=7.1 Hz, 3H, $CO_2CH_2CH_3$), 3.94 (brs, 1H, 7β-CH), 4.12 (q, J=7.2 Hz, 3H, $CO_2CH_2CH_3$), 5.24 (m, 1H, 3β-CH), 5.60 (d, J=2 Hz, 1H, 6-CH), 7.42 (t, J=7.8 Hz, 2H, m-$C_6H_5$), 7.56 (t, J=7.4 Hz, 1H, p-$C_6H_5$), 7.98 (d, J=7.3 Hz, 2H, o-$C_6H_5$). $^{13}$C-NMR ($CDCl_3$, 100.6 MHz): 11.8, 14.2, 18.4, 18.7, 20.8, 26.2, 26.3, 28.4, 31.0, 31.3, 33.6, 35.3, 36.1, 37.0, 39.5, 40.7, 42.9, 48.3, 55.1, 55.9, 60.2, 70.7, 73.1, 126.2, 128.3, 129.5, 130.9, 132.7, 141.3, 165.8, 174.3.

3α,7α-dihydroxy-5β-cholan-24-oic acid (CDCA)

A solution of ethyl 3α-benzoyloxy-7α-hydroxy-chol-5-en-24-oate (16A) (150 mg, 0.287 mmol) in EtOH/AcOH (7 mL, 50:1 v/v), was hydrogenated over 10% Pd/C (30 mg) in a Parr apparatus at 55 psi for 24 h. The suspension was filtered on a celite pad, concentrated under reduced pressure and refluxed with 5% (w/v) NaOH in methanol (5 mL) for 18 h. The reaction mixture was acidified with 3 N HCl (pH 2) and extracted with $CH_2Cl_2$. The organic phase was washed with brine, dried over anhydrous $Na_2SO_4$ and concentrated under reduced pressure. The crude was purified by flash chromatography (Eluent: $CHCl_3$/MeOH from 100:0 (v/v) to 93:7 (v/v)+0.1% AcOH) to give 3α,7α-dihydroxy-5β-cholan-24-oic acid (CDCA) (92 mg, 0.234 mmol, 82%). $^1$H-NMR (CD$_3$OD, 400 MHz): δ 0.70 (s, 3H, 18-CH$_3$), 0.93 (s, 3H, 19-CH$_3$), 0.96 (d, J=6.6 Hz, 3H, 21-CH$_3$), 3.35-3.38 (m, 1H, 3β-CH), 3.80 (s, 1H, 7β-CH). $^{13}$C-NMR (CD$_3$OD, 100.6 MHz): 10.7, 17.4, 20.4, 22.0, 23.2, 27.8, 29.9, 30.5, 30.9, 32.6, 34.4, 34.8, 35.1, 35.4, 39.0, 39.3, 39.6, 41.8, 42.2, 50.1, 55.9, 67.6, 71.4, 176.8.

Example 3: Synthesis of 3α,7β-dihydroxy-5β-cholan-24-oic acid (UDCA)

Ethyl 3α-benzoyloxy-7-keto-chol-5-en-24-oate (15) was prepared in accordance with Example 2.

Ethyl 3α-benzoyloxy-7β-hydroxy-chol-5-en-24-oate (16B)

To a solution of ethyl 3α-benzoyloxy-7-keto-chol-5-en-24-oate (15) (200 mg, 0.384 mmol) in MeOH/$CH_2Cl_2$ (3:1 v/v, 3 mL), CeCl$_3$.7H$_2$O (15 μL, 0.384 mmol) and NaBH$_4$ (59 mg, 1.536 mmol) were sequentially added at 0° C. and the reaction mixture was stirred for 2 h at 0° C. and for additional 16 h at room temperature. The reaction mixture was quenched with H$_2$O, extracted with $CH_2Cl_2$. The organic phase was washed with H$_2$O, brine, dried over anhydrous Na$_2$SO$_4$ and concentrated under reduced pressure. The crude was filtered on a short silica pad (Eluent: Petroleum ether/AcOEt from 100:0 (v/v) to 70:30 (v/v) to give ethyl 3α-benzoyloxy-7β-hydroxy-chol-5-en-24-oate (16B) (184 mg, 0.351 mmol, 92%). $^1$H-NMR (CDCl$_3$, 400 MHz): δ 0.71 (s, 3H, 18-CH$_3$), 0.94 (d, J=6.2 Hz, 3H, 21-CH$_3$), 1.09 (s, 3H, 19-CH$_3$), 1.25 (t, J=7.1 Hz, 3H, CO$_2$CH$_2$CH$_3$), 2.56-2.65 (m, 1H), 3.90 (d, J=7.6 Hz, 1H, 7α-CH), 4.12 (q, J=7.2 Hz, 3H, CO$_2$CH$_2$CH$_3$), 5.28 (s, 2H, 3β-CH+6-CH), 7.42 (t, J=7.8 Hz, 2H, m-C$_6$H$_5$), 7.56 (t, J=7.4 Hz, 1H, p-C$_6$H$_5$), 7.98 (d, J=7.3 Hz, 2H, o-C$_6$H$_5$). $^{13}$C-NMR (CDCl$_3$, 100.6 MHz): 11.8, 14.2, 18.4, 18.7, 20.8, 26.2, 26.3, 28.4, 31.0, 31.3, 33.6, 35.3, 36.1, 37.0, 39.5, 40.7, 42.9, 48.3, 55.1, 55.9, 60.2, 70.7, 73.1, 126.2, 128.3, 129.5, 130.9, 132.7, 141.3, 165.8, 174.3.

3α,7β-dihydroxy-5β-cholan-24-oic acid (UDCA)

A solution of ethyl 3α-benzoyloxy-7α-hydroxy-chol-5-en-24-oate (16B) (150 mg, 0.287 mmol) in EtOH/AcOH (7 mL, 50:1 v/v), was hydrogenated over 10% Pd/C (30 mg) in a Parr apparatus at 55 psi for 24 h. The suspension was filtered on a celite pad, concentrated under reduced pressure and refluxed with 5% (w/v) NaOH in methanol (5 mL) for 18 h. The reaction mixture was acidified with 3 N HCl (pH 2) and extracted with $CH_2Cl_2$. The organic phase was washed with brine, dried over anhydrous Na$_2$SO$_4$ and concentrated under reduced pressure. The crude was purified by flash chromatography (Eluent: $CHCl_3$/MeOH+0.1% AcOH) to give 3α,7β-dihydroxy-5β-cholan-24-oic acid (UDCA) (78 mg, 0.20 mmol, 71%). $^1$H-NMR (CD$_3$OD, 400 MHz): δ 0.72 (s, 3H, 18-CH$_3$), 0.96-0.98 (m, 6H, 19-CH$_3$+21-CH$_3$), 3.46-3.51 (m, 2H, 3β-CH+7α-CH). $^{13}$C-NMR (CD$_3$OD, 100.6 MHz): 11.3, 17.5, 21.0, 22.6, 26.5, 28.2, 30.6, 31.0, 32.2, 33.8, 34.7, 35.3, 37.2, 38.0, 39.3, 40.2, 42.6, 43.1, 43.4, 55.1, 56.1, 70.5, 70.7, 176.8.

Example 4: Synthesis of 3α-hydroxy-7-keto-5β-cholan-24-oic acid (7-KLCA)

Ethyl 3α-benzoyloxy-7-keto-chol-5-en-24-oate (15) was prepared in accordance with Example 2.

3α-Hydroxy-7-keto-5β-cholan-24-oic acid (7-KLCA)

A solution of ethyl 3α-benzoyloxy-7-keto-chol-5-en-24-oate (15) (650 mg, 1.3 mmol) in i-PrOH (30 mL) was hydrogenated over PtO$_2$ (65 mg) for 6 h. The suspension was filtered on a celite pad and concentrated under reduced pressure. The crude residue was treated with 5% w/v NaOH in MeOH (10 mL) at room temperature overnight. The reaction mixture was diluted with H$_2$O (100 mL) and washed with Et$_2$O (2×100 mL). The aqueous phase was acidified with 3 N HCl (pH=4) and extracted with $CH_2Cl_2$. The organic phase was washed with H$_2$O, brine, dried over anhydrous Na$_2$SO$_4$ and concentrated under reduced pressure to give 460 mg of the desired product. $^1$H-NMR (CD$_3$OD, 400 MHz): δ 0.71 (s, 3H, 18-CH$_3$), 0.97 (d, J=6.49 Hz, 2H, 21-CH$_3$), 1.22 (s, 3H, 18-CH$_3$), 2.54 (t, J=11.39 Hz, 1H, 6-CH$_a$), 2.98 (dd, J$_1$=5.97, J$_2$=12.38, 6-CH$_b$), 3.52 (brm, 1H, 3-CH). $^{13}$C-NMR (CD$_3$OD, 100.6 MHz): δ 11.1, 17.4, 21.4, 22.1, 24.4, 27.9, 29.2, 30.6, 30.9, 33.7, 34.9, 35.2, 36.8, 38.9, 42.4, 43.0, 45.0, 46.1, 49.0, 49.2, 54.8, 70.0, 176.7, 213.7.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A method of preparing a compound of Formula (I):

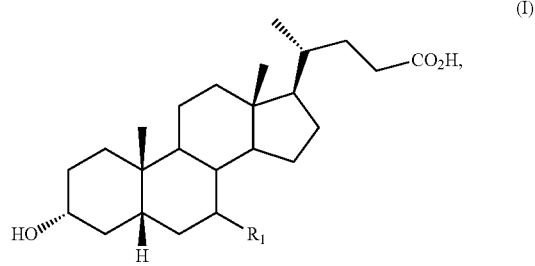

or a pharmaceutically acceptable salt, solvate, or amino acid conjugate thereof, wherein R$_1$ is H, α-OH, β-OH, or an oxo group, from compound 2 comprising the steps of:

(1) converting compound 2 to compound 5
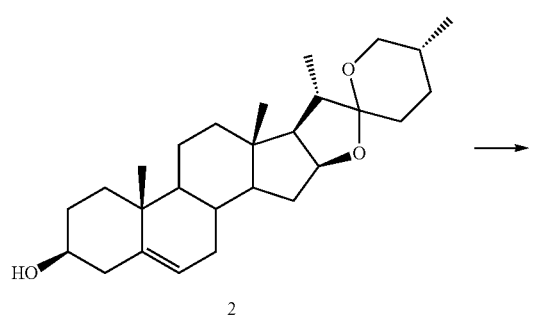
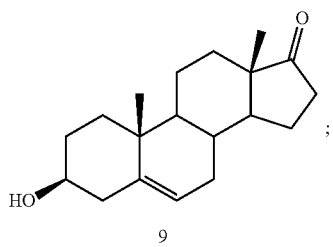
(4) converting compound 9 into compound 10
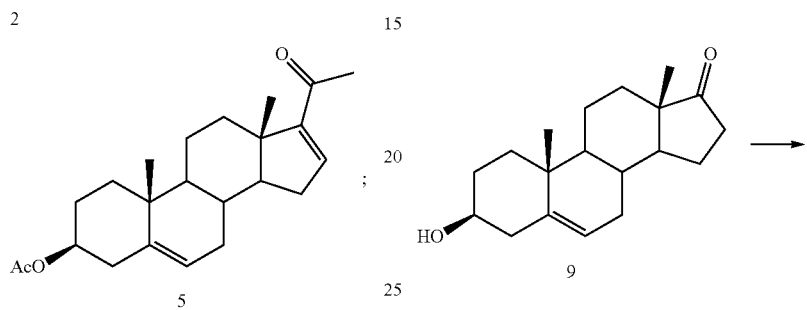
(2) converting compound 5 into compound 6:
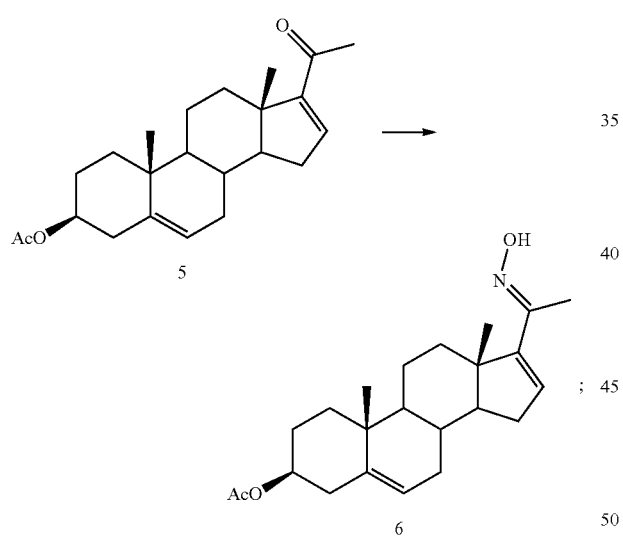
(5) alkylating compound 10 regioselectively and stereoselectively to yield compound 11
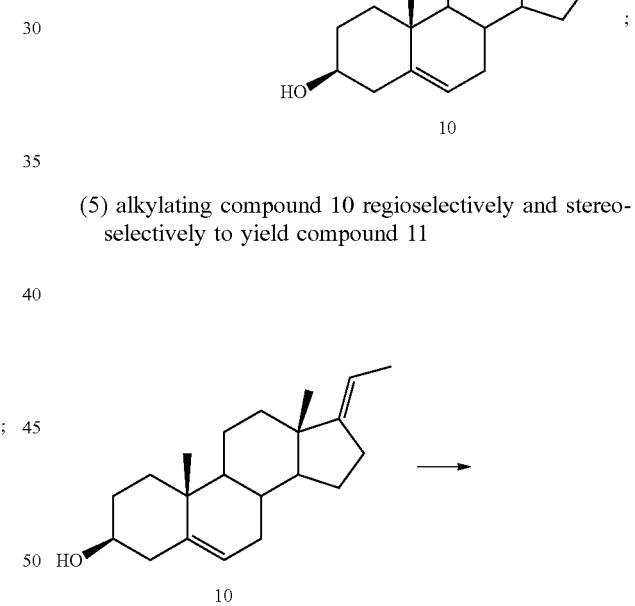
(3) converting compound 6 into compound 9:
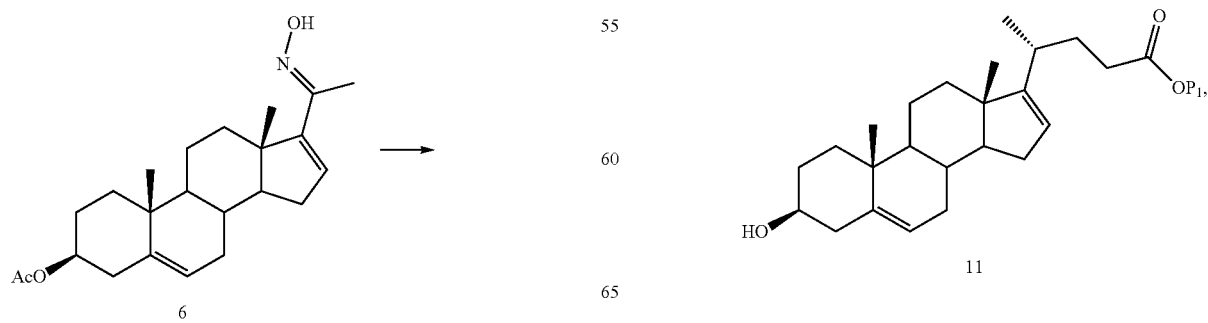
wherein $P_1$ is a protecting group or H;

(6) regioselectively and stereoselectively reducing compound 11 to yield compound

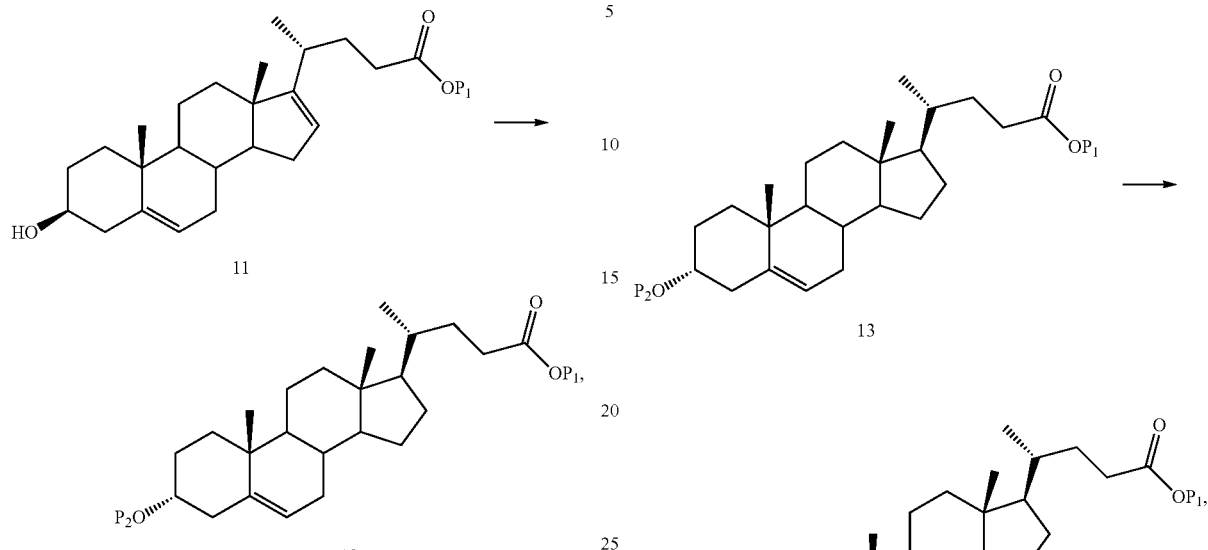

wherein $P_2$ is a protecting group; and (7) selectively reducing compound 13 and deprotecting to yield the compound of Formula (I), wherein $R_1$ is H; or (8) oxidizing compound 13 regioselectively to yield compound 15

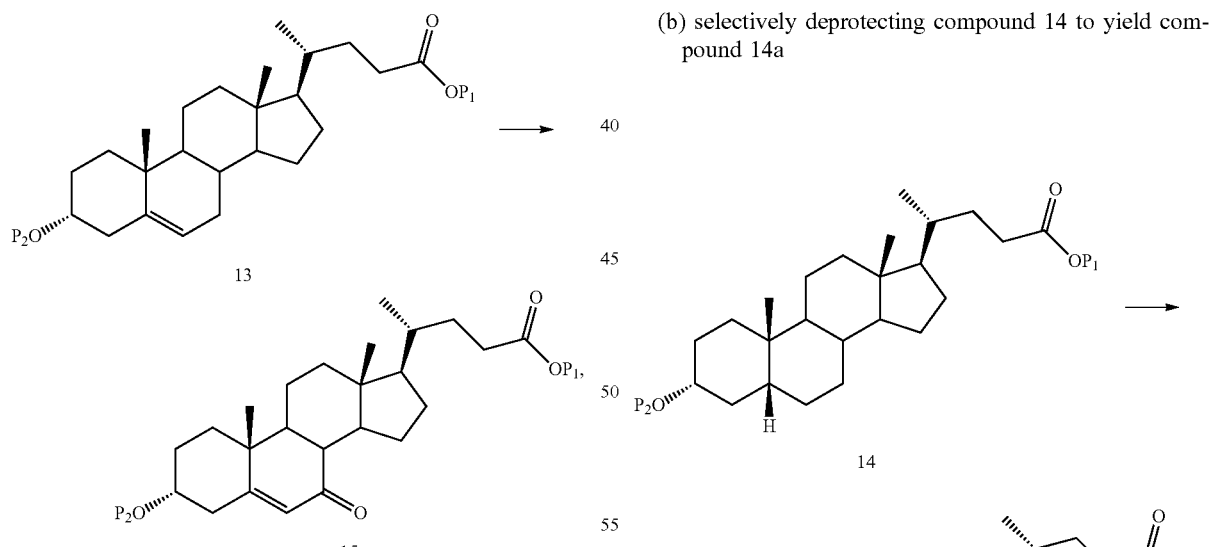

and (9) selectively reducing compound 15 and deprotecting to yield the compound of Formula (I), wherein $R_1$ is α-OH, β-OH, or an oxo group.

2. The method of claim 1, where in the compound of Formula (I) is a compound of Formula (Ia) or a pharmaceutically acceptable salt, solvate, or amino acid conjugate thereof, further comprising the steps of:

(a) stereoselectively reducing compound 13 to yield compound 14

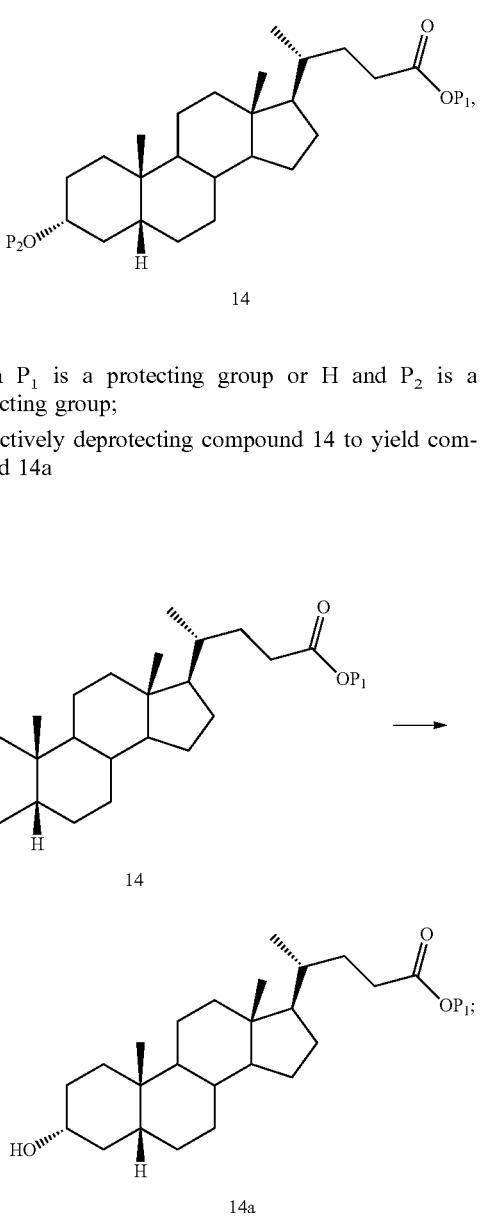

wherein $P_1$ is a protecting group or H and $P_2$ is a protecting group;

(b) selectively deprotecting compound 14 to yield compound 14a and (c) hydrolyzing compound 14a to form the compound of Formula (Ia)

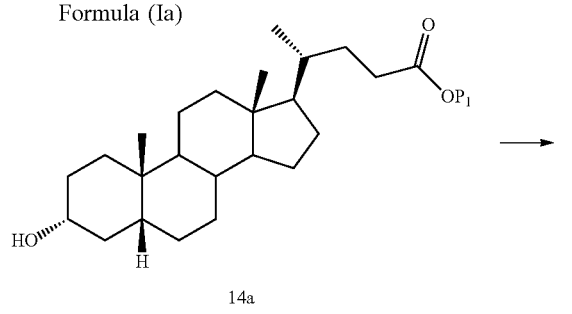

14a (Ia)

3. The method of claim 2, wherein the deprotecting in step b) and the hydrolyzing in step c) occur in a single step.

4. The method of claim 2, wherein the stereoselective reduction in step a) comprises hydrogenation.

5. The method of claim 4, wherein the hydrogenation is conducted with a catalyst and hydrogen gas.

6. The method of claim 1, wherein the compound of Formula (I) is a compound of Formula (Ib) or a pharmaceutically acceptable salt, solvate, or amino acid conjugate thereof, further comprising the steps of:

(9a) stereoselectively reducing compound 15 to yield compound 16A

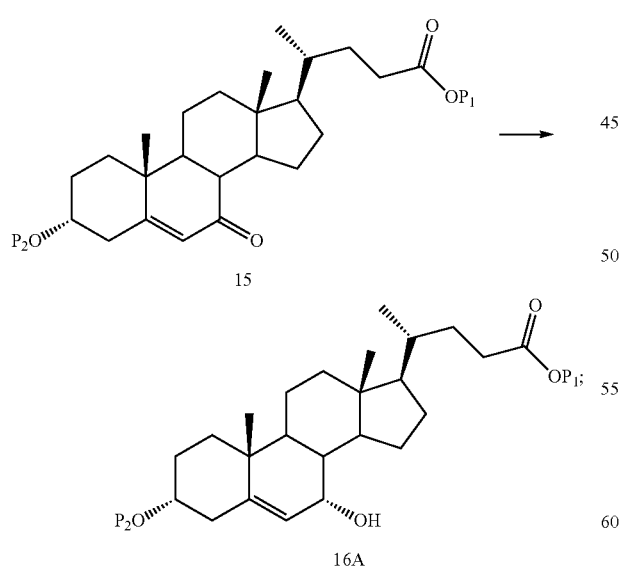

15

16A and

(10) stereoselectively reducing compound 16A and deprotecting to yield the compound of Formula (Ib), wherein step 10 comprises the steps of (a) stereoselectively reducing compound 16A to yield compound 17

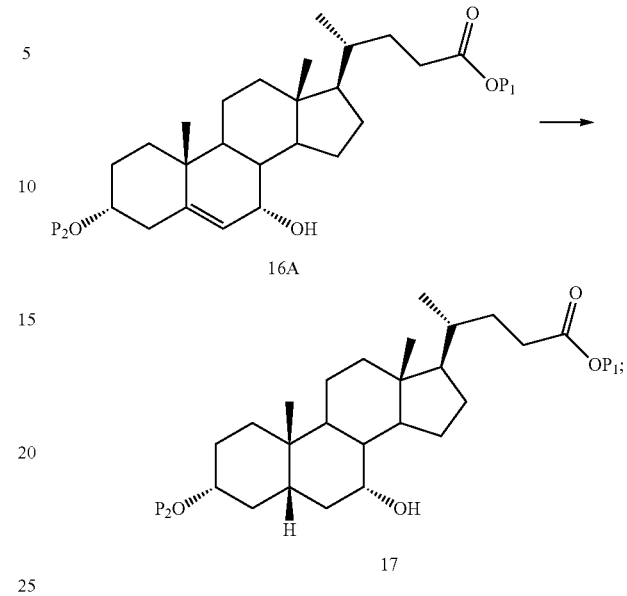

16A

17

(b) selectively deprotecting compound 17 to yield compound 17A

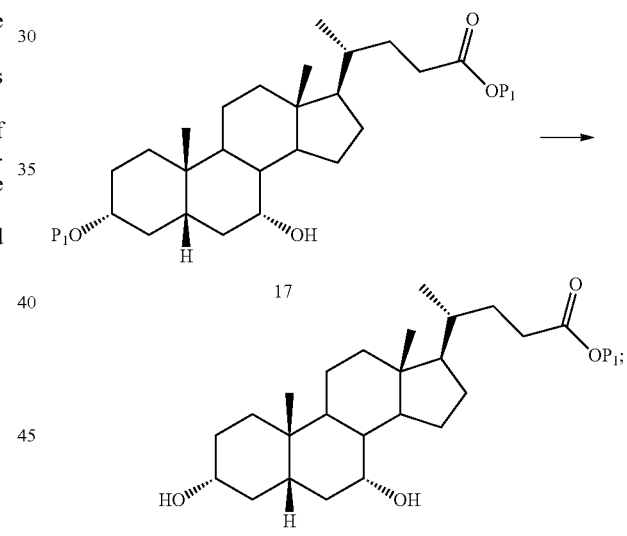

17

17A and (c) hydrolyzing compound 17A to yield the compound of Formula (Ib)

17A

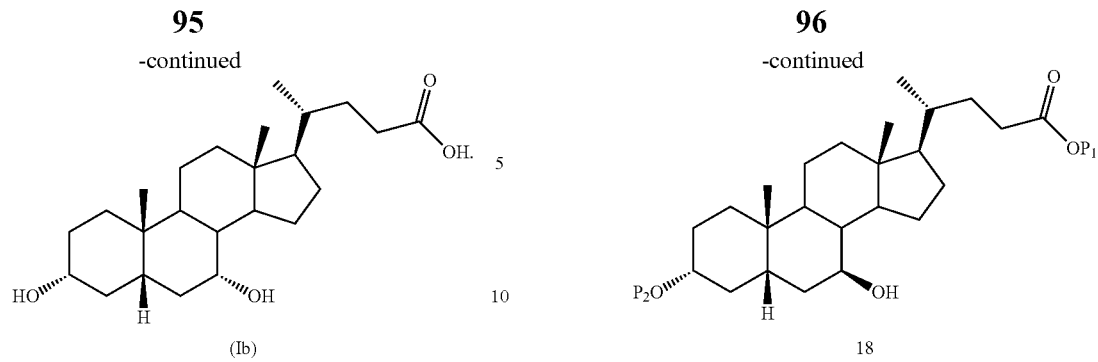

(Ib)

7. The method of claim 6, wherein the deprotecting in step b) and the hydrolyzing in step c) occur in a single step.

8. The method of claim 6, wherein the stereoselective reduction comprises hydrogenation.

9. The method of claim 8, wherein the hydrogenation is conducted with a catalyst and hydrogen gas.

10. The method of claim 1, where in the compound of Formula (I) is a compound of Formula (Ic) or a pharmaceutically acceptable salt, solvate, or amino acid conjugate thereof, further comprising the steps of:

(9b) stereoselectively reducing compound 15 to yield compound 16B

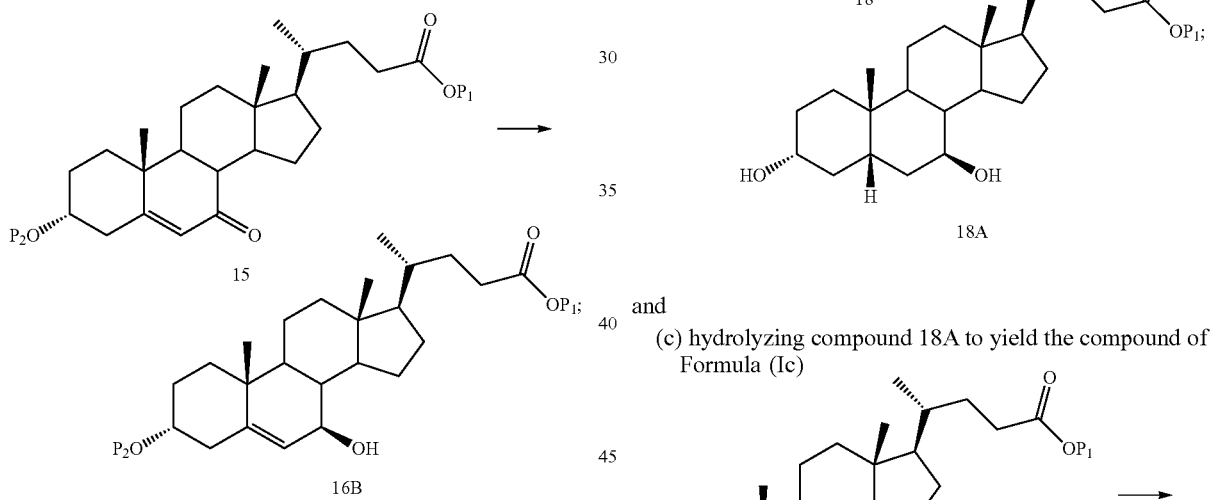

(10) stereoselectively reducing compound 16B and deprotecting to yield the compound of Formula (Ic), wherein step 10 comprises the steps of (a) stereoselectively reducing compound 16B to yield compound 18

(b) deprotecting compound 18 to yield compound 18A and (c) hydrolyzing compound 18A to yield the compound of Formula (Ic)

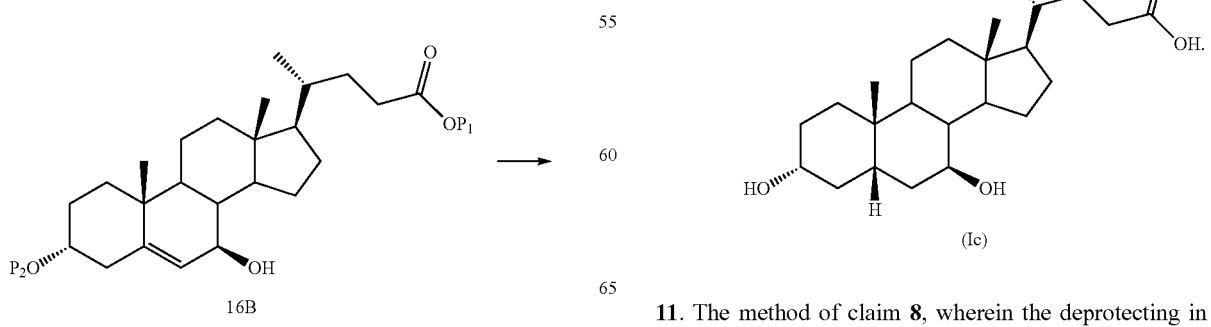

(Ic)

11. The method of claim 8, wherein the deprotecting in step b) and the hydrolyzing in step c) occur in a single step.

12. The method of claim 11, wherein the stereoselective reduction comprises hydrogenation.

13. The method of claim 12, wherein the hydrogenation is conducted with a catalyst and hydrogen gas.

14. The method of claim 1 further comprising the steps of:
(9c) selectively reducing compound 15 to compound 19

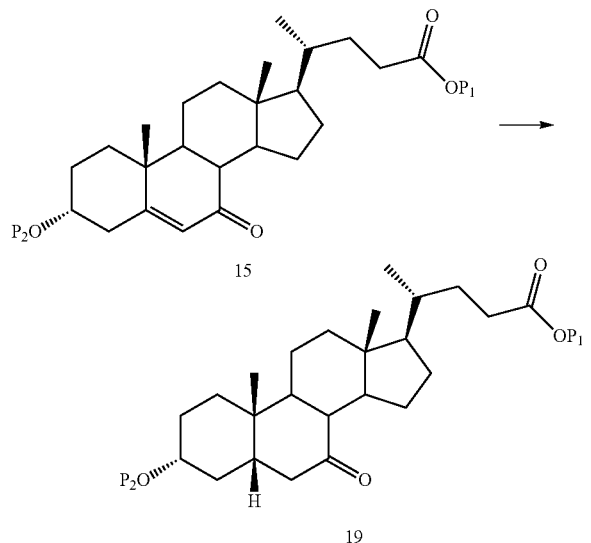

and

(10) deprotecting compound 19 to yield compound of Formula (I), wherein $R_1$ is oxo, or a pharmaceutically acceptable salt, solvate, or amino acid conjugate thereof.

15. The method of claim 14, wherein the selective reduction comprises hydrogenation.

16. The method of claim 15, wherein the hydrogenation is conducted with a catalyst and hydrogen gas.

17. The method of claim 6, wherein the stereoselective reduction of compound 15 to compound 16A comprises reacting compound 15 with K-Selectride.

18. The method of claim 10, wherein stereoselective reduction of compound 15 to compound 16B comprises reacting compound 15 with $NaBH_4$ and $CeCl_3.7H_2O$.

19. The method of claim 1, wherein alkylating of compound 10 comprises reacting compound 10 with methyl acrylate or methyl propiolate in the presence of $EtAlCl_2$ or $MeAlCl_2$ to yield compound 11.

20. The method of claim 1, wherein one or more steps is conducted under flow chemistry conditions.

* * * * *